United States Patent [19]
Revanker

[11] Patent Number: 6,069,132
[45] Date of Patent: May 30, 2000

[54] PHOSPHAZOLE COMPOUNDS

[76] Inventor: Ganapathi R. Revanker, 180 N. Milltrace Dr., The Woodlands, Tex. 77381

[21] Appl. No.: 08/910,291

[22] Filed: Aug. 13, 1997

Related U.S. Application Data

[60] Provisional application No. 60/023,907, Aug. 14, 1996.

[51] Int. Cl.$^7$ .......................... A61K 31/70; C07H 19/00; C07D 273/00
[52] U.S. Cl. .............. 514/43; 514/47; 514/261; 536/27.13; 536/27.14; 536/27.2; 544/264
[58] Field of Search ............... 514/43, 47, 261; 536/27.13, 27.14, 27.2; 544/264

[56] References Cited

U.S. PATENT DOCUMENTS

| | | | |
|---|---|---|---|
| 3,816,119 | 6/1974 | Bilofsky et al. | 96/3 |
| 3,932,455 | 1/1976 | Bilofsky et al. | 260/315 |
| 5,026,836 | 6/1991 | Robins et al. | 536/27.13 |

OTHER PUBLICATIONS

Rodionova et al., "Reaction of Diphenylphosphinous Isocyanate with Dimethyl Acetylenedicarboxylate," *J. General Chemistry of the USSR*, (45(7, pt. 2), 1623 (Jan. 10, 1976, English translation; Jul. 1975, Russian original).

Konovalova et al., "Reactions of Dialkyl Phosphorisocyanatidites with Diethyl Fumarate," *J. General Chemistry of the USSR*, 49(8, pt. 2), 1675 (Feb. 10, 1980, English translation; Aug. 1979, Russian original).

Panevin et al., "Reaction of Diphenoxyphosphinous Isocyanate with Dimethyl Acetylenedicarboxylate," *J. General Chemistry of the USSR*, 53(2, pt. 2), 420–421 (Aug. 10, 1983, English translation; Feb. 1983, Russian original).

Revanker et al., "Synthesis and Antimicrobial Activity of Certain Imidazo [1,2–a] pyrimidines," *J. Medicinal Chemistry*, 18(12), 1253–1255 (Dec. 1975).

*Primary Examiner*—L. Eric Crane
*Attorney, Agent, or Firm*—Martin L. McGregor

[57] ABSTRACT

A class of substituted and unsubstituted nucleo-base analogs and related azoles, designated as "phosphazoles," is disclosed, certain preferred embodiments having the basic structure of

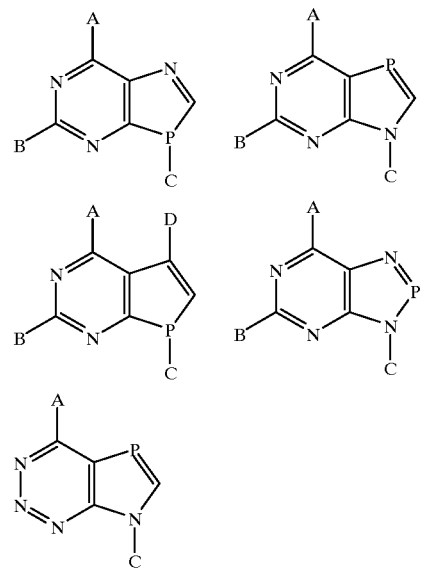

Also disclosed are methods of making and using the new compounds.

20 Claims, 12 Drawing Sheets

Inhibitions of TNFα Production in THP-1 Cells 6h Post Induction with LPS.

Effect of Compound T70241 on Extra- and Intracellular Protein

PHOSPHAZOLE COMPOUNDS

CROSS-REFERENCE TO RELATED APPLICATIONS

This application claims the benefit of a U.S. Provisional Application for a Patent, No. 60/023,907 filed Aug. 14, 1996.

STATEMENT REGARDING FEDERALLY SPONSORED RESEARCH OR DEVELOPMENT

Not Applicable

BACKGROUND OF THE INVENTION

1. Field of the Invention

The present invention generally relates to organic compounds in which a non-natural heteroatom is part of a 5-member ring, and particularly of nucleo-bases and their analogs comprising such 5-membered rings. More particularly, the invention relates to such compounds wherein phosphorus is a heteroatom.

2. Description of the Related Art

Phosphorus is not found free in nature, it always occurring in the fully oxidized state as phosphate. It is widely distributed in the phosphate form in all living cells, and plays a vital role in life processes such as energy storage and utilization in the form of nucleoside triphosphates. There is no known organism in which the chemistry of phosphorus is not utilized. The highly polymerized phosphate esters (such as are found in nucleic acid polymers, DNA or RNA) are the normal constituents of all cells. Although phosphorus is present in all nucleic acids as the oxidized phosphate form, the presence of phosphorus as a hetero atom replacing nitrogen in the purine base of nucleic acids, for example, is not yet known.

Several phosphono pyrimidine/purine nucleosides in which the phosphono group is attached directly to a carbon atom of the heterocycle, but not incorporated into the heterocyclic ring, have been reported (1, 2). Diethyl 6-chloro-9-(β-D-ribofuranosyl)purine-8-phosphate, having the following structural formula (compound 1):

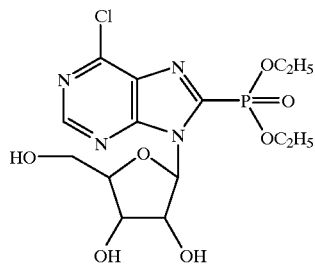

1 exhibits significant activity against vaccinia, vesicular stomatitis and coxsackie B4 viruses in culture. This compound is also inhibitory to the proliferation of the murine leukemia (L1210), murine mammary carcinoma (FM3), human B-lymphoblast (Raji) and human T-lymphoblast (Molt-4F) tumor cell lines in culture (1).

The synthesis of 1,3-benzazaphosphole, having the following structural formula (compound 2):

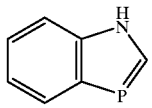

2 is described by Issleib et al. (3). 1,3-Azaphospholo[1,2-a]pyridine and 1,2,4-diazaphospholo[1,5-a]pyridine have also been synthesized (4). These studies have shown that such condensed systems containing trivalent phosphorus are much more stable than had been previously known. They are not attacked readily by dilute mineral acids and alkalies (3). Further, 3-methyl-1,3-benzazaphosphole, prepared by alkylation of the lithium salt of 1,3-benzazaphosphole with methyl iodide, and having the following structural formula (compound 3) is stable.

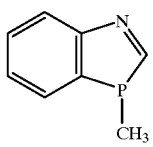

3

A single crystal X-ray diffraction analysis of 1,5-dimethyl-1,2,4,3-triazaphospholine, which has the following structural formula (compound 4):

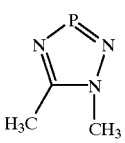

4 shows that both of the P-N distances in that molecule are identical, suggesting a PπNπ electron delocalized system in 1,5-dimethyl-1,2,4,3-triazaphosphole (5).

The synthesis of 1-β-D-ribofuranosyl-1,2,4-lambda-3-diazaphosphole-3-thiocarboxamide, and its effect against L1210 in mice is described by Riley et al. (115).

Conventional nucleo-base analogs have previously been evaluated for their toxicity to normal cells as well as for specific therapeutic efficacy against certain tumors or viruses, for example, using assay systems based on the inhibition of cytokines such as TNFα or IL-1β, as well as HCMV inhibition, among other methods. For the purposes of this disclosure a "nucleo-base" means adenine, guanine, thymine, cytosine or uracil.

Tumor necrosis factor alpha (TNFα)

Tumor necrosis factor alpha (TNFα), a mononuclear phagocytic cell derived protein, was originally described as a product of activated macrophages and shown to display tumoricidal activity (6–9). Extensive research during the last few years has made it apparent that TNFα is a highly pleiotropic cytokine (10) and may play a role in tumorigenesis, septic shock, multiple sclerosis, cachexia, inflammation, autoimmunity, and other immunological and pathological reactions (11). There are two forms of TNFα, a type II membrane protein of relative molecular mass 26,000 (26 kDa) and a soluble, 17 kDa form generated from the cell-bound protein by proteolytic cleavage. Several different types of tumors have been described in which TNFα acts as an autocrine growth factor, including leukemias, ovarian tumors, renal cell carcinoma, breast adenocarcinoma, neuroblastoma, and glioblastoma (12–16). These tumors express TNFα and its receptors and furthermore proliferate in response to the cytokine. Agents that can block the production of TNFα in these different tumor cell types may have potential as antitumor agents.

Cytokines such as TNFα and interleukin-1β (IL-1β) also play a central role in the regulation of the immune system and they have been implicated in inflammatory processes as well as in the pathogenesis of many diseases (17, 18). TNFα, first associated with tumor regression and with cachexia accompanying chronic invasive diseases, is now established as an immune modulator in normal and chronic inflammation situations as well as with septic shock (19). Deregulated production of TNFα in humans is thought to contribute to the development of diseases such as cancer-associated cachexia (20), endotoxic shock (21), graft versus host disease (22), autoimmunity (23) and rheumatoid arthritis (24, 25). Therefore, agents that can inhibit the production or maturation of TNFα and IL-1β in these different indications may have excellent therapeutic potential.

Since the role of TNFα and IL-β in the development of the septic shock syndrome and other ailments has been recognized (26), attempts have been made to suppress the production of these pathogenetic factors. Phosphodiesterase (PDE) inhibitors (27) are potential agents for blocking the cytokine pathway due to their ability to suppress TNF production via elevation of intracellular adenosine 3',5'-cyclic phosphate (cAMP) (28). The suppression of TNFα production by adenosine and certain xanthine derivatives (e.g. pentoxifylline) (29) by inhibition of PDE activity has recently been demonstrated (30).

Human cytomegalovirus (HCMV)

Cytomegalovirus (CMV) is the largest and perhaps the most complex member of the herpesviridae family (31, 32). Infections with human cytomegalovirus (HCMV) are common and usually asymptomatic; however, the incidence and spectrum of disease in newborns and immunocompromised hosts establish this virus as an important human pathogen (33). HCMV infection has been detected in 0.5 to 2.5% of newborn infants and is the most common identified cause of congenital infection (34). Symptomatic infants (5–10% of infected infants) can die of complications within the first months of life but more commonly experience permanent neurological damage (35). Infections due to HCMV also represent a significant complication in bone marrow or organ transplant recipients (36, 37). For example after allogeneic bone marrow transplant, HCMV infections occur in approximately 60 to 70% of bone marrow recipients who were HCMV seropositive before transplantation or who were seronegative but received bone marrow from a seropositive donor. In either instance, the principle post-operative cause of death in this patient population is interstitial pneumonia developed from the active HCMV infection (38). Despite the development of new treatment regimens using antiviral drugs or human hyperimmune therapy, GMV pneumonia still has a fatality rate of approximately 50% (39–41).

One of the most widely used drugs today for HCMV infections is ganciclovir (DHPG) (42–44). Ganciclovir is a potent inhibitor of most human and animal herpes viruses in culture whereas much higher concentrations are needed to inhibit cell growth of normal cells. However, DHPG is toxic to bone marrow progenitor cells in culture which was predictive of DHPG's adverse effects in vivo in that most clinical toxicity is myelosuppression (45). This problem is most apparent in patients in need of long-term therapy such as those with AIDS, CMV retinitis and transplant recipients.

Another concern for patients on long-term DHPG therapy is the development of DHPG-resistant strains of HCMV (46, 47). The second anti-HCMV drug approved for use against HCMV retinitis in AIDS patients is foscarnet (PFA). This compound is a broad spectrum antiviral agent with observed activity against all known human herpesviruses (48). However, treatment with foscarnet has resulted in nephrotoxicity, hypocalcemia, and seizures in some patients (49). Therefore, additional efficacious, non-toxic drugs for use against HCMV infections are needed.

SUMMARY OF THE INVENTION

A novel class of compounds herein designated as "phosphazoles" is provided by the present invention, in which the trivalent phosphorus (P) is an integral part of the 5-member ring of a nucleo-base or of a related azole. Five different types of P-containing heterocyclic rings are disclosed: 1,3-azaphospholo[4, 5-d]pyrimidine,1,3-azaphospholo[5, 4-d]pyrimidine, phospholo[2,3-d]pyrimidine, 1,3-azaphospholo[4, 5-d]-v-triazine and 1,3,2-diazaphospholo[4,5-d]pyrimidine and representative compounds containing each of these rings are also disclosed. Certain preferred compounds of the present invention are nucleo-base analogs and the corresponding nucleosides/nucleotides bearing N-glycosyl or P-glycosyl substituted rings. Other preferred compounds are acyclic N-alkyl and P-alkyl substituted nucleo-base analogs. Applicant believes that this application is the first mention of P-substituted nucleo-base compounds.

Methods of making the phosphazoles of the present invention are disclosed. Certain preferred methods include synthetically introducing a P heteroatom into the imidizole ring of a purine nucleo-base; or synthetically introducing the P heteroatom into the pyrrole ring of a nucleo-base analog; or introducing a P heteroatom into a 1,2,3-triazole ring of a nucleo-base analog in place of a N atom.

Representative compounds of the present invention exhibit significant in vitro inhibition of TNFα and IL-1β production in THP-1 cells and PBMCs. Representative compounds of the present invention also exhibit in vitro antiviral activity against HCMV.

Compounds of the present invention, or pharmaceutical compositions thereof, provide a new class of phosphorus containing heterocyclic compounds, and the corresponding nucleosides/nucleotides that will find widespread application in medical, agricultural and industrial use similar, or superior, to the known analogous compounds not containing a phosphorus in the heterocyclic ring. Other features and advantages of the present invention will be apparent from the following description of the presently preferred embodiments, together with the accompanying Tables and Figures.

DETAILED DESCRIPTION OF THE PREFERRED EMBODIMENT

Figure 1A:
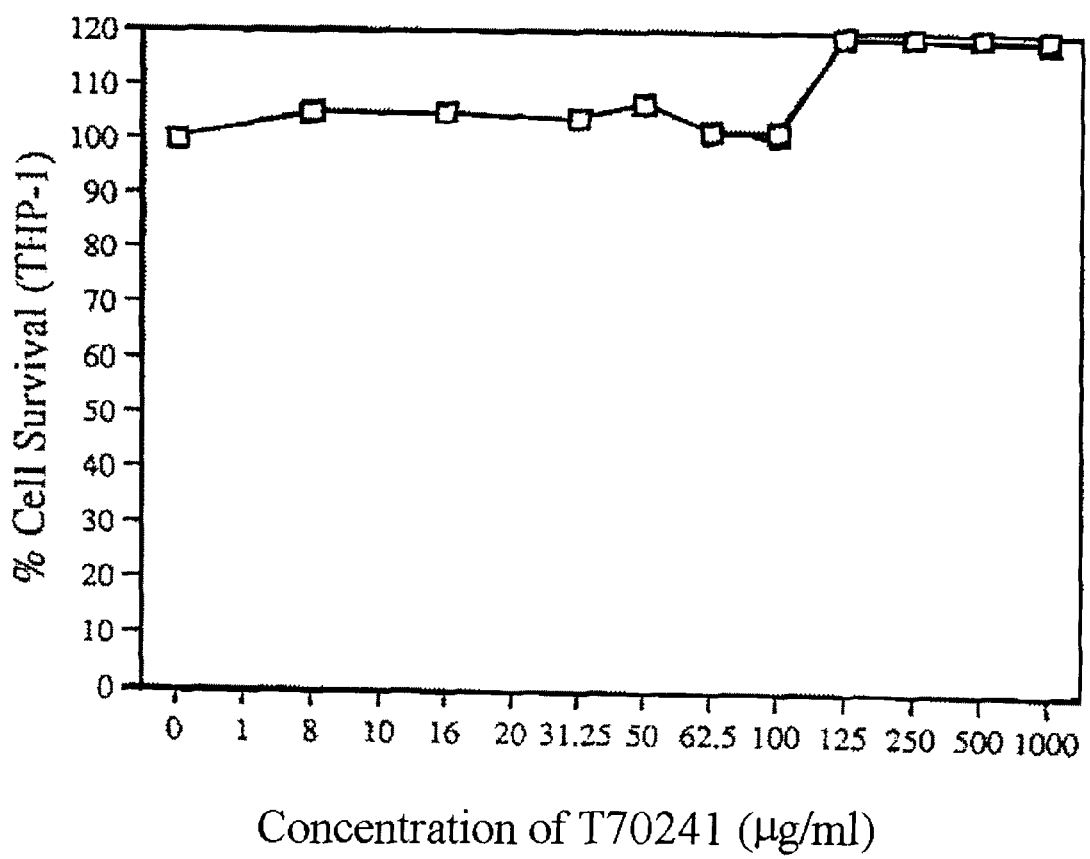
FIGS. 1A and 1B shows the in vitro toxicity and efficacy, respectively, of the adenine analog, compound 10 in THP-1 cells stimulated with LPS.

The new class of compounds of the present invention, called "phosphazoles" are substituted pyrimidine fused derivatives of three 5-member heterocyclic rings (compounds 5, 6 and 7), wherein

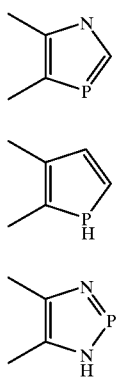

trivalent phosphorus (P) is an integral part of the heterocycle. Among the preferred embodiments of the present invention are compounds having P introduced into a nucleobase or related heterocycle and the corresponding nucleoside, nucleotide or 3',5'-cyclic nucleotide, or analogs thereof. Phosphazoles can be used in pharmaceuticals or in industrial or agricultural applications, similar to other nucleo-base analogs, with some embodiments of this class being equivalent or superior to known nucleo-base derivatives or related compounds.

The following examples are offered by way of illustration only and are not intended to limit the scope of the invention in any manner. The methods of the invention being as readily applicable to any substitution of a heterocycle containing a phosphorus atom in the ring system.

I. Synthesis of Phosphazoles Based on the 1,3-Azaphospholine Moiety

EXAMPLE 1

Modified Imidizole Ring (1,3-Azaphospholine)

The fundamental 1,3-azaphospholine ring was formed by substituting phosphorus for the oxygen atom in a suitable starting material such as 5-aminooxazole-4-carbonitrile (compound 8). The 5-aminooxazole-4-carbonitrile (compound 8), was prepared according to the method by Ferris and Orgel (50). Treatment of 5-aminooxazole-4-carbonitrile (compound 8) with tris(trimethyl-silyl)-phosphine (TTP) (51) in the presence of naked fluoride ion, such as a mixture of 18-Crown-6/KF (commercially available from Aldrich Chemical Co., Milwaukee, Wis. 53233) in anhydrous toluene at reflux temperature gave the key intermediate, 4-amino-1H-1, 3-azaphospholine-5-carbonitrile (compound 9) in a modest yield. The preparation of compound 9 is described in more detail as follows:

Preparation of 4-Amino-1H-1,3-azaphospholine-B-carbonitrile (compound 9)

Dry argon was bubbled for 5 min into a suspension of 18-crown-6 (50 mg) and dry potassium fluoride (3.5 g, 60 mmol) in dry toluene (110 mL). To this suspension, tris (trimethylsilyl)phosphine (51) (21.0 mL, 72.3 mmol) and 5-amino-oxazole-4-carbonitrile (50) (compound 8, 6 g, 61.8 mmol) were added and the mixture was heated under reflux for 14 h under an argon atmosphere. The reaction mixture was allowed to cool to room temperature and methanol (75 mL) was added under an argon atmosphere. After stirring for 2 h, the pH of the solution was adjusted to 5. Silica gel (50 g) was added and after stirring for 2 h, the solvents were evaporated to dryness under reduced pressure. The dry powder was placed on a silica gel column (4×10 cm). The column was flash eluted with hexane containing 0–20% ethyl acetate. Eluate containing the desired product was evaporated to yield 1.75 g (23%) of white powder. Ir (KBr): v 640 (=P-C), 1200 (-P=CH), 2205 (CN), and 3280–3440 (NH, $NH^2$) $cm^{-1}$. $^{31}p$ nmr ($CDCl_3$): δ 72.17. $^1H$ nmr (DMSO-$d_6$): δ 5.75 (br, 2 H, $NH_2$), 8.00 (dd, 1 H, $C_2H$), and 12.25 (br s, 1 H, NH). Anal. Calcd. for $C_4H_4N_3P$: C, 38.41; H, 3.22; N, 33.60; P, 24.76. Found: C, 38.73; H, 3.19; N, 33.27; P, 24.51.

The phosphorus (P) atom was introduced into the heterocycle in place of the oxygen (O) by a ring-opening and recyclization mechanism. This ring-opening and recyclization reaction is believed to be facilitated by the presence of a nitrile function at the meta position to the ring oxygen, as indicated in the steps shown below.

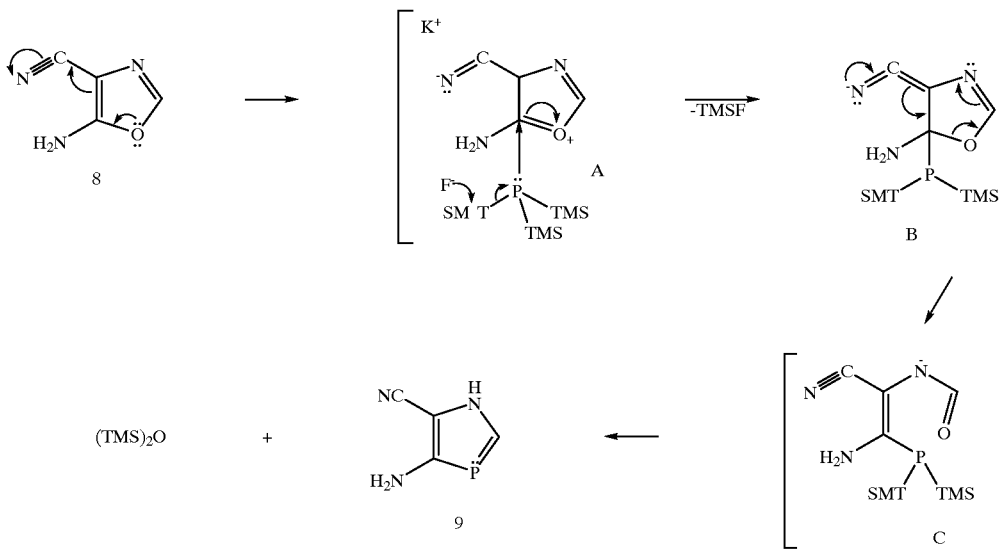

The ring-opening involves the initial formation of the oxazolium zwitterion (A) by the reaction of compound 8 and the naked fluoride ion, generated by 18-crown-6/KF. Nucleophillic attack on the tertiary carbon atom of the oxazolium zwitterion (A) by the tris (trimethylsilyl) phosphine gives the intermediate (B). This should be followed by a ring-opening to form the unstable phosphonium salt (C), which readily recyclizes into compound 9 with the separation of hexamethyldisiloxane. The compound, 4-amino-1H-1,3-azaphospholine-5-carbonitrile (compound 9), is obtained as a stable, light yellow amorphous powder. From this key intermediate compound numerous compounds are synthesized, the preferred embodiments of which are described below.

EXAMPLE 2

Adenine Analog (T70241, compound 10)

4-Amino-1H-1,3-azaphospholine-5-carbonitrile from Example 1 is reacted with formamidine acetate in ethanol at reflux temperature to form the ring annulated product 7-amino-1H-1,3-azaphospholo[4,5-d]pyrimidine (the adenine congener, compound 10):

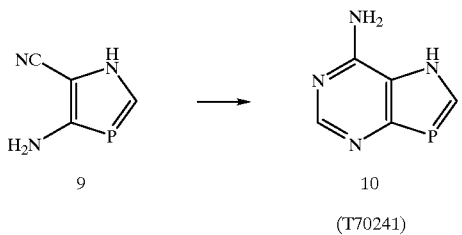

Preparation of 7-Amino-1H-1,3-azaphospholo[4,5-d] pyrimidine (compound 10)

To a solution of 4-amino-1H-1,3-azaphospholine-5-carbonitrile (compound 9, 0.7 g, 5.6 mmol) in absolute ethanol (50 mL) was added formamidine acetate (1.16 g, 11.2 mmol) and the mixture was heated under reflux for 1.5 h. The product that precipitated after cooling was collected by filtration. The filtrate was evaporated under reduced pressure, the residual solid was dissolved in methanol (10 mL) and impregnated onto silica gel (10 g). The solvent was evaporated and the dry powder was loaded on a silica gel column (2×10 cm). The column was flash eluted with dichloromethane containing 0–8% methanol. Eluate containing the desired product was evaporated and the residue was combined with the solid obtained previously. Crystallization of the combined solid from aqueous ethanol gave 0.72 g (84.5%) of the product, mp>300° C.; Ir (KBr): ν720 (=P-C), 1215 (-P=CH), and 3100–3440 (NH, $NH_2$) $cm^{-1}$. Uv ($H_2O$): λmax244 nm (ε27,500), and 304 (6900); $^{31}$p nmr (DMSO-$d_6$): δ74.52. $^1$H nmr (DMSO-$d_6$): δ 7.13 (s, 2 H, $NH_2$), 8.19 (s, 1 H, $C_5H$), 8.91 (d, 1 H, $C_2H$), and 12.50 (br s, 1 H, NH). Anal. Calcd. for $C_5H_5N_4P$: C, 39.48; H, 3.31; N, 36.84; P, 20.36. Found: C, 39.86; H, 3.25; N, 36.53; P, 20.32.

EXAMPLE 3

Hypoxanthine Analog (compound 12)

Hydrolysis of the nitrile function of 4-amino-1H-1,3-azaphospholine-5-carbonitrile (compound 9), from Example 1, is carried out by treatment with 0.1N aqueous NaOH at gentle reflux for 5 hours to obtain 4-amino-1H-1,3-azaphospholine-5-carboxamide (compound 11). The procedure is described in more detail, as follows:

Preparation of 4-Amino-1H-1,3-azaphospholine-5-carboxamide (compound 11)

A suspension of 4-amino-1H-1, 3-azaphospholine-5-carbonitrile (compound 9, 0.5 g, 4 mmol) in aqueous sodium hydroxide solution (28 mL, 0.11 N) was heated at 110° C. (oil bath temp) for 6 h. The reaction mixture was allowed to cool to room temperature and then cooled in an ice bath. The pH of the solution was adjusted to 6.8 (using 2 N hydrochloric acid) during which time some product precipitated. The flask was kept in the refrigerator overnight and the solid product was collected by filtration and dried to yield 0.4 g (70%) of the product, mp 184–186° C.; Ir (KBr): ν3185–3445 (NH, $NH_2$), and 1720 (C=O) $cm^{-1}$. $^1$H nmr (DMSO-$d_6$): δ 6.25 (br s, 2 H, $NH_2$), 6.94 (s, 2 H, $CONH_2$), 7.85 (dd, 1 H, $C_2H$), and 11.51 (br s, 1 H, NH). Anal. Calcd. for $C_4H_6N_3OP$: C, 33.57; H, 4.23; N, 29.37; P, 21.65. Found: C, 33.68; H, 4.05; N, 28.83; P, 21.38.

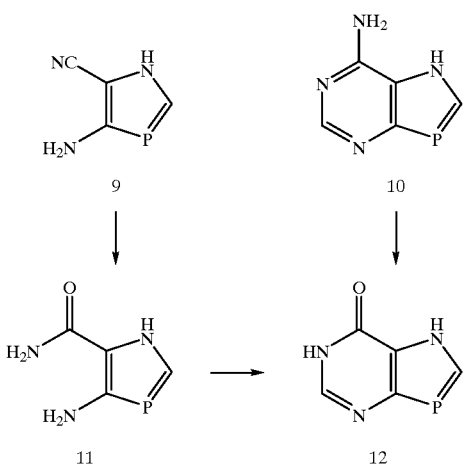

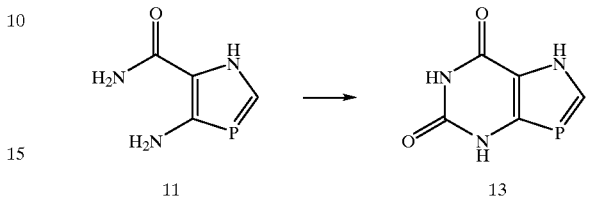

Compound 11 is then fused with formamide to form the hypoxanthine analog, 1,3-azaphospholo[4,5-d]pyrimidin-7(1H,6H)-one (compound 12) using the following procedure. A mixture of 4-amino-1H-1,3-azaphospholine-5-carboxamide (compound 11, 0.36 g, 2.5 mmol) and formamide (0.5 mL, 12.5 mmol) in a 5 mL pear shaped flask was placed in a preheated oil bath at 185° C. for 45 min. The flask was allowed to cool to room temperature. The solid thus obtained was triturated with cold water (5 mL). The solid was collected by filtration and crystallized from aqueous ethanol to yield 0.3 g (78%) of the title compound, mp>300° C. Ir (KBr): ν710 (═P-C), 1170 and 1200 (-P═CH), 1650 (C═O), and 2860–3080 (NH, NH$_2$) cm$^{-1}$. Uv (MeOH): λmax244 nm (ε43,300), and 274 (6200). $^{31}$p nmr (DMSO-d$_6$): δ 85.54; $^1$H nmr (DMSO-d$_6$): δ 7.90 (s, 1 H, C$_5$H), 8.66 (dd, 1 H, C$_2$H), 12.22 (br s, 1 H, NH), and 13.32 (br s, 1 H, NH). Anal. Calcd. for C$_5$H$_4$N$_3$OP: C, 39.23; H, 2.63; N, 27.45; P, 20.23. Found: C, 39.39; H, 2.75; N, 27.08; P, 20.02.

This hypoxanthine analog (compound 12) was found to be identical to the one obtained by deamination of adenine analog (compound 10) with aqueous nitrous acid.

EXAMPLE 4
Xanthine Analog (compound 13)

4-Amino-1H-1,3-azaphospholine-5-carboxamide (compound 11), from Example 3, is fused with urea at 160° C. for 45 min to obtain the xanthine analog 1,3-azaphospholo[4,5-d]pyrimidine-5,7(1H, 4H, 6H)-dione (compound 13), by the following procedure:

Preparation of 1,3-Azaphospholo[4,5-d]pyrimidine-5,7(1H, 4H,6H)-dione (compound 13)

A finely powdered mixture of 4-amino-1H-1,3-azaphospholine-5-carboxamide (compound 11, 2.14 g, 14.96 mmol) and urea (4.29 g, 71.43 mmol) was placed in an open round bottom flask. The flask was immersed up to the neck in a preheated oil bath at 160° C. with efficient stirring. Heating was continued until the starting material (compound 11) was consumed (TLC on silica gel plate using CH$_2$Cl$_2$:MeOH, 85:15, as developing solvent). The reaction mixture was cooled to 25° C. and sonicated with cold water (25 mL) for 1 h. The precipitate was collected by filtration, washed thoroughly with cold water (3×10 mL). The solid was suspended in hot (80° C.) water (25 mL) and 0.1 N NaOH was added dropwise until a clear solution was obtained. The solution was filtered and the pH of the filtrate was adjusted to 6 with acetic acid. The solid that separated was collected by filtration, washed with ice cold water (5×15 mL), followed by ethanol (3×15 mL) and dried at 100° C. under vacuum for 15 h to yield 2.16 g (85%) of the title compound, mp>300° C. Uv (MeOH): λmax242 nm (ε39,300), 276 (9200), and 300 sh (4000). $^1$H nmr (DMSO-d$_6$): δ 8.43 (d, 1 H, J =43.5 Hz, C$_2$H), 11.07 and 11.21 (2s, 2 H, 2NH). Anal. Calcd. for C$_5$H$_4$N$_3$O$_2$P.0.5H$_2$O:C, 33.72; H, 2.83; N, 23.59; P, 17.39. Found: C, 33.72; H, 2.62; N, 23.50; P, 17.61.

EXAMPLE 5
6-Thiopurine Analog (compound 15)

The hypoxanthine analog from Example 3 is reacted with POCl$_3$ at reflux temperature for 50 min to form 7-chloro-1H-1,3-azaphospholo[4,5-d]pyrimidine (compound 14). Reaction of compound 14 with thiourea in boiling ethanol produced the 6-thiopurine analog 1,3-azaphospholo[4,5-d]pyrimidin-7(1H, 6H)-thione (compound 15). Compounds 14 and 15 are prepared as follows:

Preparation of 7-Chloro-1H-1,3-azaphospholo[4,5-d]pyrimidine (compound 14)

A mixture of 1,3-azaphospholo[4,5-d]pyrimidin-7(1H, 6H)-one (compound 12, 5.0 g, 32.66 mmol) and phosphorus oxychloride (125 mL) was heated under reflux with stirring for 50 min under an argon atmosphere. The reaction mixture was cooled to room temperature and unreacted phosphorus oxychloride was removed under reduced pressure at 25° C. The residual syrup was cooled to 0° C. and carefully neutralized with 2 N aqueous ammonium hydroxide. The precipitate formed was collected by filtration, washed with cold water (2×25 mL) and dried over P$_2$O$_5$ under vacuum, first at 25° C. and then at 100° C. The dry solid was crystallized from acetonitrile to yield 2.73 g (49%) of the title compound, mp>300° C. (became black at 190° C.). $^1$H nmr (DMSO-d$_6$): δ 8.81 (s, 1 H, C$_5$H), 9.36 (dd, 1 H, J$_{C2H,NH}$=4.8 Hz, J$_{C2H,P}$=39.4 Hz, C$_2$H), and 13.68 (br s, 1 H, NH). Anal. Calcd. for C$_5$H$_3$ClN$_3$P: C, 35.02; H, 1.76; Cl, 20.67; N, 24.50; P, 18.05. Found: C, 35.36; H, 2.08; Cl, 21.10; N, 24.21; P, 17.78.

Preparation of 1,3-Azaphospholo[4,5-d]pyrimidin-7(1H, 6H)-thione (compound 15)

A mixture of 7-chloro-1H-1,3-azaphospholo[4,5-d]pyrimidine (compound 14, 0.23 g, 1.33 mmol), thiourea (0.15 g, 2.0 mmol) and absolute ethanol (10 mL) was heated under reflux for 90 min with stirring under anhydrous conditions. The reaction mixture was cooled to 25° C. and then the solvent was evaporated in vacuo. The residue was sonicated with ice-cold water (10 mL) and the precipitate was collected by filtration, washed with cold water (3×5 mL) and dried over P$_2$O$_5$ in vacuo first at 25° C. and then at 100° C. to yield 0.12 g (55%) of the title compound, mp>300° C. Ir (KBr): ν710 (═P-C), 1170 and 1200 (-P═CH), 1580 (C═S), and 3280 (NH) cm$^{-1}$. Uv (MeOH): λmax230 nm (ε19,400), 276 (9400), and 338 (17,200). $^1$H nmr (DMSO-d$_6$): 8.11 (s, 1 H, C$_5$H), 8.93 (dd, 1 H, J$_{C2H,NH}$=5.4 Hz, J$_{C2H,P}$=39.6 Hz, C$_2$H), δ 13.15 (s, 1 H, NH), and 13.82 (s, 1 H, NH). Anal. Calcd. for C$_5$H$_4$N$_3$PS.H$_2$O: C, 32.08; H, 3.23; N, 22.45; S, 17.13. Found: C, 32.39; H, 3.61; N, 22.54; S, 17.40.

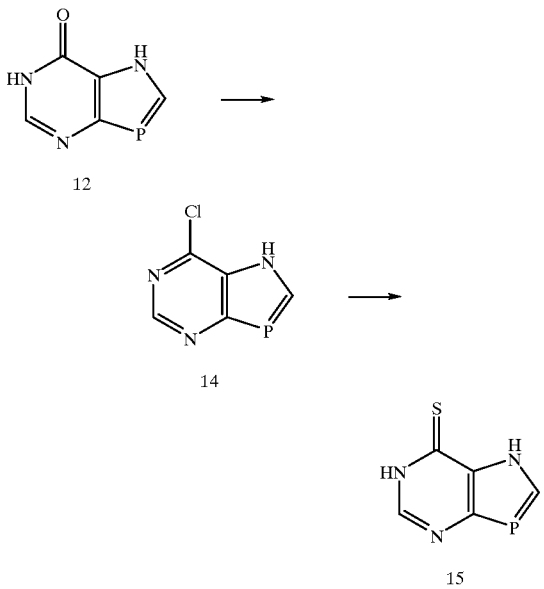

EXAMPLE 6
Guanine Analog (compound 18)

The guanine analog 5-amino-1,3-azaphospholo[4,5-d]pyrimidin-7(1H, 6H)-one (compound 18) is obtained from the amino-carboxamide analog of Example 3 by reacting with benzoylisothiocyanate to form 4-(N'-benzoylthiocarbonyl)amino-1H-1,3-azaphospholine-5-carbox-amide (16), which is then reacted with CH$_3$I in 0.1N NaOH solution to give 4-(N'-benzoyl-S-methylisothiocarbamoyl)amino-1H-1,3-azaphospholin-5-carboxamide (17), which in the presence of ammonia, forms the guanine analog (compound 18). The preparation of compounds 16–18 are described in more detail as follows:

Preparation of 4-(N'-Benzoylthiocarbonyl)amino-1H-1,3-azaphospholine-5-carboxamide (compound 16)

4-Amino-1H-1,3-azaphospholine-5-carboxamide (compound 11, 0.95 g, 6.64 mmol) was dissolved in a mixture of ethanol (15 mL) and water (7.5 mL) at 75° C. The resulting solution was cooled to 35° C. Benzoylisothiocyanate (1.79 g, 10.97 mmol) was added dropwise under an argon atmosphere with stirring. The mixture was stirred at room temperature for 2 h and the precipitate was collected by filtration, washed with water (3×15 mL) and then with cold ethanol (10 mL). The solid was dried over P$_2$O$_5$ in vacuo, first at 25° C. (8 h) and then at 80° C. (24 h) to yield 2.01 g (99%) of the title compound, mp>300° C. $^1$H nmr (DMSO-d$_6$): δ 7.50–7.66 (m, 5 H, m, p-protons of benzoyl and CONH$_2$), 7.97 (d, 2 H, o-protons of benzoyl), 8.15 (dd, 1 H, J$_{C2H,NH}$=5. 4 Hz, J$_{C2H,P}$=39.0 Hz, C$_2$H), 11.31 (s, 1 H, NH), 12.57 (s, 1 H, NH), and 14.55 (s, 1 H, NH).

Preparation of 4-(N'-Benzoyl-S-methylizothiocarbamoyl)amino-1H-1,3-azaphospholine-5-carboxamide (compound 17)

To a solution of 4-(N'-benzoylthiocarbonyl)amino-1H-1,3-azaphospho-line-5-carboxamide (compound 16, 0.918 g, 3.0 mmol) in 0.1 N sodium hydroxide (115 mL) was added iodomethane (0.205 mL, 3.30 mmol) dropwise at 25° C. The mixture was stirred at 25° C. for 3 h, then cooled to 0° C. and acidified to pH 6 with acetic acid. The mixture was extracted with ethyl acetate (5×75 mL). The combined ethyl acetate extracts were dried over anhydrous sodium sulfate and concentrated to 25 mL under reduced pressure and allowed to stand at 25° C. for crystallization to occur. The crystalline material was collected by filtration and dried to give 0.21 g (22%) of the title compound, mp>250° C.(dec). $^1$H nmr (DMSO-d$_6$): δ 2.62 (s, 3 H, SCH$_3$), 7.47–7.64 (m, 5 H, benzoyl), 7.84 (s, 2 H, CONH$_2$), 8.39 (m, 1 H, C$_2$H), 12.44 (d, 1 H, NH), and 12.70 (br s, 1 H, NH).

Preparation of 5-Amino-1,3-azaphospholo[4,5-d]pyrimidin-7(1H,6H)one (compound 18)

A mixture of 4-(N'-benzoyl-S-methylisothiocarbamoyl)amino-1H-1,3-azaphospholine-5-carboxamide (compound 17, 2.0 g, 6.24 mmol) and 2% ammonia in dimethylformamide (60 mL) was placed in a closed steel reaction vessel and heated at 130° C. with stirring for 16 h. The mixture was cooled to 25° C., diluted with methanol (50 mL) and stirred in an open flask for 1 day. A white solid that separated from the reaction mixture was collected by filtration, washed with cold methanol (3×5 mL) and dried in vacuo at 100° C. The dry solid was dissolved in 2 N NaOH, filtered and the filtrate was acidified to pH 6 with glacial acetic acid to give a white precipitate. The precipitate was collected by filtration, washed with cold water (3×15 mL), followed by acetone (2×5 mL) and dried in vacuo at 100° C. to yield 0.50 g (48%) of the title compound, mp>300° C. Ir (KBr): ν690 (=P-C), 1170 and 1230 (-P=CH), 1690 (C=O), and 3170–3320 (NH$_2$) cm$^{-1}$. Uv (MeOH): λmax240 nm (ε26,900) and 276 (6850). $^1$H nmr (DMSO-d$_6$): δ 6.15 (br s, 2 H, NH$_2$), 8.38 (dd, 1 H, C$_2$H), 10.95 (br s, 1 H, CONH), and 12.76 (br s, 1 H, NH). Anal. Calcd. for C$_5$H$_5$N$_4$OP.0.5H$_2$O: C, 33.90; H, 3.41; N, 31.63; P, 17.49. Found: C, 34.07; H, 3.34; N, 31.31; P, 17.07.

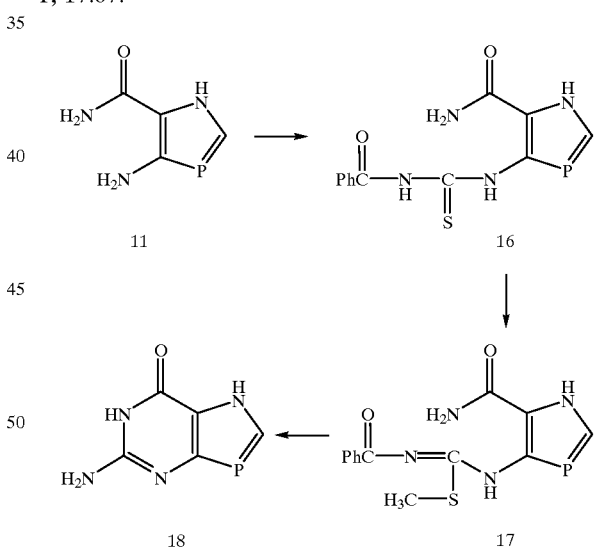

EXAMPLE 7
6-Thioguanine Analog (compound 19b)

The guanine analog from Example 6 is heated under reflux with POCl$_3$ at 140° C. for 50 min to form 5-amino-7-chloro-1,3-azaphospholo[4,5-d]pyrimidine (compound 19a), which on reaction with thiourea in boiling ethanol produced the 6-thioguanine analog 5-amino-1,3-azaphospholo[4,5-d]-pyrimidin-7(1H, 6H) -thione (compound 19b).

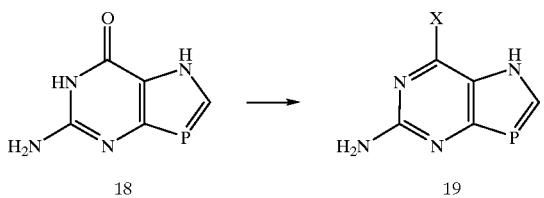

a) X = Cl
b) X = SH

EXAMPLE 8
Preparation of 1,4,6-Trimethyl-1,3-azaphospholo[4,5-d]pyrimidine-5,7-dione (Caffeine Analog)(compound 20)

A suspension of 1,3-azaphospholo[4, 5-d]pyrimidine-5,7 (1H, 4H,6H) -dione (compound 13, 0.2 g, 1.18 mmol) in DMF (5 mL) and N,N-dimethylformamide dimethyl acetal (15 mL) was heated at 80° C. for 55 h under anhydrous conditions. After cooling to room temperature the insoluble material was removed by filtration and the filtrate was evaporated in vacuo. The residue was coevaporated with toluene (10 mL) and purified by chromatography over a silica gel column (0.5×5 cm). The column was flash eluted with dichloromethane containing 1% methanol. The appropriate fractions containing the desired product were collected and evaporated to give 0.13 g (52%) of the title compound as a colorless powder, mp 166–168° C. Uv (MeOH): λmax240 nm (ε29, 350), 282 (7000), and 298 sh (4500). $^{31}$p nmr (DMSO-d$_6$): δ 48.48. $^1$H nmr (DMSO-d$_6$): δ 3.20 (s, 3 H, CH$_3$), 3.39 (s, 3 H, CH$_3$), 4.10 (s, 3 H, CH$_3$), and 8.46 (d, 1 H, J =43.5 Hz, C$_2$H). Anal. Calcd. for C$_8$H$_{10}$N$_3$O$_2$P: C, 45.50; H, 4.77; N, 19.90. Found: C, 45.77; H, 4.72; N, 19.87.

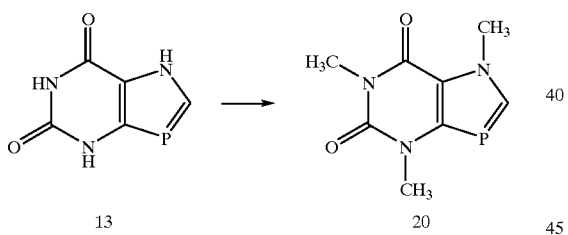

EXAMPLE 9
N-Substituted 7-Amino-1H-1,3-azaphospholo[4,5-d]pyrimidines.

A further embodiment includes phosphazole compounds having the structure:

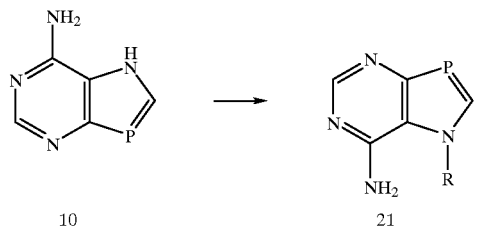

R is —(CH$_2$)$_4$CH$_3$
—(CH$_2$)$_5$CH$_3$
—CH$_2$CH=CH$_2$

—CH$_2$CH=CHCH$_2$CH$_3$ (cis and trans)

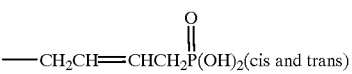

—CH$_2$CH=C(CH$_3$)$_2$
—(CH$_2$)$_3$CH$_2$OH

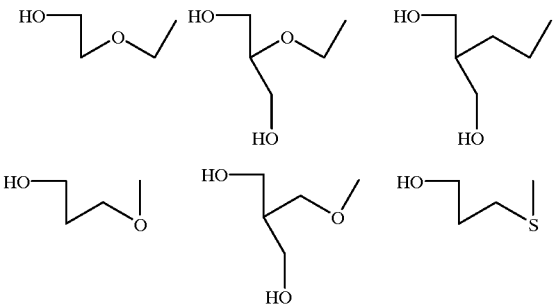
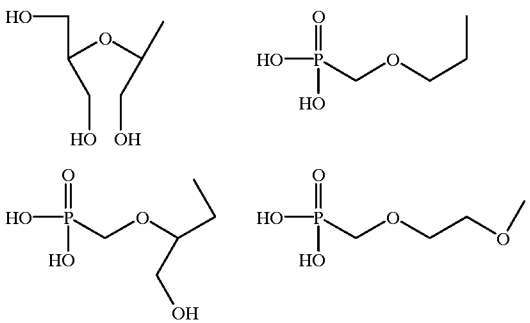
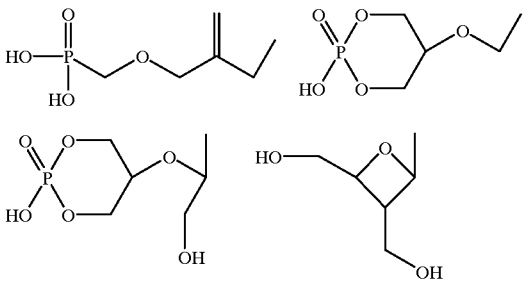
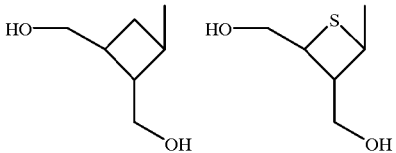
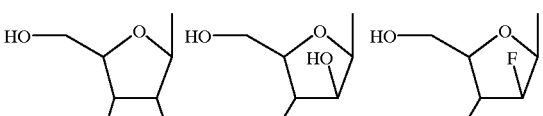
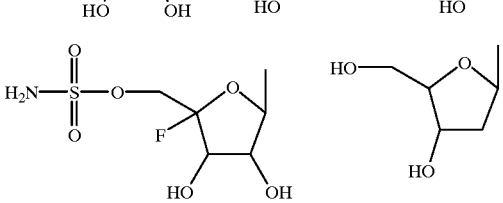

-continued

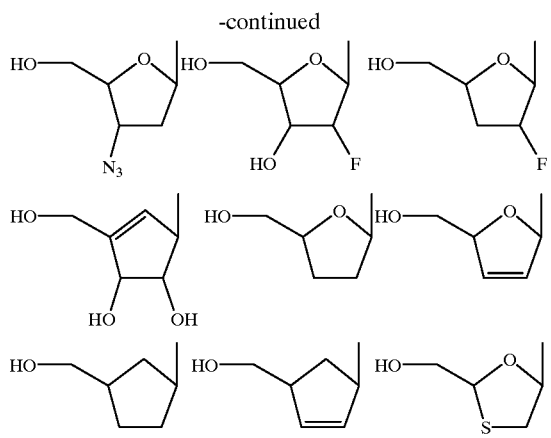

The synthesis of compounds corresponding to structure 21 was accomplished by the direct alkylation of the adenine analog 7-amino-1H-1,3-azaphospholo[4,5-d]pyrimidine (Example 2, compound 10) with requisite alkyl halides or properly protected glycosyl (carbohydrate) halides. In the case of glycosyl derivatives, subsequent deprotection of the condensed product under alkaline conditions is required. The procedure is described more specifically as follows:

Preparation of 7-Amino-1-(n-pentyl)-1,3-azaphospholo[4,5-d]pyrimidine [compound 21, R=(CH$_2$)$_4$CH$_3$]

7-Amino-1H-1,3-azaphospholo[4,5-d]pyrimidine (compound 10, 0.25 g, 1.64 mmol, dried by coevaporation with dry DMF, 15 mL) was suspended in dry DMF to which sodium hydride (80 mg, 2 mmol, 60% dispersion in mineral oil) was added under argon atmosphere. The mixture was stirred at room temperature for 40 min and 1-bromopentane (0.25 mL, 2 mmol) was added. The reaction was continued for 3 h and the solvent was evaporated. The residue was coevaporated with toluene (25 mL). The solid thus obtained was dissolved in a mixture of dichloromethane and methanol (1:1, 10 mL) and impregnated onto silica gel (10 g). The solvents were evaporated under reduced pressure and the dry powder was loaded on a silica gel column (2×10 cm). The column was flash eluted with dichloromethane containing 0–5% methanol to yield 0.26 g (71%) of the title compound, mp 196–198° C. Ir (KBr): ν690 (=P-C), 1220 (-P=CH), and 3110 and 3280 (NH$_2$) cm$^{-1}$. Uv (MeOH): λmax266 nm (ε23,300). $^{31}$p nmr (DMSO-d$_6$): δ 62.57. $^1$H nmr (DMSO-d$_6$): δ 0.83(t, 3 H, CH$_3$), 1.25 (m, 4 H, 2CH$_2$), 1.92 (m, 2 H, CH$_2$), 4.27 (t, 2 H, NCH$_2$), 8.37 and 8.67 (2s, 2 H, NH$_2$), 8.60 (d, 1 H, C$_5$H), and 9.03 (d, 1 H, J =54 Hz, C$_2$H). Anal. Calcd. for C$_{10}$H$_{15}$N$_4$P.0.5 CH$_2$Cl$_2$: C, 47.63; H, 6.09; N, 21.17. Found: C, 47.47; H, 6.09; N, 21.86.

Preparation of 7-Amino-1-(n-hexyl)-1,3-azaphospholo[4,5-d]pyrimidine [compound 21, R=(CH$_2$)$_5$CH$_3$]

7-Amino-1H-1,3-azaphospholo[4,5-d]pyrimidine (compound 10, 0.5 g, 3.29 mmol) was suspended in dry DMF to which sodium hydride (160 mg, 4 mmol, 60% dispersion in mineral oil) was added under an argon atmosphere. The mixture was stirred at room temperature for 40 min and 1-bromohexane (0.56 mL, 4 mmol) was added. The reaction was continued for 3 h and the solvent was evaporated. The residue was dissolved in dichloromethane (150 mL) and washed with water (25 mL). Organic layer was separated and the aqueous layer was extracted with dichloromethane (2×50 mL). The combined organic layer was dried (Na$_2$SO$_4$) and evaporated. The residue was purified by silica gel column (2×15 cm) chromatography eluting with dichloromethane containing 0–4% methanol. The appropriate fractions containing the desired product were evaporated to yield 0.53 g (68%), mp 220–222° C. Ir (KBr): ν690 (=P-C), 1220 (-P=CH), and 3295 (NH$_2$) cm$^{-1}$. Uv (pH 1): λmax 254 nm (ε23,700), 282 (11,500), and 314 (5200); (MeOH): λmax 266 (ε31,600); (pH 11): λmax 266 nm (ε33,300), and 330 (2200). $^{31}$p nmr (DMSO-d$_6$): 63.21. $^1$H nmr (DMSO-d$_6$): δ 0.80(t, 3 H, CH$_3$), 1.23 (br s, 6 H, 3CH$_2$), 1.92 (t, 2 H, CH$_2$), 4.24 (t, 2 H, NCH$_2$), 8.15 and 8.23 (2s, 2 H, NH$_2$), 8.44 (d, 1 H, C$_5$H), and 8.86 (d, 1 H, J=58.5 Hz, C$_2$H). Anal. Calcd. for C$_{11}$H$_{17}$N$_4$P: C, 55.92; H, 7.25; N, 23.72. Found: C, 55.49; H, 7.31; N, 23.28.

Preparation of 7-Amino-1-(4-acetoxybutyl)-1,3-azaphospholo[4,5-d]pyrimidine [compound 21, R=(CH$_2$)$_3$CH$_2$OAc]

To a suspension of 7-amino-1H-1,3-azaphospholo[4,5-d]pyrimidine (compound 10, 0.3 g, 2 mmol) in dry DMF (20 mL) was added sodium hydride (96 mg, 2.4 mmol) under an argon atmosphere. The mixture was stirred at ambient temperature for 30 min and 4-bromobutyl acetate (0.35 mL, 2.4 mmol) was added. After stirring for 3 h, DMF was evaporated and the residue was purified by chromatography over a silica gel column (2×15 cm). The column was flash eluted with dichloromethane containing 0–5% methanol. The homogeneous fractions containing the desired product were collected and evaporated under reduced pressure to yield 0.34 g (64%) of the title compound, mp 168–170° C. $^{31}$p nmr (DMSO-d$_6$): δ 62.34. $^1$H nmr (DMSO-d$_6$): δ 1.56 (m, 2 H, CH$_2$), 1.90 (m, 5 H, CH$_2$, CH$_3$), 4.00 (t, 2 H, NCH$_2$), 4.30 (t, 2 H, CH$_2$), 8.27 and 8.38 (2s, 2 H, NH$_2$), 8.50 (d, 1 H, C$_5$H), and 8.92 (d, 1 H, J =56.4 Hz, C$_2$H ). Anal. Calcd. for C$_{11}$H$_{15}$N$_4$O$_2$P: C, 46.99; H, 5.43; N, 19.49. Found: C, 46.69; H, 5.44; N, 19.37.

Preparation of 7-Amino-1-(4-hydroxybutyl)-1,3-amaphospholo-[4,5-d]pyrimidine [compound 21, R=(CH$_2$)$_3$CH$_2$OH]

A mixture of 7-amino-1-(4-acetoxybutyl)-1,3-azaphospholo[4,5-d]pyrimidine [compound 21, R=(CH$_2$)$_3$CH$_2$OAc], 0.3 g, 1.13 mmol) and methanolic ammonia (100 mL, saturated at 0° C.) was stirred overnight and the methanolic ammonia was evaporated in vacuo. The residue was purified by silica gel column chromatography. The column was flash eluted with dichloromethane containing 0–8% methanol to yield 0.2 g (79%) of the title compound, mp 164–166° C. Ir (KBr): ν700 (=P-C), 1220 (-P=CH), and 2940, 3060 and 3260 (NH$_2$, OH) cm$^{-1}$. Uv (pH 1): λmax254 4m (ε26,000), 282 (13,100), and 314 (5900); (MeOH): λmax266 nm (ε35,900), and 330 (3100); (pH 11): 266 nm (ε38,500), and 334 (3300). $^{31}$p nmr (DMSO-d$_6$) 63.64. $^1$H nmr (DMSO-d$_6$): δ 1.41 (m, 2 H, CH$_2$), 1.97 (m, 2 H, CH$_2$), 3.40 (t, 2 H, CH$_2$), 4.34 (t, 2 H, CH$_2$), 4.47 (br s, 1 H, OH), 8.28 and 8.39 (2s, 2 H, NH$_2$), 8.53 (d, 1 H, C$_5$H), and 8.96 (d, 1 H, J =56.4 Hz, C$_2$H). Anal. Calcd. for C$_9$H$_{13}$N$_4$OP. 0.25 CH$_2$Cl$_2$: C, 45.26; H, 5.54; N, 22.83. Found: C, 45.05; H, 5.49; N, 22.73.

Preparation of 7-Amino-1-[(2-acetoxyethoxy)methyl]-1,3-azaphospholo-[4,5-d]pyrimidine [compound 21, R=CH$_2$OCH$_2$CH$_2$OAc]

To a suspension of 7-amino-1H-1,3-azaphospholo[4,5-d] pyrimidine (compound 10, 0.5 g, 3.29 mmol) in DMF (20 mL) was added NaH (0.16 g, 4 mmol) under an argon atmosphere. After stirring the mixture at room temperature for 40 min, the reaction flask was cooled to −50° C. and a solution of 2-(acetoxyethoxy)methyl bromide (108) (0.78 g, 3.96 mmol) in DMF (5 mL) was added. The reaction flask was allowed to warm to room temperature in 1.5 h and the reaction was continued for further 2 h. The solvent was evaporated in vacuo and the residue was coevaporated with toluene (10 mL). The residue was dissolved in a mixture of dichloromethane and methanol (1:1, 10 mL) and impregnated onto silica gel (10 g). The sovents were evaporated and the dry powder was loaded on a silica gel column (2×15 cm). The column was flash eluted with dichloromethane containing 0–7% methanol. The appropriate fractions containing the desired product were evaporated to yield 0.62 g (70%) of the title compound, mp 134–135° C. $^1$H nmr (DMSO-$d_6$): δ 1.89 (s, 3 H, $CH_3$), 3.69 (dd, 2 H, $CH_2$), 4.05 (t, 2 H, $CH_2$), 5.67 (s, 2 H, $CH_2$), 8.57 and 8.88 (2s, 2 H, $NH_2$), 8.70 (d, 1 H, C5H), and 9.00 (d, 1 H, J =51.9 Hz, $C_2H$). Anal. Calcd. for $C_{10}H_{13}N_4O_3P \cdot 0.4$ $CH_2Cl_2$: C, 39.74; H, 4.60; N, 18.54. Found: C, 40.04; H, 4.20; N, 18.38.

Preparation of 7-Amino-1-[(2-hydroxyethoxy)methyl]-1,3-azaphospholo-[4,5-d]pyrimidine [compound 21, R=$CH_2OCH_2CH_2OH$]

A mixture of 7-amino-1-[(2-acetoxyethoxy)methyl]-1,3-azaphospholo[4,5-d]pyrimidine (compound 21, R=$CH_2OCH_2CH_2OAc$, 0.45 g, 1.68 mmol) and methanolic ammonia (100 mL, saturated at 0° C.) was stirred at room temperature for 18 h. Methanolic ammonia was evaporated in vacuo and the residue was purified by silica gel column (2×8 cm) chromatography. The column was flash eluted with dichloromethane containing 0–12% methanol. The homogeneous fractions were pooled and evaporated to yield 0.35 g (92%) of the title compound, mp 165–166° C. Ir (KBr): ν705 (=P-C), 1210 (-P=CH), 2930, 3050, and 3270 ($NH_2$, OH) $cm^{-1}$. Uv (pH 1): λmax254 nm (ε24,200), 282 (15,200), and 312 (5000); (MeOH): λmax266 nm (ε28,900), and 340 (2300); (pH 11): 266 nm (ε34,700), and 340 (1900); $^{31}$p nmr (DMSO-$d_6$): δ 65.85; $^1$H nmr (DMSO-$d_6$): δ 3.46 (m, 4 H, $2CH_2$), 4.70 (br s, 1 H, OH), 5.70 (s, 2 H, $CH_2$), 8.52 and 8.69 (2s, 2 H, $NH_2$), 8.65 (d, 1 H, $C_5H$), and 8.96 (d, 1 H, J=54 Hz, $C_2H$ ). Anal. Calcd. for $C_8H_{11}N_4O_2P \cdot 0.35$ $CH_2Cl_2$: C, 37.54; H, 4.61; N, 21.89. Found: C, 37.43; H, 4.13; N, 21.53.

Preparation of 7-Amino-1-[(1,3-dibenzoyloxy-2-propoxy)methyl]-1,3-azaphospholo [4,5-d]pyrimidine [compound 21, R=$CH_2OCH(CH_2OBz)_2$]

To a suspension of 7-amino-1H-1,3-azaphospholo[4,5-d] pyrimidine (compound 10, 0.5 g, 3.29 mmol) in DMF (20 mL) was added NaH (0.16 g, 4 mmol) under an argon atmosphere. After stirring the mixture at room temperature for 40 min, (1,3-dibenzoyloxy-2-propoxy)methyl bromide (109) (1.38 g, 3.5 mmol) was added and the reaction was continued for 18 h. The solvent was evaporated in vacuo. The residue was dissolved in dichloromethane (150 mL) and the organic solution was washed with water (30 mL). Aqueous layer was extracted with dichloromethane (2×100 mL) and the combined organic extracts were dried ($Na_2SO_4$) and evaporated. The residue was purified by silica gel column (2×15 cm) chromatography. The column was flash eluted with dichloromethane containing 0–2.5% methanol. The appropriate fractions containing the desired product were evaporated to yield 0.68 g (44%) of the title compound, mp 148–150° C. $^1$H nmr (DMSO-$d_6$): δ 4.35 (m, 3 H, CH, $CH_2$), 4.52 (m, 2 H, $CH_2$), 5.79 (s, 2 H, $CH_2$), 7.45–7.75 (m, 10 H, 2 Bz), 8.33 (s, 2 H, $NH_2$), 8.66 (d, 1 H, $C_5H$), and 8.81 (d, 1 H, J =57.9 Hz, $C_2H$ ). Anal. Calcd. for $C_{23}H_{21}N_4O_5P$: C, 59.48; H, 4.56; N, 12.07. Found: C, 59.08; H, 4.56; N, 12.02.

Preparation of 7-Amino-1-[(1,3-dihydroxy-2-propoxy)methyl]-1, 3-azaphospholo [4,5-d]pyrimidine [compound 21, R=$CH_2OCH(CH_2OH)_2$]

A mixture of 7-amino-1-[(1,3-dibenzoyloxy-2-propoxy)methyl]-1,3-azaphospholo[4,5-d]pyrimidine (compound 21, R=$CH_2OCH(CH_2OBz)_2$, 0.65 g, 1.4 mmol) and methanolic ammonia (125 mL, saturated at 0° C.) was stirred at room temperature for 20 h. The solvent was evaporated under reduced pressure. The solid thus obtained was triturated with cold methanol (5 mL) and the product was collected by filtration. To the filtrate silica gel was added and the solvent was evaporated. The dry powder was loaded on top of a silica gel column (2×8 cm). The column was flash eluted with dichloromethane containing 0–25% methanol to give 0.28 g (78%) of the title compound, mp 180–182° C. Ir (KBr): ν695 (=P-C), 1215 (-P=CH), and 3060, 3300, 3380 and 3500 ($NH_2$, OH) $cm^{-1}$. Uv (pH 1): λmax254 nm (ε19,000), 282 (12,100), and 314 (4000); (MeOH): λmax266 nm (ε24,700), and 336 (24,000); (pH 11): 266 nm (ε27,650), and 340 (1900). $^{31}$p nmr (DMSO-$d_6$): δ 65.02. $^1$H nmr (DMSO-$d_6$): δ 3.43 (m, 3 H, CH, $CH_2$), 3.53 (m, 2 H, $CH_2$), 4.63 (br s, 2 H, 2OH), 5.68 (s, 2 H, $CH_2$), 8.23 (s, 2 H, $NH_2$), 8.53 (d, I H, $C_5H$), and 8.82 (d, 1 H, J =58.5 Hz, $C_2H$ ). Anal. Calcd. for $C_9H_{13}N_4O_3P$: C, 42.19; H, 5.11; N, 21.87. Found: C,42.37; H, 5.12; N, 21.66.

Preparation of 7-Amino-1-(2,3,5-tri-O-benzoyl-β-D-ribofuranosyl)-1,3-aza-phospholo[4,5-d]pyrimidine [compound 21, R=2,3,5-tri-O-benzoyl-β-D-ribofuranose]

A mixture of 7-amino-1H-1,3-azaphospholo[4,5-d] pyrimidine (compound 10, 0.3 g, 1.97 mmol) in 1,1,1,3,3, 3-hexamethyldisilazane (HMDS, 5 mL), pyridine (5 mL) and ammonium sulfate (50 mg) was heated under reflux for 18 h. The reaction mixture was allowed to cool to room temperature and the excess of HMDS and pyridine were evaporated in vacuo. The silyl derivative of compound 10 was dried under high vacuum for 3 h. The dried material was dissolved in 1,2-dichloroethane (30 mL) to which 1-O-acetyl-2,3,5-tri-O-benzoyl-D-ribofuranose (1.28 g, 2.4 mmol) was added. The mixture was cooled in an ice bath. A solution of $SnCl_4$ in dichloromethane (1 M, 2.8 mL, 2.8 mmol) was added keeping the flask under an argon atmosphere. After stirring the mixture in the ice bath for 4 h, the ice bath was removed and the reaction was continued at ambient temperature for 18 h. Methanol (10 mL) was added and after 10 min it was diluted with dichloromethane (100 mLL). The organic layer was washed with saturated sodium hydrogen carbonate solution (50 mL) and the resultant emulsion was filtered through a Celite pad. Organic layer was separated and the aqueous layer was extracted with dichloromethane (2×50 mL). The combined organic layer was dried ($Na_2SO_4$) and evaporated. The solid thus obtained was crystallized from a mixture of ethyl acetate and methanol to give 0.65 g (56%) of the title compound, mp 248–250° C. (dec). $^1$H nmr (DMSO-$d_6$): δ 4.85(m,2 t $C_5$ $H_2$), 4.96 (m, 1 H, $C_4'H$), 6.01 (m, 1 H, $C_3'H$), 6.19 (m, 1 H, $C_2'H$), 6.51 (d, 1 H, $C_1'H$), 7.44–8.05 (m, 15 H, 3Bz), 8.44 and 8.47 (2s, 2 H, $NH_2$), 8.75 (d, 1 H, $C_5H$), and 8.95 (d, 1 H, J =57 Hz, $C_2H$). Anal. Calcd. for $C_{31}H_{25}N_4O_7P \cdot 0.5$ $H_2O$: C, 61.49; H, 4.33; N, 9.25. Found: C, 61.61; H, 3.88; N, 9.21.

Preparation of 7-Amino-1-(β-D-ribofuranosyl)-1,3-azaphospholo-[4,5-d]pyrimidine (compound 21, R=β-D-ribofuranose)

A mixture of 7-Amino-1-(2,3,5-tri-O-benzoyl-β-D-ribofuranosyl)-1,3-azaphospholo[4,5-d]pyrimidine (compound 21 , R=2,3,5-tri-O-benzoyl-β-ribofuranose, 0.45 g, 0.75 mmol) and methanolic ammonia (100 mL, saturated at 0° C.) was stirred at room temperature for 20 h and the methanolic ammonia was evaporated under reduced pressure. The residue was triturated with methanol (10 mL) and the product was collected by filtration. The filtrate was evaporated and the residue was purified by chromatography over a silica gel column. The column was flash eluted with dichloromethane containing 0–20% methanol. The appropriate fractions containing the pure product were collected and evaporated to give a total yield of 0.18 g (84%) of the title compound, mp 220–222° C. Ir (KBr): ν700 (=P-C), 1205 (-P=CH), and 2930–3470 (NH$_2$, OH) cm$^{-1}$. Uv (pH 1): λmax254 nm (ε23,400), 284 (15,600), and 314 (5600); (MeOH): λmax266 nm (ε32,900), and 340 (2100); (pH 11): 266 nm (ε36,050), and 338 (3250). $^{31}$p nmr (DMSO-d$_6$): δ 62.50; $^1$H nmr (DMSO-d$_6$): δ3.73(dd,2H, C$_5$H$_2$), 3.98 (m, 1 H, C$_4$H), 4.10 (br s, 1 H, C$_3$H), 4.28 (m, 1 H, C$_2$H), 5.24 (br s, 2 H, 2OH), 5.63 (br s, 1 H, OH), 5.70 (d, 1 H, C$_1$H), 8.24 (s, 2 H, NH$_2$), 8.86 (d, 1 H, C$_5$H), and 8.83 (d, 1 H, J =58.8 Hz, C$_2$H). Anal. Calcd. for C$_{10}$H$_{13}$N$_4$O$_4$P.0.25 CH$_2$Cl$_2$:C, 40.30; H, 4.45; N, 18.35. Found: C, 40.40; H, 4.15; N, 18.54.

Preparation of 7-Amino-1-(2-deoxy-3,5-di-O-p-toluoyl-β-D-erythro-pento-furanosyl)-1,3-azaphospholo[4,5-d]pyrimidine [compound 21, R=2-deoxy-3,5-di-O-p-toluoyl-β-D-erythro-pentofuranose]

7-Amino-1H-1,3-azaphospholo[4,5-d]pyrimidine (compound 10, 0.5 g, 3.29 mmol, dried by coevaporation with dry DMF, 35 mL) was suspended in dry acetonitrile (30 mL) to which sodium hydride (160 mg, 4 mmol, 60% dispersion in mineral oil) was added under an argon atmosphere. The mixture was stirred at room temperature for 40 min and 1-chloro-2-deoxy-3,5-di-O-p-toluoyl-α-D-erythro-pentofuranose (110) (1.55 g, 4 mmol) was added. The reaction mixture was stirred for 2.5 h and the solvent was evaporated. The residue was partitioned between dichloromethane (150 mL) and water (50 mL). Aqueous layer was separated and extracted with dichloromethane (2×100 mL). The combined organic extracts were dried (Na$_2$SO$_4$) and evaporated. The residue was purified by chromatography over a silica gel column (2×20 cm). The column was flash eluted with dichloromethane containing 0–2% methanol. The fractions containing the desired product were collected and evaporated to yield 0.8 g (48%), mp 128–130° C. $^1$H nmr (DMSO-d$_6$): δ2.33and 237 (2s, 6 H, 2CH$_3$), 2.90 (m, 1 H, C$_2$H), 3.03 (m, 1 H, C$_2$·H), 4.70 (m, 3 H, C$_4$H and C$_5$H$_2$), 5.64 (m, 1 H, C$_3$H), 6.39 (t, 1 H, C$_1$H), 7.24 and 7.34 (2d, 4 H, Tol), 7.80 and 7.90 (2d, 4 H, Tol), 8.33 (s, 2 H, NH$_2$), 8.33 (d, 1 H, C$_5$H), and 8.85 (d, 1 H, J =59 Hz, C$_2$H). Anal. Calcd. for C$_{26}$H$_{25}$N$_4$O$_5$P: C, 61.90; H, 5.00; N, 11.11. Found: C, 61.57; H, 5.21; N, 10.76.

Preparation of 7-Amino-1-(2-deoxy-β-D-eythro-pentofuranosyl)-1,3-azaphospholo[4,5-d]pyrimidine [compound 21, R=2-deoxy-β-D-erythro-pentofuranose]

A mixture of 7-amino-1-(2-deoxy-3,5-di-O-p-toluoyl-β-D-erythro-pentofuranosyl)-1,3-azaphospholo[4,5-d]pyrimidine (compound 21, R=2-deoxy-3,5-di-O-p-toluoyl-β-D-erythro-pentofuranose, 0.6 g, 1.19 mmol) and methanolic ammonia (100 mL, saturated at 0° C.) was stirred at room temperature for 20 h in a pressure bottle. The reaction flask was cooled in an ice bath, carefully opened and evaporated to dryness. The residue was dissolved in methanol (10 mL) and impregnated onto silica gel (10 g). The solvent was evaporated and the dry powder was loaded on a silica gel column (2×10 cm). The column was flash eluted with dichloromethane containing 0–12% methanol to yield 0.24 g (75%) of the title compound, mp 132° C. (foams). Ir (KBr): ν700 (=P-C), 1210 (-P=CH), and 2930–3320 (NH$_2$, OH) cm$^{-1}$. Uv (pH 1): λmax254 nm (ε45,238), 282 (25,800), and 314 (10,100); (MeOH): λmax266 nm (ε59,900), and 330 (5050); (pH 11): 266 nm (ε65,150), and 334 (5400). $^{31}$p nmr (DMSO-d$_6$): δ 62.19. $^1$H nmr (DMSO-d$_6$): δ 2.40 (m, 2 H, C$_2$H and C$_2$·H), 3.65 (m, 2 H, C$_5$H$_2$), 3.96 (m, 1 H, C$_4$·H), 4.32 (br s, 1 H, C$_3$H), 5.16 (br s, 1 H, OH), 5.40 (br s, 1 H, OH), 6.14 (t, 1 H, C$_1$H), 8.35 (s, 2 H, NH$_2$), 8.81 (d, 1 H, C$_5$H), and 8.88 (d, 1 H, J =57.3 Hz, C$_2$H). Anal. Calcd. for C$_{10}$H$_{13}$N$_4$O$_3$P.0.25 CH$_2$Cl$_2$: C, 42.53; H, 4.70; N, 19.36; P, 10.70. Found: C, 42.08; H, 4.75; N, 19.11; P, 10.28.

EXAMPLE 10

Similar to the 1,3-azaphospholo[4,5-d]pyrimidine chemistry as outlined in examples 1–9, 1,3-azaphospholo[5,4-d] pyrimidines are made from properly functionalized oxazoles. The key starting material for this purpose is ethyl oxazole-4-carboxylate (compound 22), which is prepared as reported (52). Bromination of compound 22 with one equivalent of N-bromosuccinimide in the presence of 1,1'-azobis(cyclohexanecarbonitrile) in CCl$_4$ gives the corresponding 5-bromo derivative (compound 23). It has been found (53–55) that the nuclear bromination of oxazoles either with bromine or with N-bromosuccinimide occurs preferentially at C-5; if this position is occupied, then at C-4, but not at C-2. Selective ammonolysis of compound 23 with methanolic ammonia (saturated at 0° C.) at controlled temperature yields 5-bromo-1,3-oxazole-4-carboxamide (compound 24).

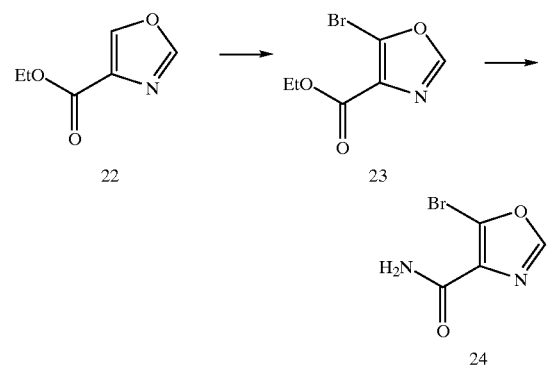

EXAMPLE 11

Synthesis of 4-Bromo-1H-1,3-azaphospholine-5-carbonitrile (compound 26)

Dehydration of compound 24 with phosgene provides 5-bromoxazole-4-carbonitrile (compound 25), which on treatment with TTP in the presence of naked fluoride ion (18-crown-6/KF) in anhydrous toluene at reflux temperature provides 4-bromo-1H-1,3-azaphospholine-5-carbonitrile (compound 26).

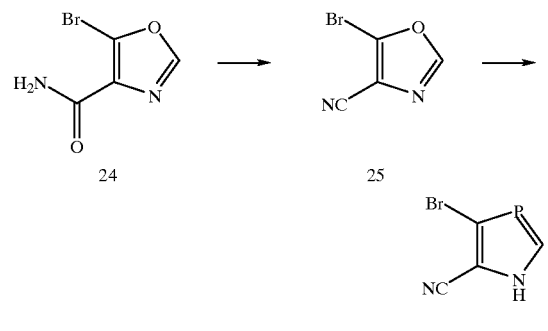

This O→P conversion also undergoes a ring-opening and recyclization mechanism as described in example 1 (compound 9).

EXAMPLE 12

Synthesis of 5-Amino-1H-1,3-azaphospholine-4-carbonitrile (compound 28)

Hydrolysis of compound 26 with aqueous NaOH at room temperature gives 4-bromo-1H-1,3-azaphospholine-5-carboxamide (27a). The $C_4$-Br of 27a may not be quite reactive toward conventional nucleophilic displacement reactions. However, the use of copper compounds as catalysts in nucleophilic aromatic (56, 57) and heteroaromatic (58) substitution reactions are known. Thus, treatment of compound 27a with CuCN in the presence of copper powder or CuCl at elevated temperature gives the cyano compound 27b. Decarbonylation of compound 27b under Hofman conditions (NaOBr) provides 5-amino-1H-1,3-azaphospholine-4-carbonitrile (compound 28).

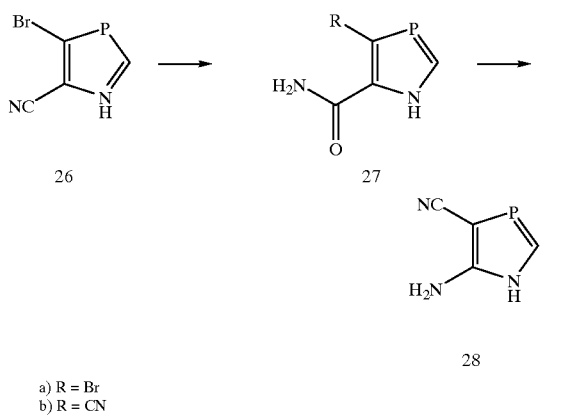

a) R = Br
b) R = CN

EXAMPLE 13

Synthesis of 4-Amino-1H-1,3-azaphospholo[5,4-d]pyrimidine (Adenine Analog, compound 29)

5-Amino-1H-1,3-azaphospholine-4-carbonitrile (compound 28) is reacted with formamidine acetate in ethanol at reflux temperature to form the ring annulated product 4-amino-1H-1,3-azaphospholo[5,4-d]pyrimidine (the adenine congener, compound 29).

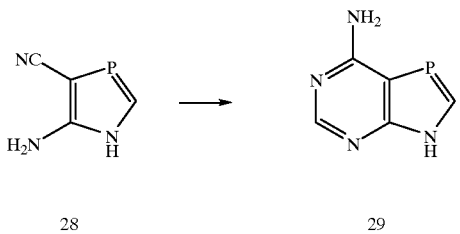

EXAMPLE 14

Synthesis of N-1 substituted 4-amino-1-1,3-azaphospholo[5,4-4-d]pyrimidines

A further embodiment includes phosphazole compounds having the structure:

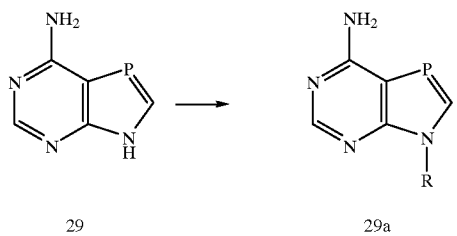

wherein R is

—$(CH_2)_4CH_3$
—$(CH_2)_5CH_3$
—$CH_2CH\!=\!CH_2$
—$CH_2CH\!=\!CHCH_2CH_3$ (cis and trans)
—$CH_2CH\!=\!CHCH_2P(OH)_2$ (cis and trans)
—$CH_2CH\!=\!C(CH_3)_2$
—$(CH_2)_3CH_2OH$
—$CH_2CH\!=\!CHCH_2OH$

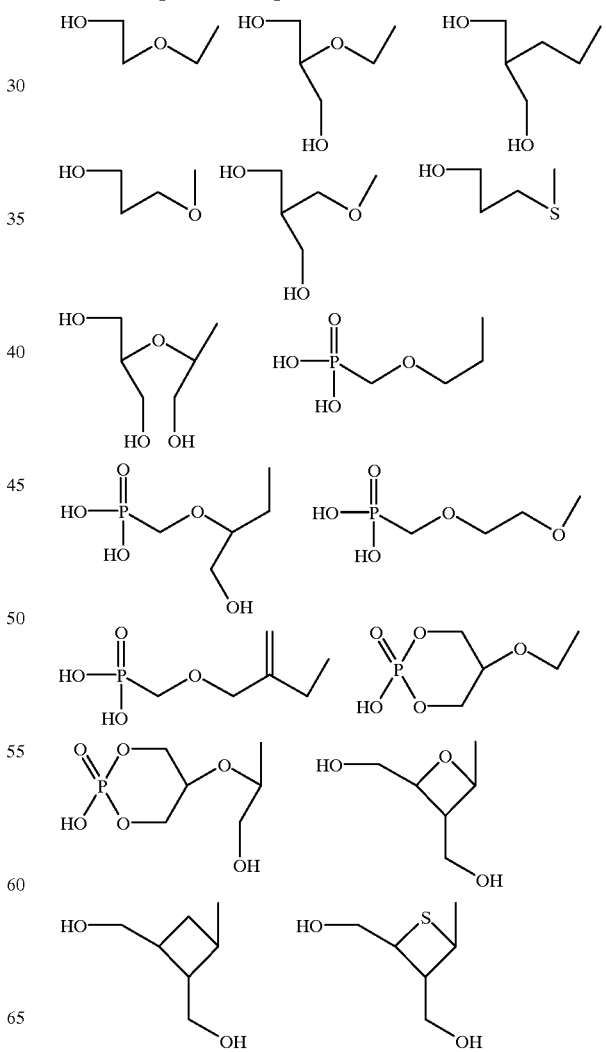

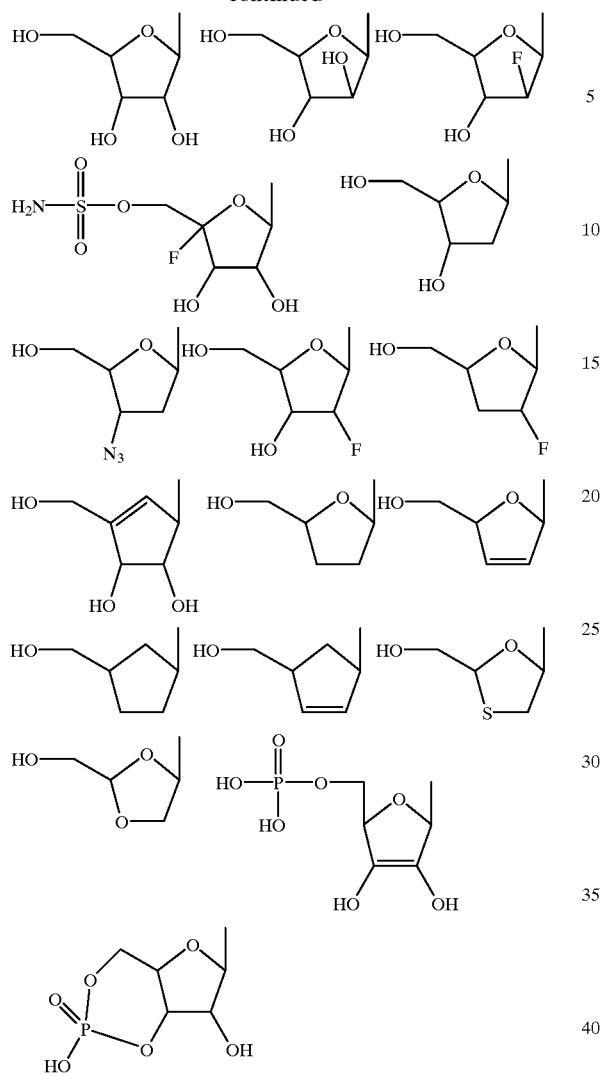

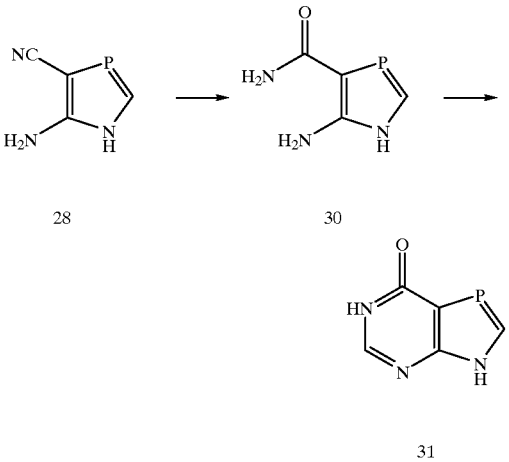

when fused with formamidine forms the hypoxanthine analog, compound 31.

The synthesis of the compounds in Example 14 proceeds by the direct alkylation of the adenine analog (compound 29) with requisite alkyl halides or properly protected glycosyl halides in appropriate solvents. In the case of glycosyl derivatives, subsequent deprotection of the glycosylated product under alkaline conditions is required. Phosphorylation of the unprotected adenosine analog with $POCl_3$ in trimethylphosphate, according to the general procedure of Yoshikawa et al. (59) gives the corresponding 5'-monophosphate, which when reacted with N,N'-dicyclohexylcarbodiimide (DCC) in anhydrous pyridine in the presence of 4-morpholino-N,N'-dicyclohexylcarboxamidine under high-dilution conditions (60) provides the cAMP analog 7-amino-3-(β-D-ribofuranosyl)-1,3-azaphospholo[5,4-d]pyrimidine 3',5'-cyclic phosphate.

EXAMPLE 15

Synthesis of 1,3-Azaphospholo[5,4-d]pyrimidin-4(1H,5H)-one (Hypoxanthine Analog, compound 31)

Hydrolysis of the nitrile function of 5-amino-1H-1,3-azaphospholine-4-carbonitrile (compound 28), from Example 12, is carried out by treatment with 0.1N aqueous NaOH at gentle reflux for 5 hours to obtain 5-amino-1H-1,3-azaphospholine-4-carboxamide (compound 30), which when fused with formamidine forms the hypoxanthine analog, compound 31.

EXAMPLE 16

Synthesis of 1,3-Azaphospholo[5,4-d]pyrimidine-4,6(1H,5H,7H)-dione (Xanthine Analog, compound 32)

5-Amino-1H-1,3-azaphospholine-4-carboxamide (compound 30 from Example 15) is fused with urea at 160° C. for 45 min to obtain the xanthine analog 32.

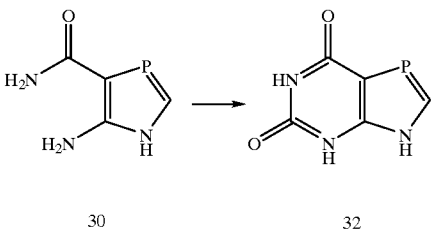

EXAMPLE 17

Synthesis of 1,3-Azaphospholo[5,4-d]pyrimidine-4(1H,5H)-thione (6-Thiopurine analog, compound 34).

The hypoxanthine analog (compound 31 from Example 15) is reacted with $POCl_3$ in the presence of diethylaniline at reflux temperature for 1 hour to form 4-chloro-1H-1,3-azaphospholo[5,4-d]pyrimidine (compound 33), which on reaction with thiourea in boiling ethanol produces the 6-thiopurine analog (compound 34).

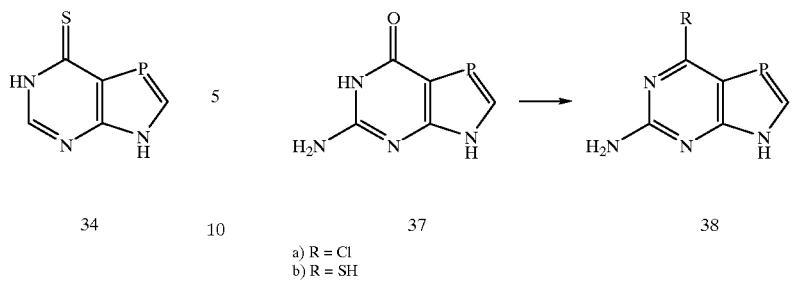

a) R = Cl
b) R = SH

EXAMPLE 18

Synthesis of 6-Amino-1,3-azapholo[5,4-d]pyrimidin-4 (1H,5H)-one (Guanine Analog, compound 37).

The guanine analog (compound 37) is obtained from compound 30 (from Example 15) by reacting with benzoyl-isothiocyanate to form 5-(N'-benzoylthiocarbonyl)amino-1H-1,3-azaphospholine-4-carboxamide (compound 35), which when reacted with $CH_3I$ in 0.1 N NaOH will afford 5-(N'-benzoyl-S-methylisothiocarbamoyl)amino-1H-1,3-azaphospholine-4-carboxamide (compound 36), which, in the presence of ammonia, produces the guanine congener (compound 37).

EXAMPLE 20

Synthesis of N-1 substituted 6-Amino-1,3-azaphospholo[5,4-d]-pyrimidine-4 (1H, 5H) -ones A further embodiment includes phosphazole compounds having the structure:

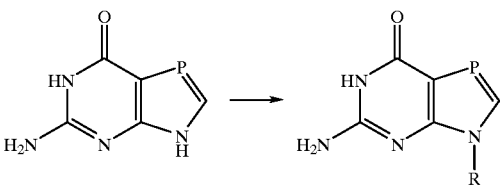

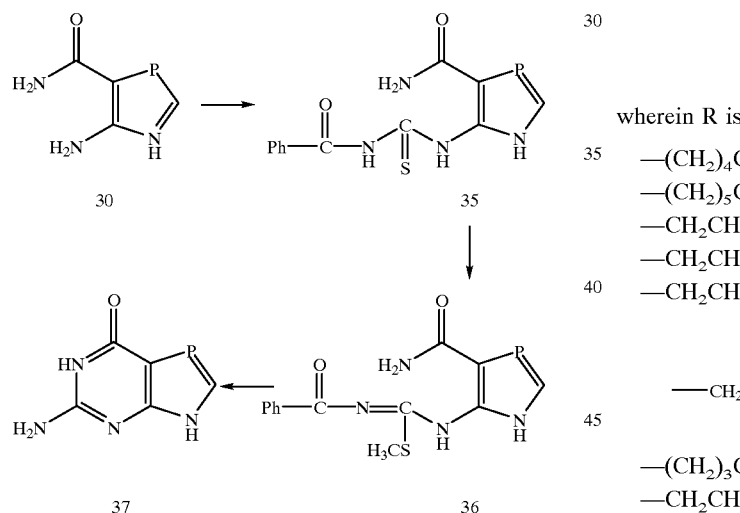

wherein R is

—$(CH_2)_4CH_3$
—$(CH_2)_5CH_3$
—$CH_2CH$=$CH_2$
—$CH_2CH$=$C(CH_3)_2$
—$CH_2CH$=$CHCH_2CH_3$

—$CH_2CH$=$CHCH_2P(OH)_2$ (with =O)

—$(CH_2)_3CH_2OH$
—$CH_2CH$=$CHCH_2OH$

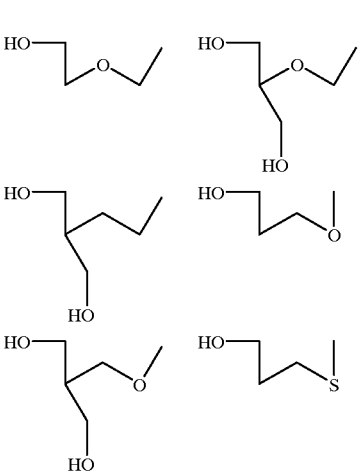

EXAMPLE 19

Synthesis of 6-Amino-1,3-azaphospholo[5,4-d] pyrimidine-4(1H, 5H)-thione (6-Thioguanine Analog, compound 38b)

The guanine congener from Example 18 (compound 37) on heating under 5 reflux with $POCl_3$ in the presence of diethylaniline provides 6-amino-4-chloro-1H-1,3-azaphospholo[5,4-d]pyrimidine (compound 38a), which on reaction with thiourea in boiling ethanol produces the 6-thioguanine anlaog 6-amino-1,3-azaphospholo[5,4-d] pyrimidine-4(1H, 5H)-thione (compound 38b).

-continued

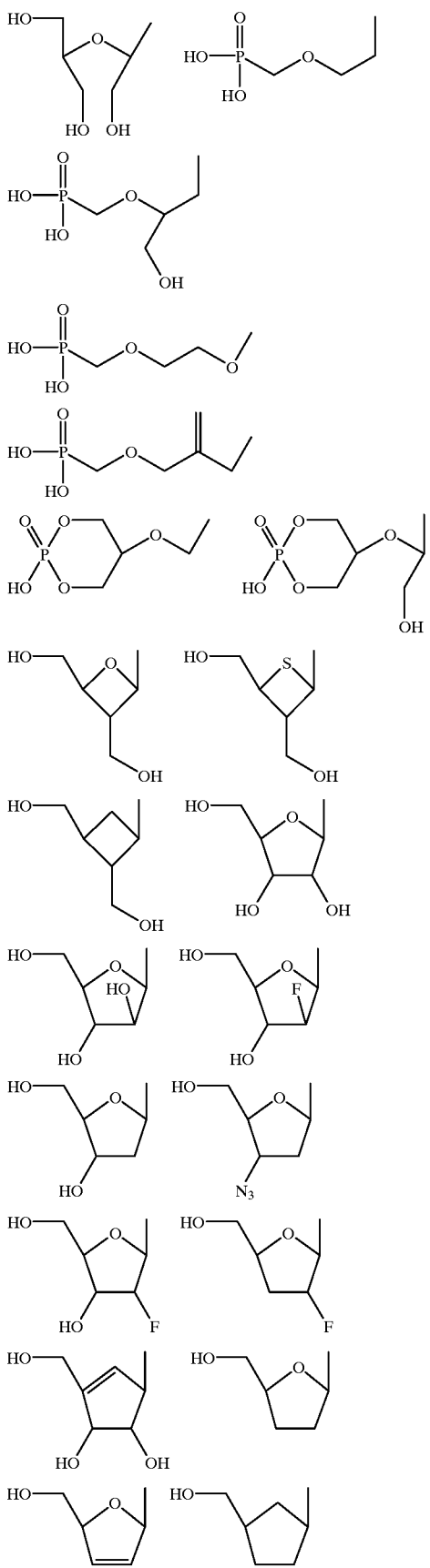

-continued

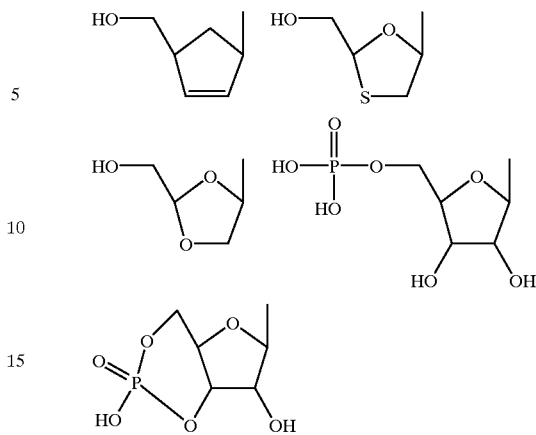

The synthesis of the compounds in Example 20 proceeds by the direct alkylation of the guanine analog (compound 37) with requisite alkyl halides or properly protected glycosyl halides in appropriate organic solvents. In the case of glycosyl derivatives, subsequent deprotection of the protected glycosylated product under alkaline conditions is required. Phosphorylation of the unprotected guanosine analog with $POCl_3$ in trimethylphosphate (59) produces the corresponding 5'-monophosphate, which when dehydrated with DCC in anhydrous pyridine under high-dilution conditions (60) provides the cGMP analog.

EXAMPLE 21

P-Substituted 7-Amino-3H-1,3-azaphospholo[4,5-d] pyrimidines

A further embodiment includes phosphazole compounds having the structure:

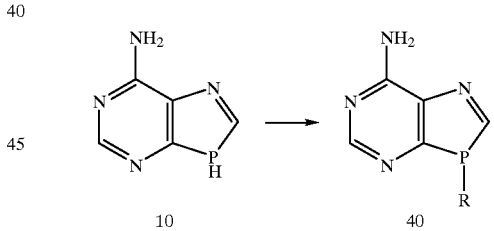

wherein R is

—$CH_2CH=CH_2$
—$CH_2CH=C(CH_3)_2$
—$CH_2CH=CHCH_2OH$
—$CH_2CH=CHCH_2CH_3$

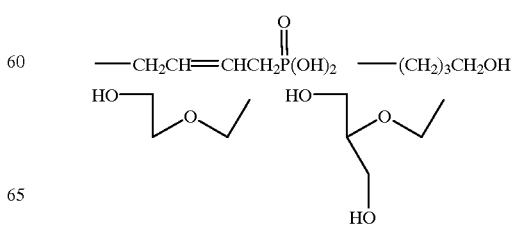

-continued

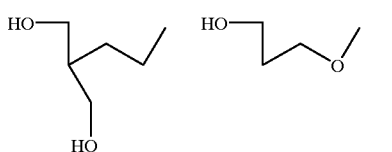
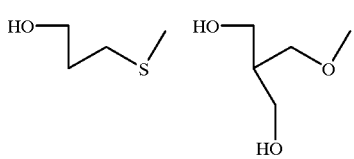
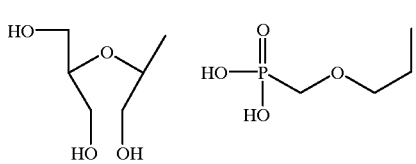
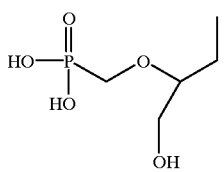
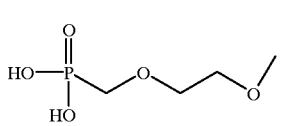
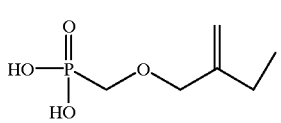
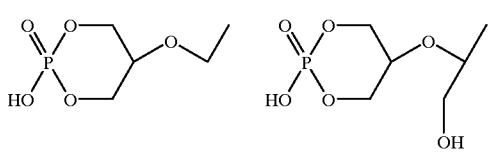
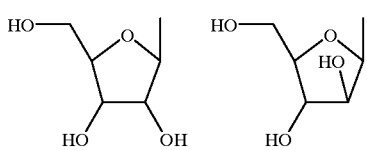
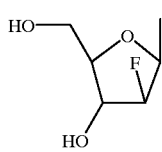

-continued

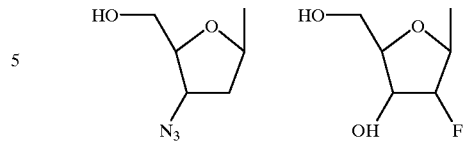
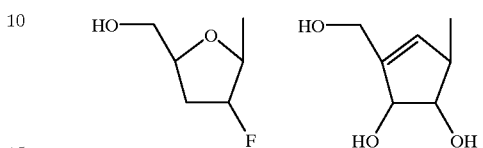
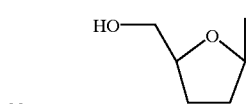
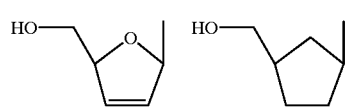
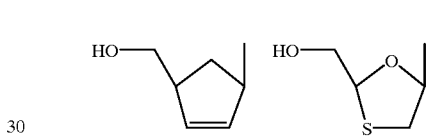
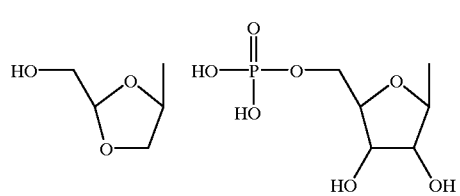

The synthesis of the compounds in Example 21 proceeds by the direct alkylation of the adenine analog (Example 2, compound 10) with requisite alkyl halides or properly protected glycosyl halides in the presence of the Phase-Transfer catalyst cryptand tris-[2-(2-methoxyethoxy)ethyl] amine (TDA-1) and solid KOX in acetonitrile.

EXAMPLE 22

P-Nucleoside structurally related to Adenosine (compound 44)

Compounds in Example 22 are prepared as follows:

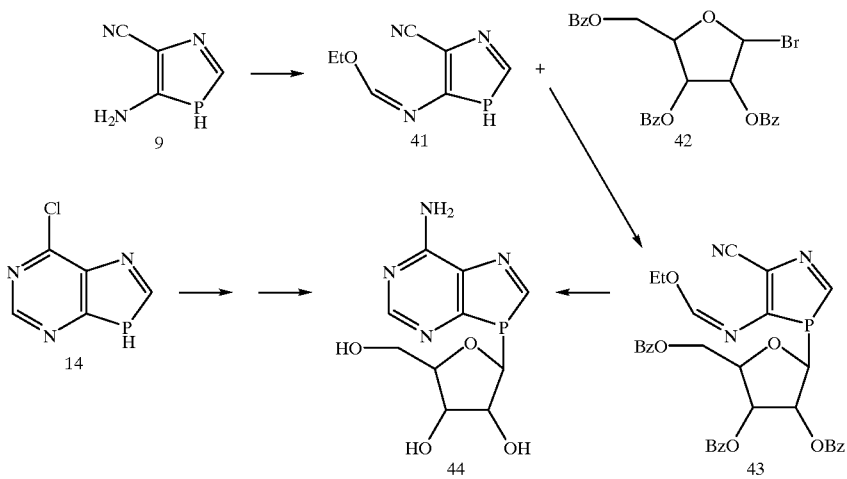

For the synthesis of the target adenosine analog (compound 44), compound 9 serves as a useful starting material. The protection of the amino group is effected by the treatment of compound 9 with diethoxymethylacetate in acetonitrile to give 4-ethoxymethyleneamino-1,3-azaphospholine-5-carbonitrile (compound 41). Coupling of compound 41 with 2,3,5-tri-O-benzoyl-D-ribofuranosyl bromide (compound 42) (61) provides the corresponding P-nucleoside (compound 43). Compound 43 is also prepared by alkylation of compound 41 with compound 42 in the presence of lithium dusopropylimide (LDA) in a nonpolar solvent at −70° C. This synthetic route is similar to the one used for P-alkylation of 1,3-azaphospholines (62). Compound 43 on reaction with methanolics ammonia (saturated at 0° C.) at room temperature for 24 hours, deprotection of the sugar moiety with concomitant ring cyclization occurs to give the adenosine analog 7-amino-3-(β-D-ribofuranosyl)-1,3-azaphospholo[4,5-d]pyrimidine (compound 44). Compound 44 is also prepared by the direct glycosylation of the sodium salt of compound 14 (generated in situ by the treatment with NaH in CH₃CN) with 2,3-O-isopropylidene-5-O-tert-butyldimethylsilyl)-α-D-ribofuranosyl chloride (63) in acetonitrile at room temperature to produce the P-glycosylated product (along with N-glycosylated product), which on separation by flash silica gel column chromatography and deisopropylidenation with aqueous trifluoroacetic acid followed by amination provides compound 44.

EXAMPLE 23

2'-Deoxy and Arabinofuranosyl derivatives of compound 10

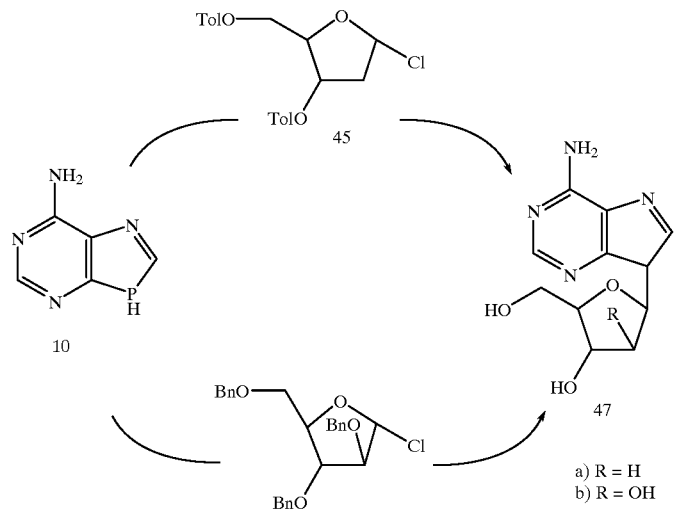

a) R = H
b) R = OH

P-Nucleosides of example 23 (compound 47) are readily accessible by substituting the substrate 42 with the α-halogenoses 45 and 46 in the glycosylation of compound 10. Both compounds 45 and 46 are prepared by the literature procedures (64, 65). Structural manipulation of the protected azaphosphole nucleosides thus obtained provides the target nucleosides 47.

EXAMPLE 24

5'-Monophosphate (compound 48) and 3',5'-cyclic phosphate (compound 49) of Adenosine analog, compound 44

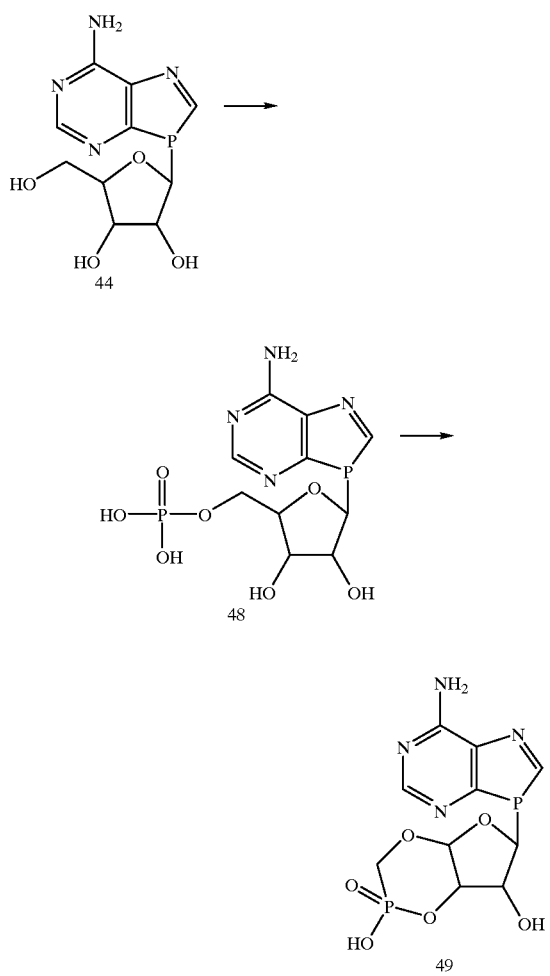

The direct utilization of certain cyclic nucleotide derivatives as medicinal agents is well documented (27). With a view of gaining greater tissue specificity and longer lasting potency over CAMP, the 3',5'-cyclic phosphate of compound 44 will be prepared via the intermediate compound 48. Phosphorylation of unprotected adenosine analog 44 with POCl₃ in trimethylphosphate, according to the general procedure of Yoshikawa and coworkers (59) will provide the corresponding 5'-monophosphate (compound 48). Compound 48 is reacted with N,N'-dicyclohexylcarbodiimide (DCC) in anhydrous pyridine in the presence of 4-morpholino-N,N'-dicyclohexylcarboxamidine under high-dilution conditions (60) to obtain 7-amino-3-(β-D-ribofuranosyl)-1,3-azaphospholo[4,5-d]- pyrimidine 3',5'-cyclic phosphate (compound 49).

EXAMPLE 25

P-Glycosylated Inosine/Thioinosine Analogs (compound 51)

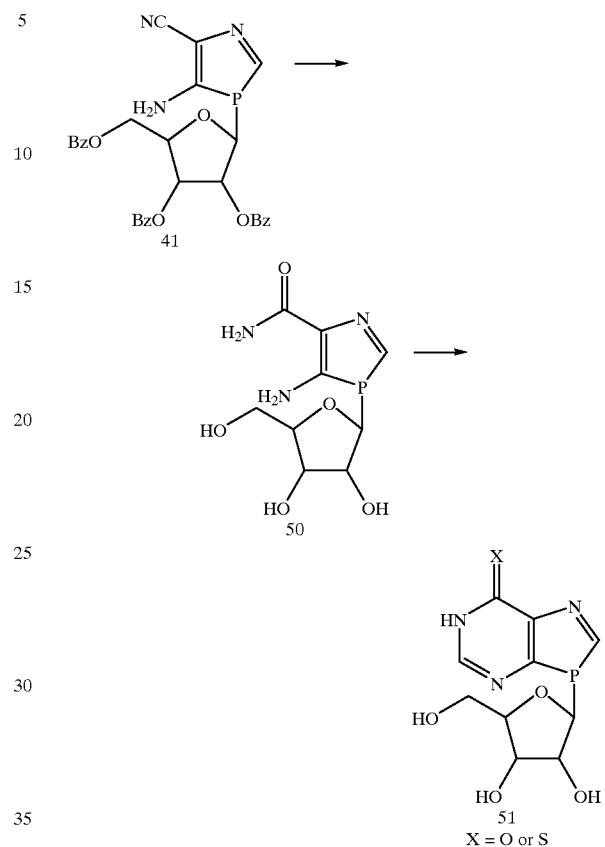
X = O or S

Concomitant hydrolysis of the nitrile function and the sugar protecting groups of compound 41 is carried out by the treatment with 0.1N NaOH solution to obtain 4-amino-3-(β-D-ribofuranosyl)-1,3-azaphospholine-5-carboxamide (compound 50). Compound 50 is ring closed with formamide or with triethyl orthoformate to obtain the inosine analog, compound S1 (X=O), which is also prepared by deamination of the adenosine analog, compound 44, with aqueous nitrous acid. Acetylation of the sugar hydroxyls with acetic anhydride/4-(dimethylamino)pyridine, followed by thiation with phosphorus pentasulfide and subsequent deacetylation provides the 6-thioinosine analog 3-(β-D-ribofuranosyl)- 1,3-azaphospholo[4,5-d]pyrimidine-7(6H)-thione (compound 51, X=S).

EXAMPLE 26

P-Glycosylated Guanosine Analog (compound 54)

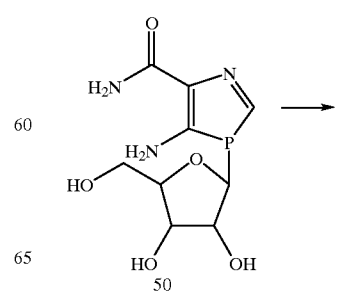

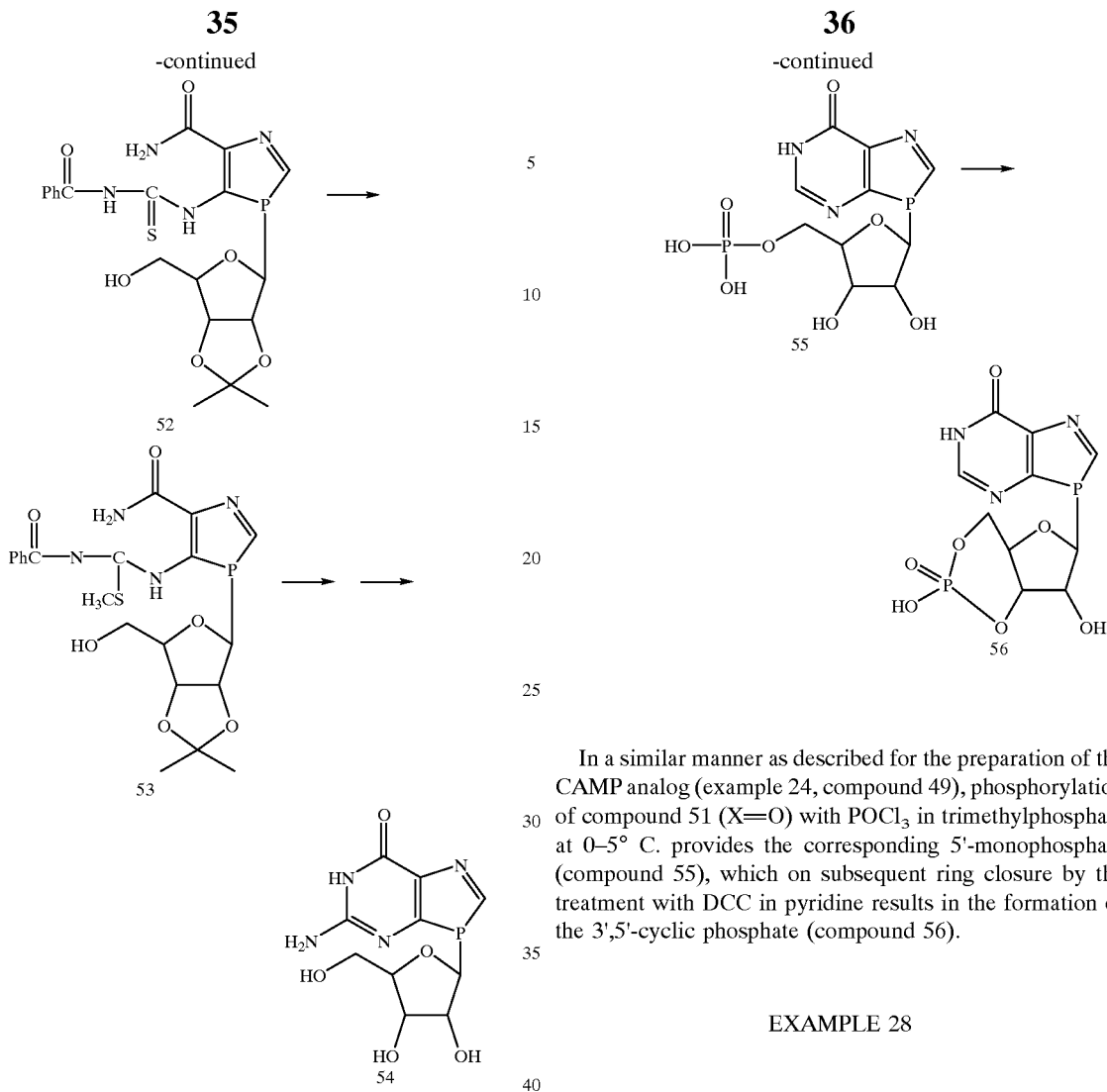

In a similar manner as described for the preparation of the guanine analog (compound 37, example 18), nucleoside 50 is ring-closed to the guanosine analog 5-amino-3-(β-D-ribofuranosyl)-1,3-azaphospholo[4,5-d]pyrimidin-7(6H)-one (compound 54), via the 4-thioureido intermediate (52).

EXAMPLE 27

5'-Monophosphate (compound 55) and 3',5'-cyclic phosphate (compound 56) of Inosine Analog (compound 51, X=O)

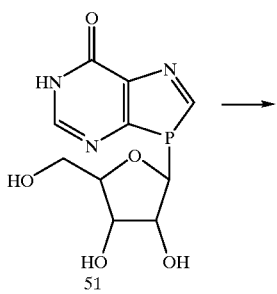

In a similar manner as described for the preparation of the cAMP analog (example 24, compound 49), phosphorylation of compound 51 (X=O) with POCl₃ in trimethylphosphate at 0–5° C. provides the corresponding 5'-monophosphate (compound 55), which on subsequent ring closure by the treatment with DCC in pyridine results in the formation of the 3',5'-cyclic phosphate (compound 56).

EXAMPLE 28

5'-Monophosphate (compound 57) and 3',5'-cyclic phosphate (compound 58) of Guanosine Analog (compound 54)

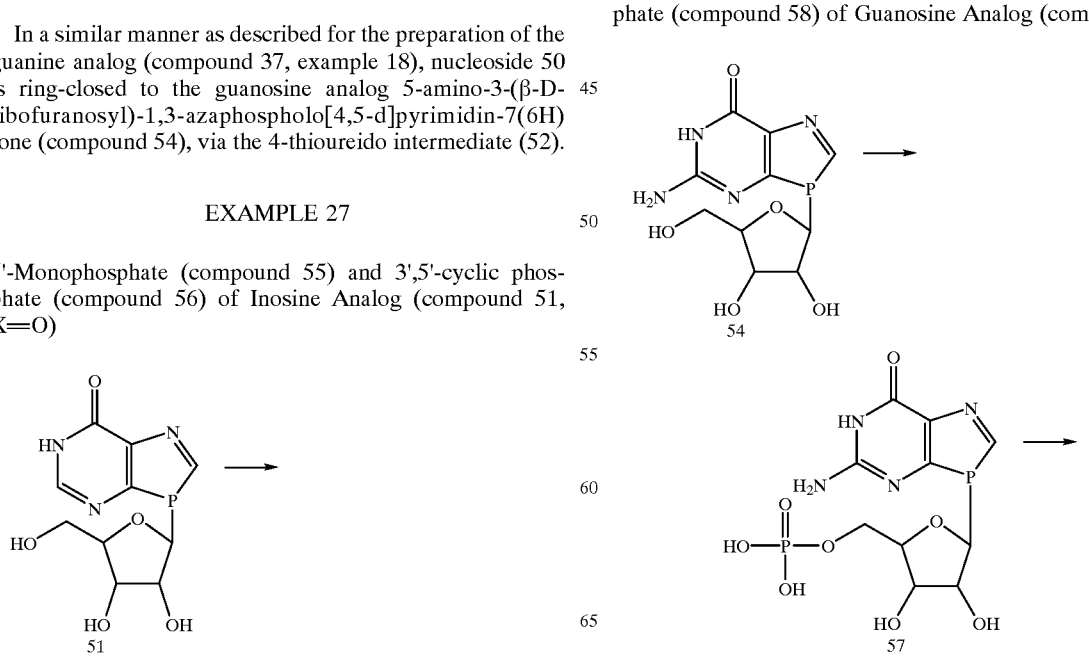

-continued

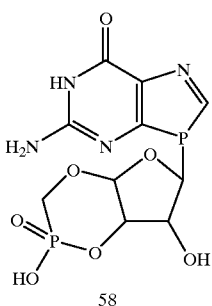

58

In a similar manner as described for the preparation of the cAMP analog (example 24, compound 49), phosphorylation of the guanosine analog (compound 54) provides the corresponding 5'-monophosphate (compound 57), which on ring closure with DCC/pyridine results in the cGMF analog (compound 58).

EXAMPLE 29

5-Amino-3- (2 ,3-dideoxy-β-D-glycero-pentofuranosyl)-1,3-azaphospholo[4,5]- pyrimidin-7(6-one (compound 61)

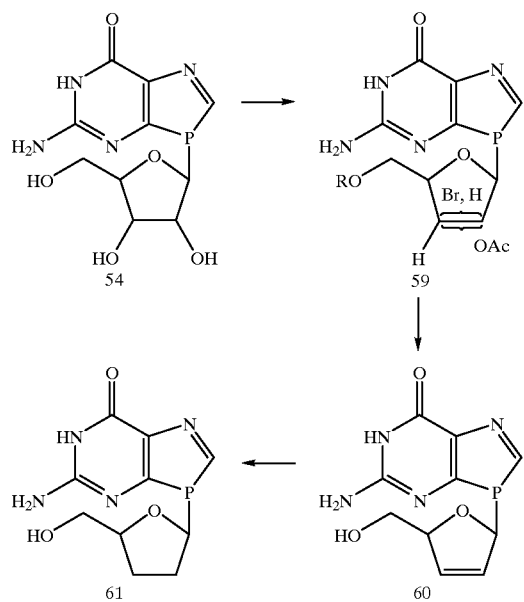

The chemical synthesis of compound 61 is accomplished by the following sequence of reactions. Treatment of the guanosine analog (compound 54) with α-acetoxyisobutyryl bromide in moist acetonitrile (66, 67) results in the formation of a mixture of 2'(3')-bromo-3'(2')-O-acetyl nucleosides (compounds 59). Treatment of compounds 59 with a mixture of zinc-copper in DMF (67), followed by deprotection gives 5-amino-3-(2,3-dideoxy-β-D-glycero-pent-2-enofuranosyl)-1,3-azaphospholo[4,5-d]pyrimidine-7(6H)-one (compound 60). Catalytic hydrogenation (Pd/C, $H_2$) of compound 60 will afford compound 61.

II. Synthesis of Deazaphosphazoles (Phospholo[2,3-d]pyrimidines) and Their Nucleosides Since the isolation of the antibiotics tubercidin, toyocamycin and sangivamycin in the early 1960's and subsequent structural elucidation of these antibiotics as pyrrolo[2,3-d]pyrimidine nucleosides, the developments in 7-deazapurine nucleosides are phenomenal (68). Isolation of additional 7-deazapurine nucleosides from natural sources in recent years, such as nucleoside Q (69–72), cadeguomycin (73–77), antibiotic AB-116 (78, 79), dapiramicin (80–82), 5-iodo-5'-deoxytubercidin (83), kanagawamicin (79), and mycalisines A and B (84,85) has generated tremendous interest in the synthesis of deazapurine nucleosides. A large number of these nucleosides exhibited significant antiviral and antitumor activities (68, 86, 87) in vitro as well as in vivo. Therefore, the synthesis of the phosphorus congeners of certain of these antibiotics was undertaken.

The synthesis of these compounds in this totally unexplored area uses essentially the same synthetic sequences that were used for the preparation of 1,3-azaphospholo[4,5-d]primidines. The rudimentary 5-member ring having only phosphorus as a heteroatom is prepared from 2-aminofuran-3-carbonitrile (compound 62).

EXAMPLE 30

Synthesis of 2-Aminophosphine-3-carbonitrile (compound 63)

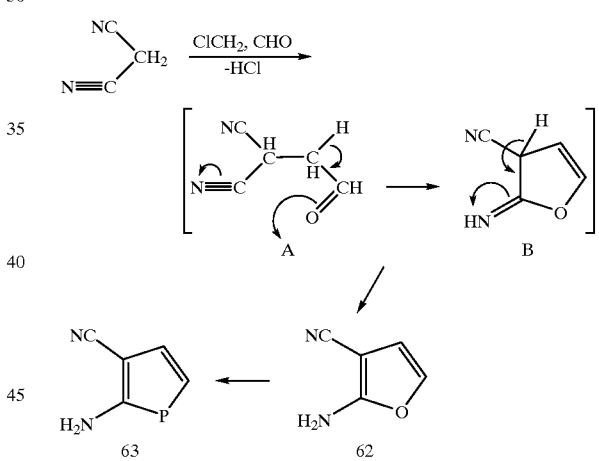

Condensation of malononitrile with chloroacetaldehyde in the presence of triethylamine in anhydrous tetrahydrofuran furnishes 2-aminofuran-3-carbonitrile (compound 62). The proposed reaction mechanism is: reaction of malononitrile with chloroacetaldehyde yields the intermediate A, which then cyclizes to give the compound 62 via the intermediate B. Similar cyclizations using a substituted halo-aldehyde and malononitrile are reported in the literature (88, 89). Treatment of compound 62 with tris (trimethylsilyl)phosphine gives the versatile starting material 2-aminophospholine-3-carbonitrile (compound 63).

EXAMPLE 31

Synthesis of the Tubercidin Analog 4-Amino-7-(β-D-ribofuranosyl)phospholo-[2,3-d]pyrimidine (compound 67).

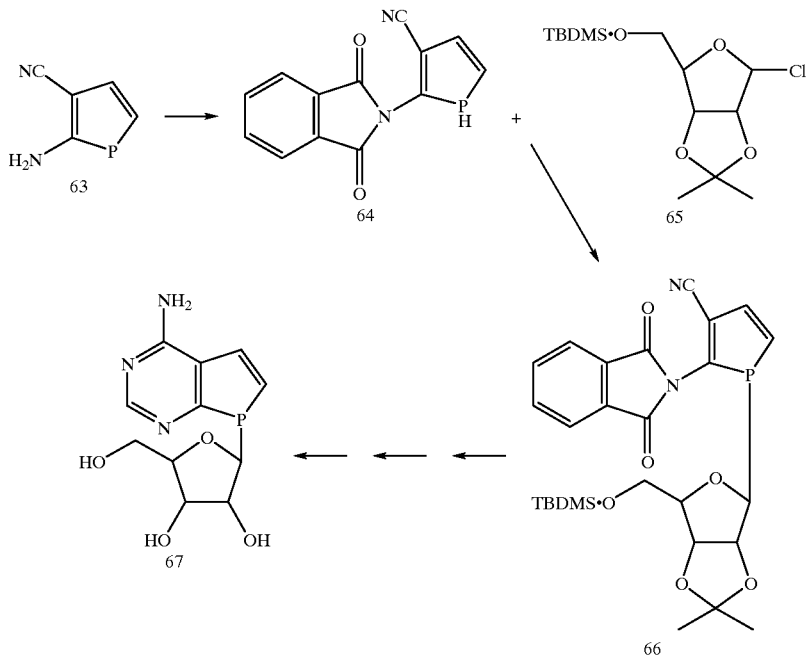

Protection of the amino group of compound 63 is effected by the fusion with phthalimide to give compound 64, which on glycosylation with 2,3-O-isopropylidene-5-O-(tert-butyldimethylsilyl)-α-D-ribofuranosyl chloride (compound 65) (63), under sodium salt (90) or Phase-Transfer (91) glycosylation condition gives the corresponding protected nucleoside (compound 66). Compound 66, on successive treatment with 0.1 N aqueous NaOH (to cleave the phthalimido group), fusion with formamidine acetate (to ring close) and aqueous trifluoroacetic acid (to cleve the TBDMS group and the isopropylidene group) provides the tubercidin congener 4-amino-7-(β-D-ribofuranosyl)phospholo[2,3-d]pyrimidine (compound 67).

EXAMPLE 32

Synthesis of 7-Deazainosine analog 7-(β-D-Ribofuranosyl)phospholo-[2,3-d]-pyrimidin-4(3H)-one (compound 69)

Alkaline hydrolysis of compound 66 under nonoxidative conditions provides the amino-carboxamide derviative (compound 68), which is then cyclized with treithyl orthoformate, followed by deacetonation under acidic conditions to furnish the 7-deazainosine analog (compound 69). Compound 69 is also prepared by deamination of compound 67 (the adenosine analog) with aqueous nitrous acid.

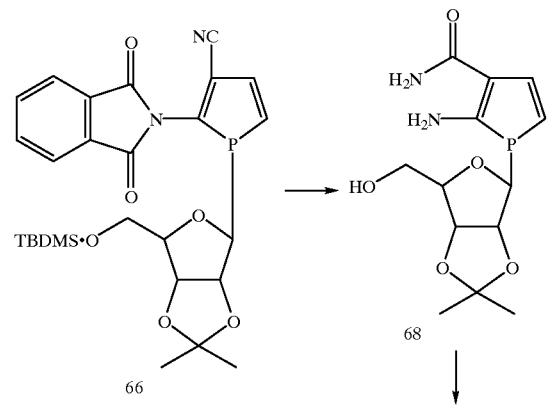

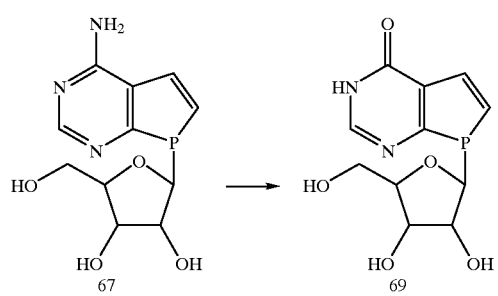

EXAMPLE 33

Synthesis of 7-Deazaguanosine analog 2-Amino-7-(β-D-ribofuranosyl)-phospholo[2,3-d]pyrimidin-4(3H-one) (compound 72)

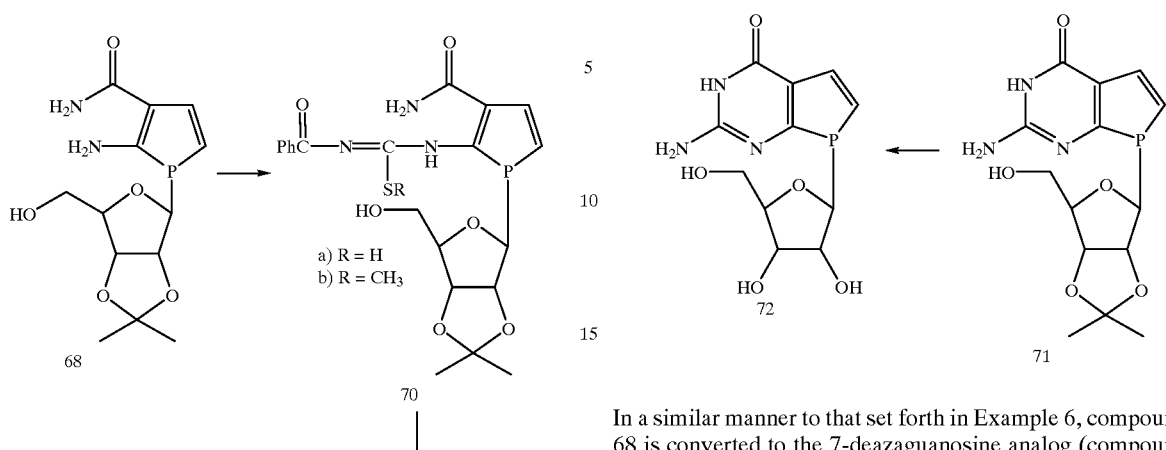
In a similar manner to that set forth in Example 6, compound 68 is converted to the 7-deazaguanosine analog (compound 72) by a conventional four-step reaction sequence via the thioureido intermediate, compound 70a.
EXAMPLE 34
Other nucleoside derivatives of Adenine and Guanine analogs (compound 74 and compound 77)
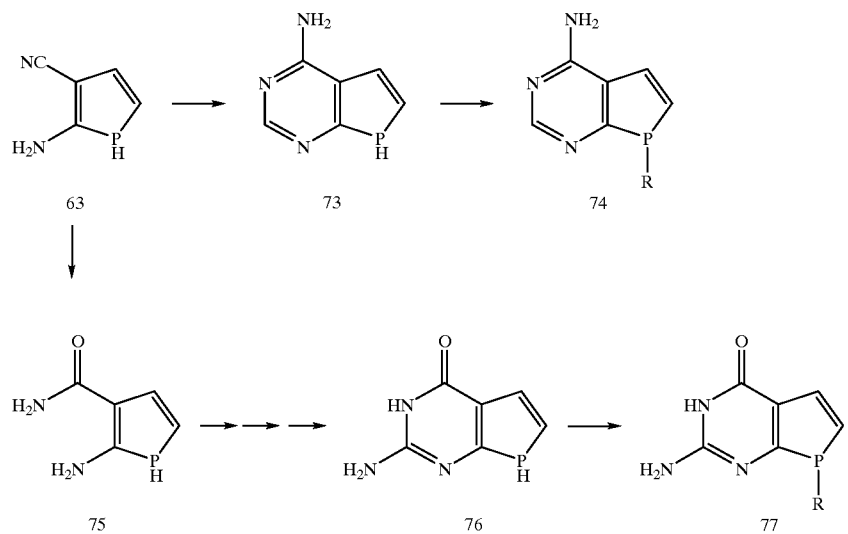
R is a carbohydrate moiety The nucleoside analogs include those species which contain modifications of the carbohydrate moiety, for example, wherein one or more of the hydroxyl groups are replaced with a hydrogen, halogen, a heteroatom, amines, thiols, and the like. In certain embodiments of the new compounds, the pentose moiety is replaced by a hexose and the stereochemistry of the carbohydrate carbons can be other than that of D-ribose. Nucleosides as defined herein are prepared as described in Examples 9 and 14.

EXAMPLE 35
Sangivamycin Analog of P-Substituted Deazaphosphole (compound 84)

and is prepared as previously described (93, 94). Treatment of malononitrile with compound 78 in aqueous solution containing NaOAc at reflux temperature (94) to give methyl 2-amino-3-cyanofuran- 4-carboxylate (compound 79). O-P conversion of compound 64 to obtain compound 80 is effected with tris- (trimethylsily)phosphine (TTP) in the presence of naked fluoride ion in boiling toluene. The amino group of the tri-substituted phospholine (compound 80) is protected with phthalimide group to obtain compound 81, which on glycosylation with 2,3-O-isopropylidene-5-O-(tert-butyldimethylsilyl)-α-D-ribofuranosyl chloride, under the stereospecific sodium salt glycosylation conditions (90) yields the key intermediate compound 82. A removal of the

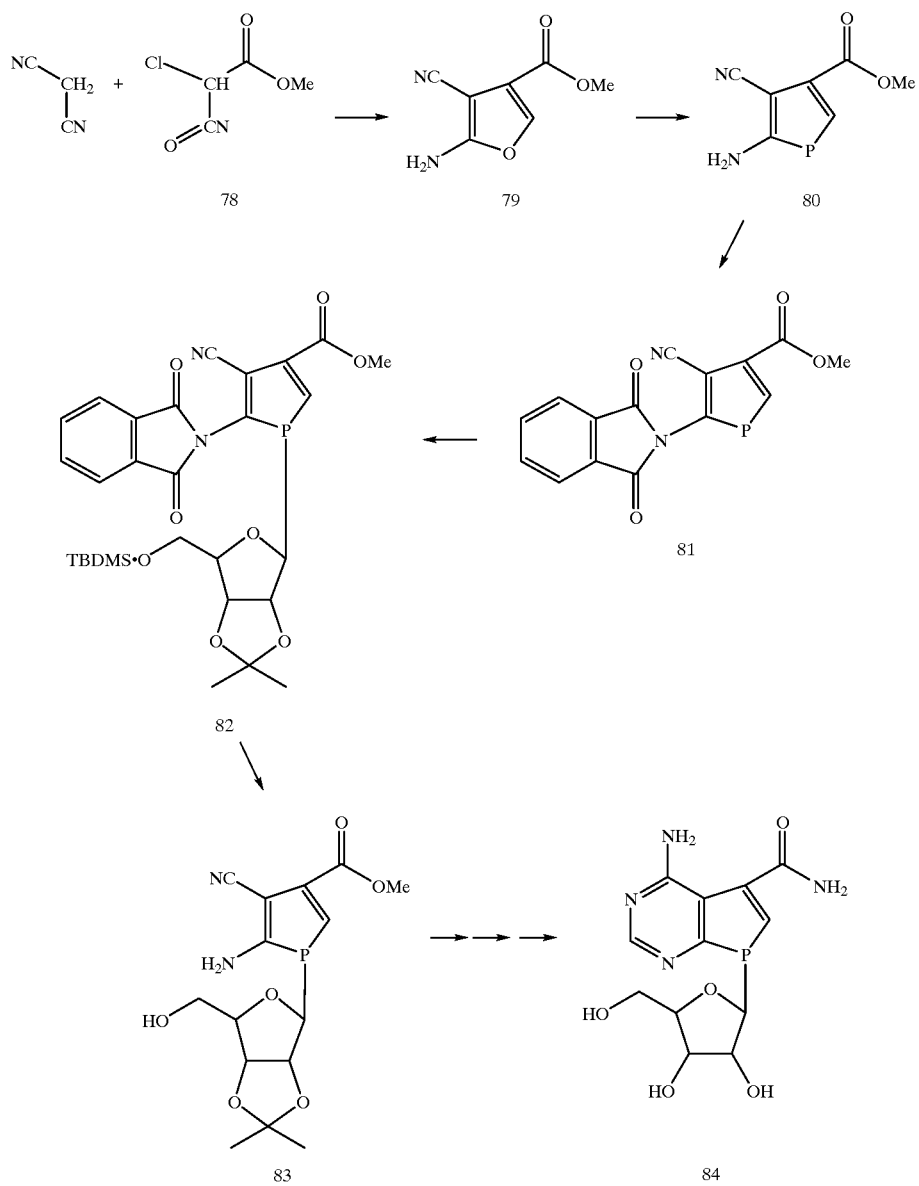

Synthesis of sangivamycin analog in which phosphorus is a component of the pyrrole moiety is accomplished using appropriate furan. Based on chloroacetaldehyde precedent (92), a 2,3,4-trisubstituted furan (compound 79) is generated. The key substrate that is used for the synthesis of compound 79 is methyl chloroformylacetate (compound 78)

blocking groups by the treatment with a weak base provides methyl 2-amino-3-cyano-1-(2,3-O-isopropylidene-β-D-ribofuranosyl)phospholine-4-carboxylate (compound 83). Ring closure of this o-aminonitrile (compound 83) by the conventional procedure provides the sangivamycin analog compound 84.

EXAMPLE 36
Toyocamycin Analog of P-substituted Deazaphosphole (compound 96)

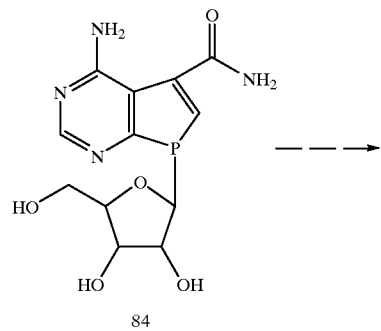
84

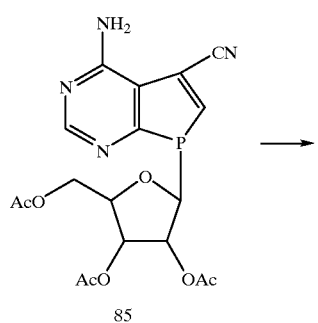
85

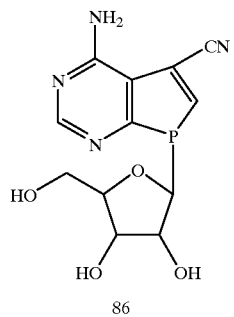
86

Selective acetylation (96) of sugar hydroxyls of compound 84 by the treatment with acetic anhydride in the presence of 4-(dimethylamino)pyridine (DMAP) at −25° C. and subsequent dehydration of the carbamoyl group with phosgene (95) gives compound 85. Careful deacetylation of compound 85 with methanolic ammonia at 0° C. or with aqueous sodium bicarbonate (97) affords the toyocamycin analog of P-substituted deazaphosphole (compound 86).

EXAMPLE 37
Thiosangivamycin and Related Analogs of P-substituted Deazaphosphole (compound 87)

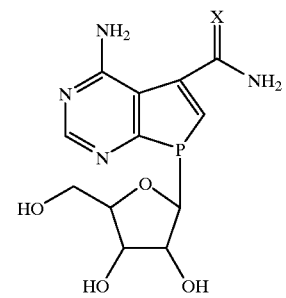
87
X = S, NH, NOH, etc.

Treatment of toyocamycin analog (compound 86) with hydrogen sulfide gas in dry pyridine in the presence of triethylamine at room temperature provides the thiosangivamycin analog (compound 87, X=S). Similarly, compound 86 is converted into the corresponding carboxamidine (compound 87, X=NH) and carboxamidoxime (compound 87, X=NOH) by the treatment with liquid anmmonia/ammonium chloride and hydroxylamine, respectively. The carbonitrile function of compound 86 is also available for further transformation reactions.

EXAMPLE 38
P-substituted Deazaphosphole Analogs Related to 7-Deazainosine (compound 89).

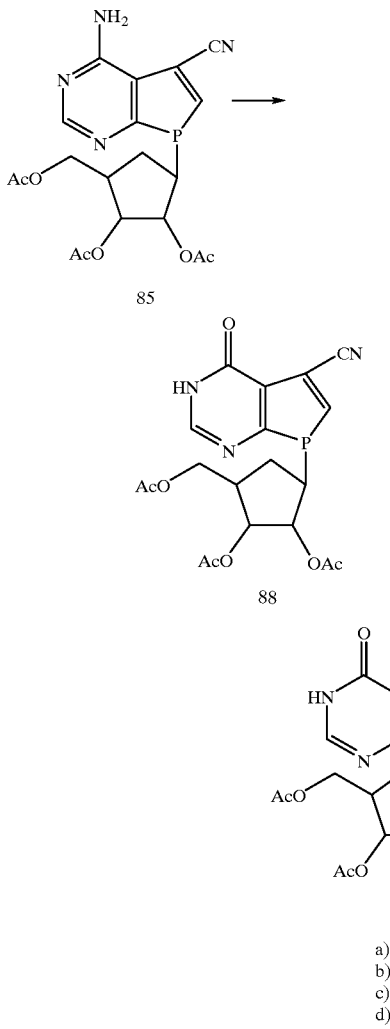

85

88

89
a) X = O
b) X = S
c) X = NH
d) X = NOH

Intermediate compound 4-amino-7-(2,3,5-tri-O-acetyl-β-D-ribofuranosyl)phospholo-[2,3-d]pyrimidine-5-carbonitrile (compound 85) from Example 36 may be deaminated with aqueous nitrous acid (98) to form the intermediate compound 7-(2,3, 5-tri-O-acetyl-β-D-ribofuranosyl)-4(3H)-phospholo[2,3-d]pyrimidine-5-carbonitrile (compound 88). Since the carbonitrile function of compound 88 is highly reactive toward nucleophilic substitution displacement reactions (99), a variety of 5-substituted-4(3H)-phospholo[2,3-d]pyrimidine nucleosides is prepared. Thus, oxidative hydrolysis of compound 88 by the treatment with $NH_4OH/H_2O_2$ at room temperature (97) forms 7-(β-D-ribofuranosyl)-4(3H)-phospholo[2,3-d]pyrimidine-5-carboxamide (compound 89a). The corresponding 5-thiocarboxamide (compound 89b) is obtained by treatment of compound 88 with $H_2S$ in dry pyridine in the presence of triethylamine. A facile conversion of the nitrile function of compound 88 is also accomplished using the procedures previously employed in our laboratory (100) to obtain compounds 89c (by the treatment with $NH_3/NH_4Cl$) and 89d (by the treatment with free $NH_2OH$ in EtOH).

EXAMPLE 39

Other Nucleoside Derivatives of Toyocamycin and Sangivamyein Analogs of P-substituted Deazaphospholes (compound 90)

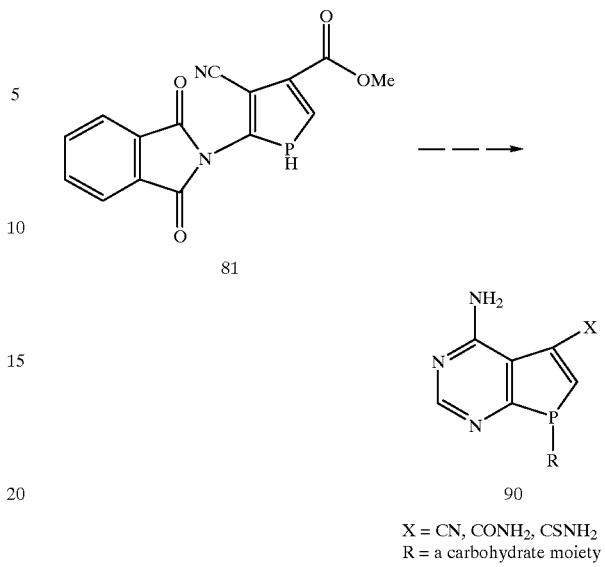

81

90

X = CN, CONH₂, CSNH₂
R = a carbohydrate moiety

The fraudulent nucleosides, 2'-deoxysangivamycin, ara-toyocamycin, arafluoro-tubercidin and the like have shown selective activity against HCMV. Therefore, the analogs of the above nucleosides in the P-substituted deazaphospholes (compound 90) are prepared analogously. The nucleoside analogs include those species which contain modifications of the carbohydrate moiety, for example, wherein one or more of the hydroxyl groups are replaced with a hydrogen, halogen, a heteroatom (e.g. azido), amines, thiols, and the like. The pentose moiety is replaced by a hexose. The stereochemistry of the carbohydrate carbons can be other than that of D-ribose. Nucleosides as defined herein are prepared as described in Examples 9 and 14.

III. EXAMPLE 40

Synthesis of 2-Azaphosphazoles (1,3-Azaphospholo[4,5-d]-v-triazines and Their Nucleosides)

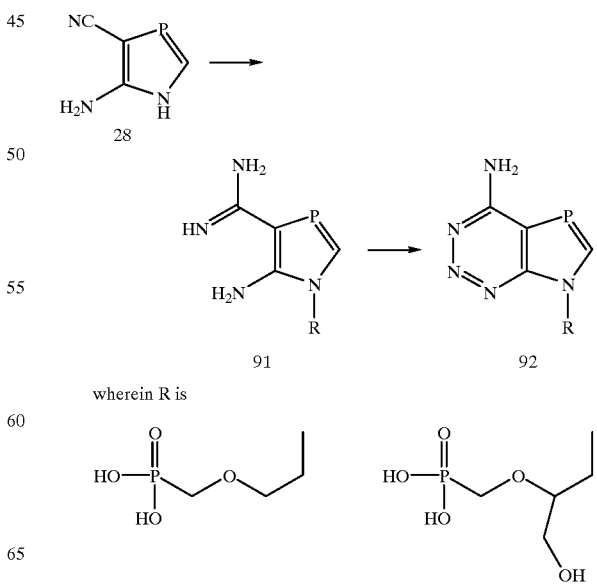

wherein R is

49
-continued

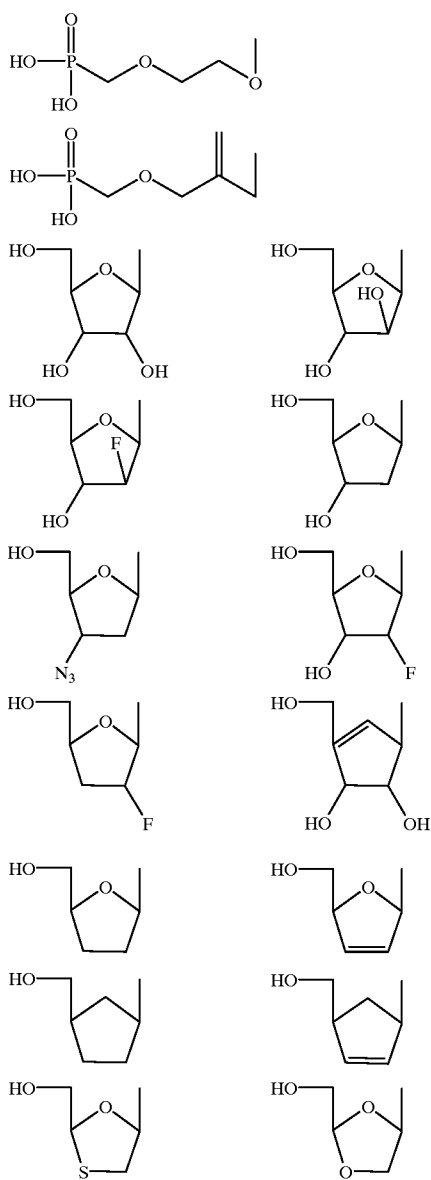

The synthesis of the compounds in Example 40 proceeds by the direct alkylation of the phosphazoline compound (28, from Example 15) with requisite alkyl halides or properly protected glycosyl halides in appropriate solvents. In the case of glycosyl derivatives, subsequent deprotection of the glycosylated product under alkaline conditions is required. The alkylated compound 28 on further treatment with liquid amonia in the presence of $NH_4Cl$ at elevated temperature and pressure affords the corresponding 4-carboxamidines

50

(compound 91), which on treatment with sodium nitrite in aqueous acetic acid furnishs various 2-azaphosphazoles (compound 92).

EXAMPLE 41

Synthesis of 2-Azaphosphazolones Related to 2-Azainosine

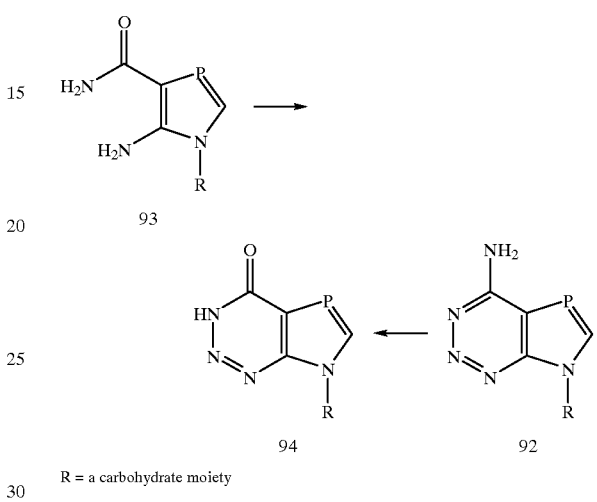

R = a carbohydrate moiety

Compounds 92 (from Example 40) on deamination with aqueous nitrous acid produces 2-azainosine analogs (compound 94), which can also be prepared by ring-annulation employing amino-carboxamide compound 93 under stronger acidic conditions (6N HCl) and low temperature (−25° C.) (101).

IV. Synthesis of 8-Azaphosphazoles (1,3,2-Diazaphospholo[4,5-d]pyrimidines and Their Nucleosides)

The isolation of Pathocidin (8-azaguanine) from natural sources (102, 103) together with the observed array of biological activities (68, 104) generated tremendous interest in the synthesis of 8-azapurine nucleosides. The synthesis of 8-azaphosphazole nucleosides is of biological interest.

EXAMPLE 42

Synthesis of 8-Azaadenosine analog 4-Amino-1-(β-D-ribofuranosyl)-1,3,2-diazaphospholo[4,5-d]pyrimidine (compound 100)

51

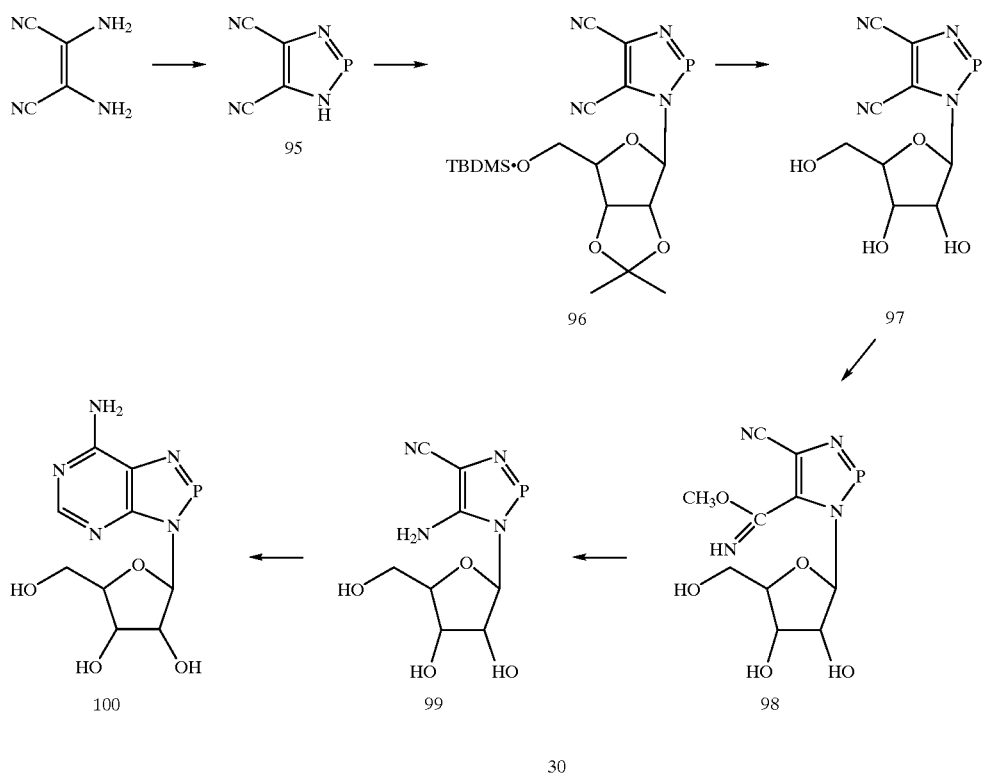

Reaction of diaminomaleonitrile with hexamethylphosphorus triamide in anhydrous acetonitrile gives the key starting material 4,5-dicyano-1,3,2-diazaphospholine (compound 95) (105). Glycosylation of the sodium salt of 95 with the α-halogenose 2,3-O-isopropylidene-5-O-(tert-butyldimethylsilyl)-α-D-ribofuranosyl chloride (63) in acetonitrile furnishs the protected nucleoside, compound 96, as the only product, since N-1 and N-3 being symmetrical. Deprotection of the carbohydrate moiety with aqueous trifluoroacetic acid gives 1-(β-D-ribofuranosyl)-1,3,2-diazaphospholin-4,5-dicarbonitrile (compound 97). Treatment of compound 97 with 1 'equivalent of sodium methoxide in methanol at room temperature results in the formation of the imidate ester, compound 98, regiospecifically. Similar regiospecific formation of the imidate ester from 4,5-dicyano-1-(2,3,5-tri-O-benzoyl-β-D-ribofuranosyl)imidazole has been documented (106). In analogy to the imidazole chemistry (106), when compound 98 is treated with 5% sodium hypochlorite solution, 5-amino-1-(β-D-ribofuranosyl)-1,3,2-diazaphospholine-4-carbonitrile (compound 99) is produced. This reaction may proceed by the elimination of $CH_3Cl$ from the initially formed N-chloro derivative of compound 98. Such Beckman type rearrangement of an N-chloroimidate has been documented (107). Ring closure of compound 99 with diethoxymethyl acetate in the presence of ammonia gives the 8-azaadenosine analog, 4-amino-1-(β-D-ribofuranosyl)-1,3,2-diazaphospholo[4,5-d]pyrimidine (compound 100).

EXAMPLE 43

Synthesis of 8-Phosphainosine, 1-(β-D-Ribofuranosyl)-1,3,2-diazaphospholo[4,5-d]pyrimidine-4(5H)-one (compound 102)

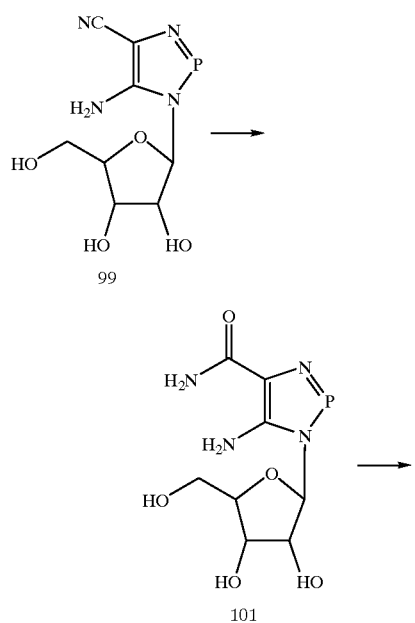

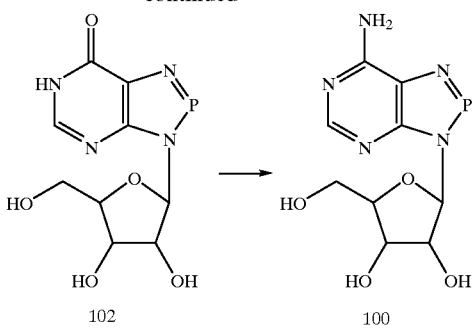

Hydrolysis of compound 99 with aqueous NaOH at room temperature produces 5-amino-1-(β-D-ribofuranosyl)-1,3,2-diazaphospholine-4-carboxamide (compound 101), which on further treatment with diethoxymethyl acetate in the presence of ammonia gives 8-phosphainosine (compound 102). Compound 102 can also be prepared by the deamination of the adenosine analog, compound 100, with aqueous nitrous acid.

EXAMPLE 44
Synthesis of 8-Phosphaguanosine, 6-Amino-1-(β-D-ribofuranosyl)-1,3,2-diazaphospholo[4,5-d]pyrimidin-4 (5H)-one (compound 105)

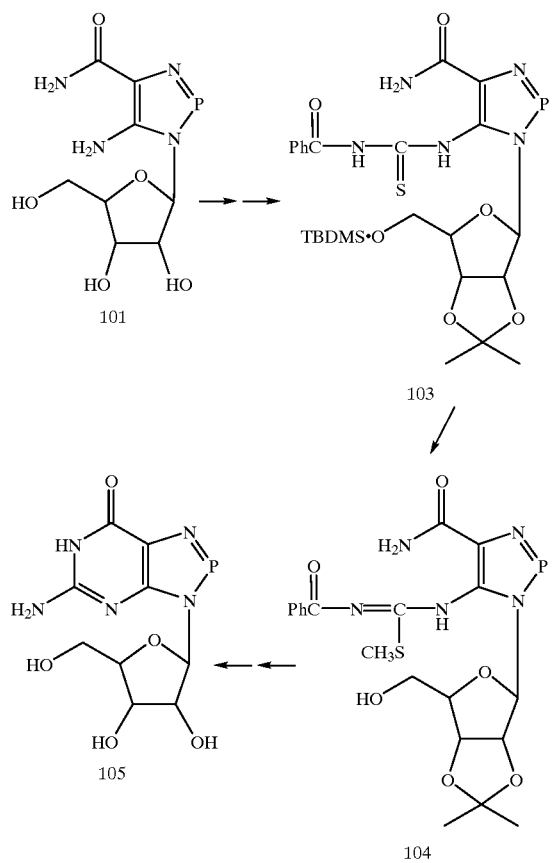

Isopropylidenation of compound 101, followed by conventional four-step reaction sequence via the 5-thioureido intermediate (compound 103), as described in Example 26, yields the 8-phosphaguanosine analog (compound 105)

EXAMPLE 45
Other nucleoside derivatives of 8-Phosphaadenine and 8-Phosphaguanine (compound 107 and compound 109).

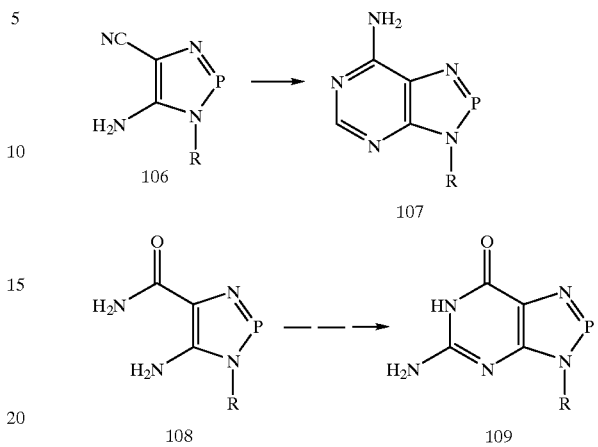

R is a carbohydrate moiety

The nucleoside analogs include those species that contain modifications of the carbohydrate (sugar) moiety, for example, wherein one or more of the hydroxyl groups are replaced with a hydrogen, halogen, a heteroatom (e.g. azido), amines, thiols, and the like. The pentose moiety can be replaced by a hexose. The stereochemistry of the carbohydrate carbons can be other than that of D-ribose. Nucleosides as defined herein are prepared as described in Examples 9 and 14.

Table 1 provides a list of preferred embodiments of the phosphazoles of the present invention that are suitable for use as pharmaceutical agents. The number in parentheses beside each compound indicates the Example Number where its manner of synthesis is described. The "T" numbers, such as T70241, T70242, T70245, T70254, T70256, T70262, T70268, etc. indicate proprietary reference numbers of preferred embodiments for which physical characteristics are denoted in the corresponding experiments. Efficacy and non-toxicity of representative compounds of the present invention are shown in the following examples, and in Tables 2 and 3 and FIGS. 1–9.

The adenine analog phosphazole (compound 10, T70241) was assayed for activity against the cytokines TNF(X and IL-1β. The effect of T70241 on LPS-stimulated TNFα production was assessed in both THP-1 cells and human PBMC cells in culture. The results of these assays are presented in the following examples and in the Figures referred to therein.

EXAMPLE 46
Inhibition of TNFα by the Adenine Analog Phosphazole (T70241)

Cell line. THP-1 cells (human monocyte) were maintained in RPMI 1640 medium containing 25 mM Hepes buffer, 2 mM L-glutamine, 50 units of penicillin per mL, 50 μg of streptomycin sulfate per mL, and 10% heat-inactivated fetal bovine serum (FBS) in a humidified incubator containing 5% $CO_2$. The cells were split 1:4 weekly as recommended by the American Type Culture Collection (ATCC). TNFα assay. Varying concentrations of the test compound or control compound were added to THP-1 cells plated at a density of $1\times10^6$ cells/mL in 600 μL of 10% RPMI in a 48 well plate. After one hour the cells were stimulated with 0.5 μg of lipopolysaccharide (LPS; Sigma, lot number 43H40491) per mL. Six hours post-stimulation supernatants were collected and assayed for TNFα or IL-1β production using a commercially available cytokine detection ELISA (Enzyme Linked Immunosorbent Assay) kit according to the suppliers instructions. A suitable assay kit may be obtained from Biosource, or R and D systems. A novel xanthine analog, HWA-3138, having the structure (as shown below) was used as the control compound (30) in this study to monitor the response of the THP-1 cells. Xanthine analogs are known inhibitors of TNFα but not IL-1β. In the following experiments compound HWA-3138 was used as a positive control.

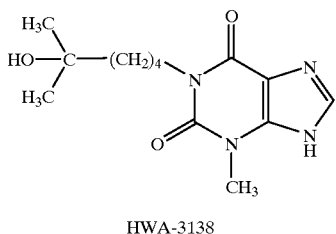

HWA-3138

Cytotoxicity Analysis. The cytotoxicity of the compounds were assayed using the CellTiter 96™ Aqueous Non-Radioactive Cell Proliferation (MTS) Assay kit obtained from Promega (Madison, Wis.) following the instructions provided by the supplier. The viable cell number was determined by trypan blue staining and cells (THP-1) were resuspended in PRMI supplemented with 10% FBS (GIBCO). Eighty microliters of cell suspension ($1.7 \times 10^4$ cells/well) was dispensed onto a 96-well microtiter plates. At this time 20 μL of drug (or control) was added to appropriate wells. Each concentration was assayed in quadruplicate. The plates were incubated at 37° C. in a humidified 5% $CO_2$ atmosphere for 4 days and MTS assay sample was graphed for each concentration and the data obtained was used to calculate $TC_{50}$ (the concentration of the compound necessary to inhibit the cell growth by 50%) for each compound.

FIG. 1A shows the toxicity of compound T70241 in THP-1 cells. In this Figure, the concentration of compound T70241 added is plotted against the observed percent of THP-1 cells surviving after 4 days incubation. Even the highest concentration of compound T70241 tested, 1 mg/mL, had no toxic effect on the THP-1 cells. In fact, not only is T70241 non-toxic to THP-1 cells, it stimulates THP-1 growth at higher concentrations, as shown in FIG. 1A. These results demonstrate that the biological activity of compound T70241 obtained in the subsequent experiments are not influenced by toxicity.

Figure 1B:
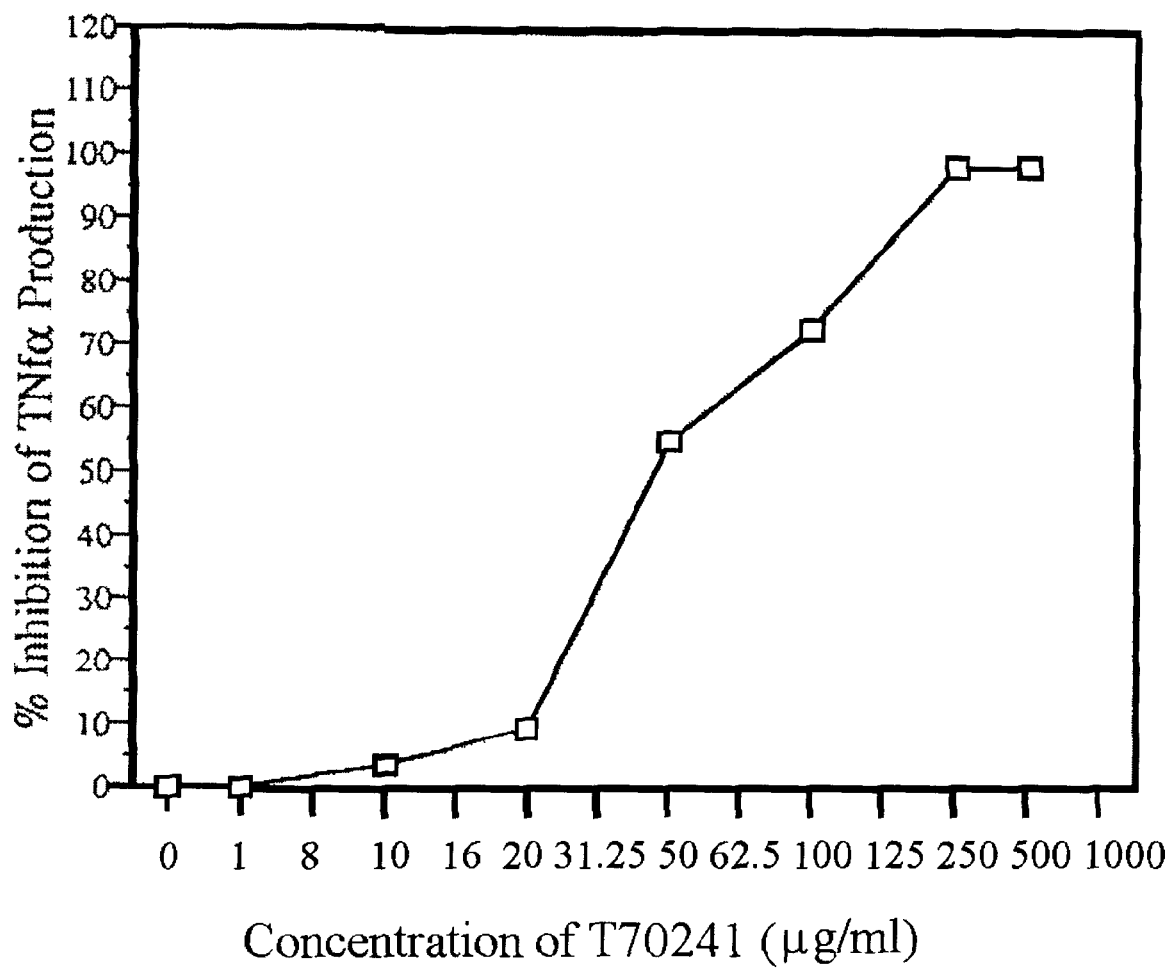

FIG. 1B is a graph showing the percent inhibition of TNFα production obtained at each concentration of compound T70241. From FIG. 1B, 50% inhibitory concentration ($IC_{50}$) of T70241 was calculated to be about 23. 9 μg/mL.

Figure 2:
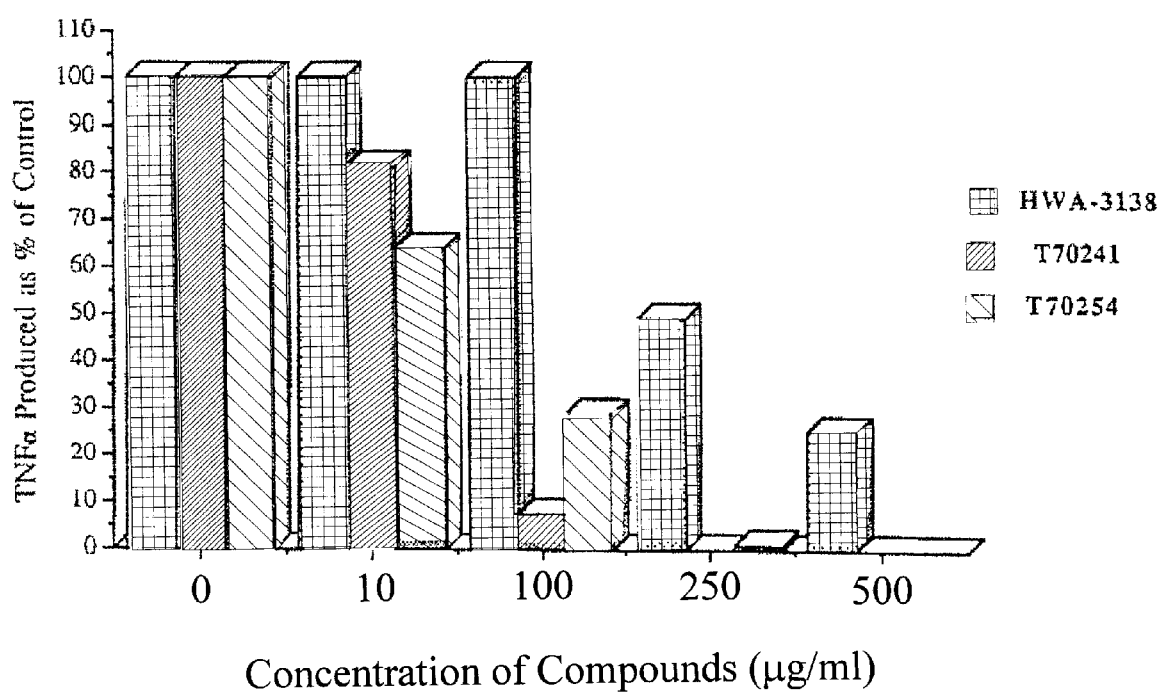
FIG. 2 shows percent inhibition of TNFα production by LPS stimulated THP-1 cells by the adenine analog (compound 10), and N-pentenyl derivative of the adenine analog [compound 21, R=$(CH_2)_4CH_3$] compared to HWA-3138, a xanthine analog control compound.

Referring now to FIG. 2, a dose response graph is provided showing the anti-TNFα activity of compound T70241 compared to a control, the HWA-3138 xanthine analog, and to another phosphazole compound T70254. Certain xanthine analogs, such as HWA-3138, are known inhibitors of TNFOL and are currently used as the standard compounds to measure the effectiveness of any given anti-TNFα compound. The data plotted are the results obtained by monitoring the level of TNFα in culture medium 6 hours post-stimulation of THP-1 cells with LPS. At concentrations as little as 10 μg/mL, T70241 inhibits TNFα production in these cells better than the control xanthine compound. The control compound, a xanthine analog HWA-3138, provided no inhibition at concentrations of 10 and 100 μg/mL, whereas the phosphazole compound T70241 yielded about 25% and 90% inhibition at the same concentrations.

Figure 3:
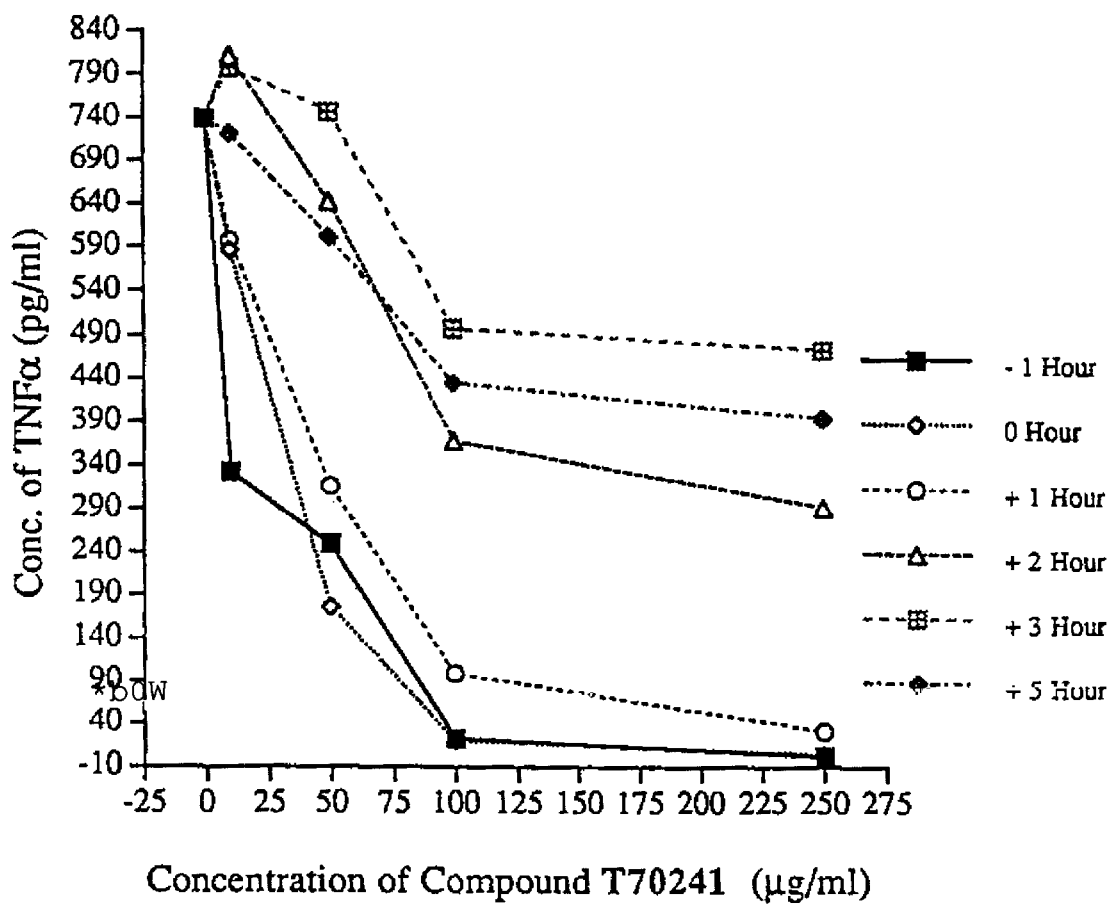
FIG. 3 shows the results of time of addition of compound 10 on TNFα production in LPS-stimulated THP-1 cells in culture.

Time of Addition. Varying concentrations of test or control compounds were added to THP-1 cells ($1 \times 10^6$ cells/mL) at different time points post-stimulation using 0.5 μg of LPS (Sigma, lot number 43H40491) per mL in 300 μL of 10% RPMI in a 48 well plate. Six hours post-stimulation supernatants were collected and assayed for TNFα or IL-1β production using a Biosource cytokine detection ELISA (Enzyme Linked Immunosorbent Assay) kit according to the supplier's instructions. As shown in FIG. 3, even if compound T70241 is added to cultures 5 hours post-LPS stimulation, the phosphazole analog is still able to significantly reduce the level of TNFα in the culture medium one hour later, i.e., at 6 hours post-LPS stimulation. Although this property is not unique to compound T70241, it clearly shows that T70241 does not interfere with LPS.

The membrane bound TNFα was separated from the free TNFα in the culture medium at 6 hours post-LPS stimulation as follows: The corresponding cells were centrifuged at 3500 rpm (~1,000×g) for 6 min. The supernatants were removed and the cell pellets were then resuspended in 200 μL of 0.25 mM Tris-HCl (pH 7.4). The cell associated TNFα was prepared by freezing the cell suspension in dry ice/ethanol and thawing at 37° C. three times with Vortexing in-between freeze-thaw cycles. Each cycle was 4–5 min apart.

Figure 4:
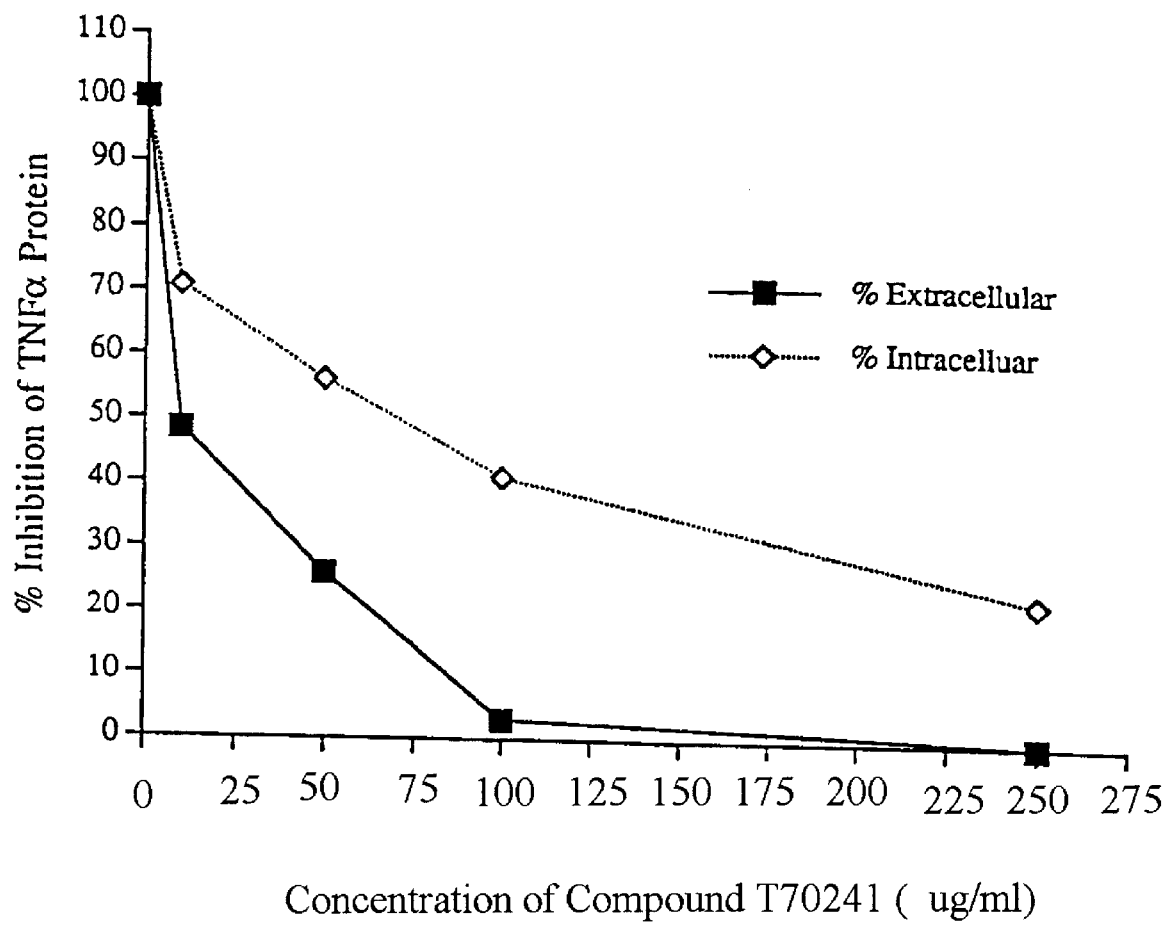
FIG. 4 is a graph showing the relative quantities of intracellular and extracellular TNFα before and after addition of compound 10 to LPS-stimulated THP-1 cells in culture.

FIG. 4 shows the level of membrane bound (intracellular) and free (extracellular) TNFα present in cells or in the culture medium 6 hours post-LPS induction for cultures treated with compound T70241. As seen from the data, compound T70241 is able to reduce the levels of both cell associated and free TNFα. At the lowest concentration tested, TNFα is reduced by about 50% and 30%, respectively, in the extracellular and membrane-bound fractions. Although this finding is not unique to compound T70241, it suggests that compound T70241 is acting inside the cell and the observed reduction in TNFα production in supernatants represents the actual inhibition of TNFα expression.

Figure 5A:
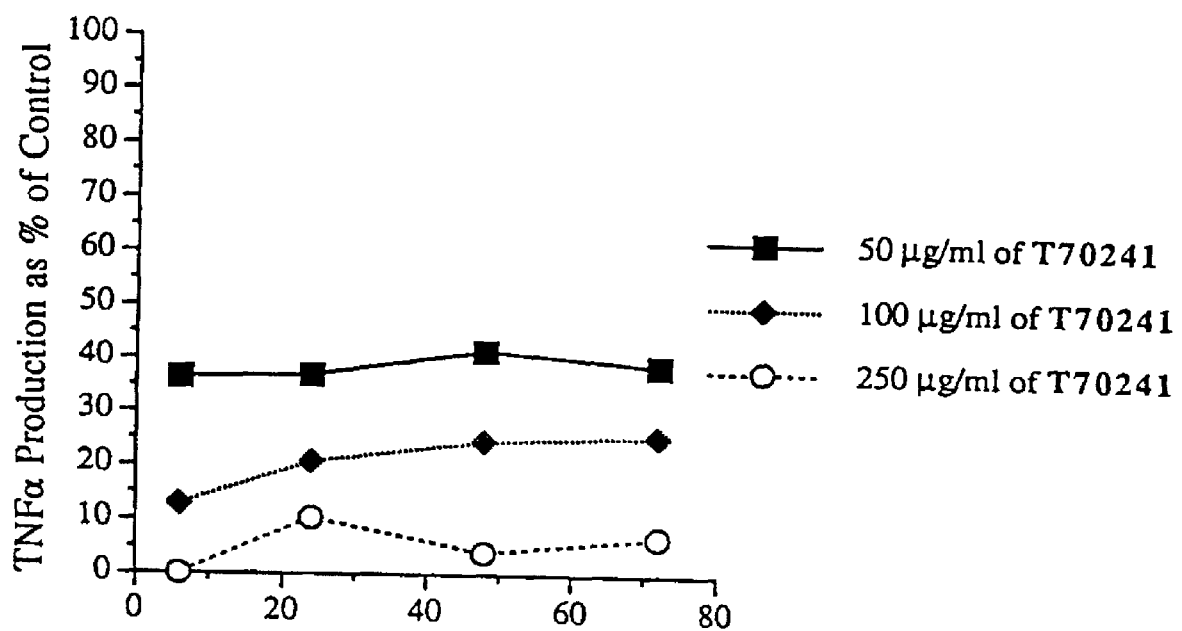
FIGS. 5A and 5B shows the long-term effects of compound 10 on TNFα production after a single treatment, compared to HWA-3138, a xanthine analog control compound.
Figure 5B:
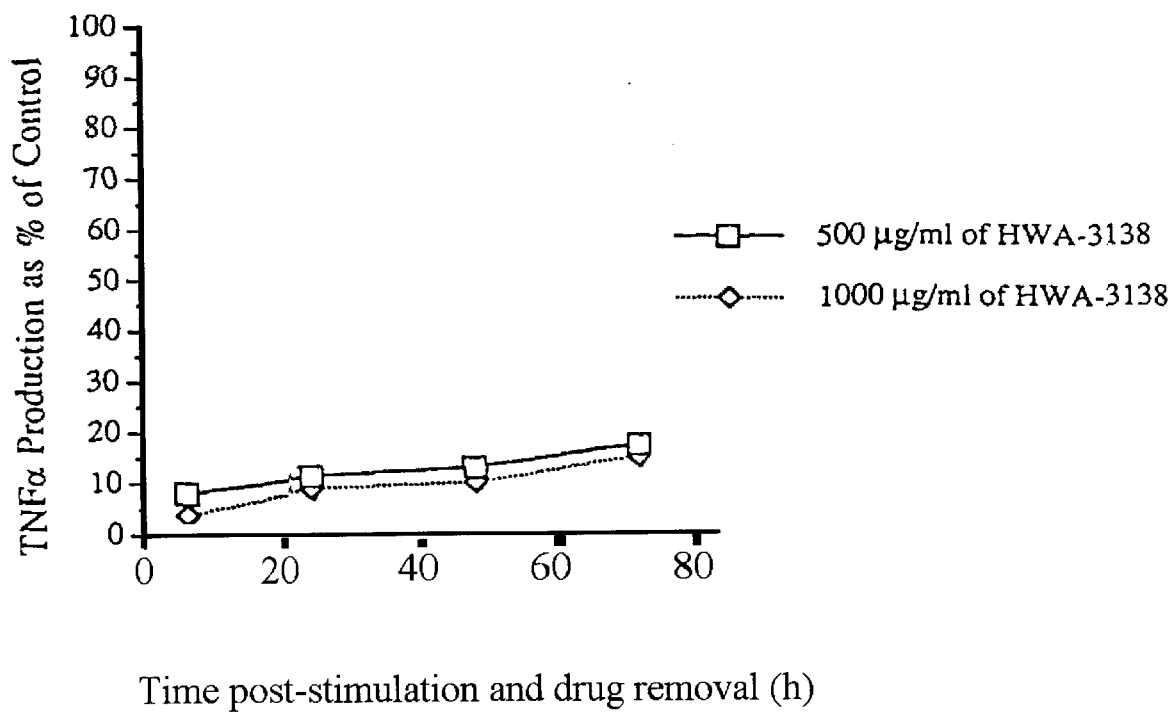

To determine the long-term effects of phosphazole compound T70241 on TNFα production after a single treatment, THP-1 cells were pre-incubated with T70241, washed and resuspended in drug free medium. The xanthine analog HWA-3138 was used as a control. The results of this study are presented in FIG. 5. Compound T70241 was able to inhibit TNF(X production in a dose dependent fashion for 72 hours after the drug removal as shown in FIG. 5A. The xanthine analog HWA-3138 produced a similar effect but at much higher drug concentration as shown in FIG. 5B.

EXAMPLE 47

Inhibition of IL-1β by Adenine Analog Phosphazole

THP-1 cells were cultured and IL-1β inhibition assays were conducted as described for TNFα in Example 46, except a commercially available IL-1β assay kit, obtained from R and D Systems, Minneapolis, Minn., was used instead of the TNFα kit.

Figure 6:
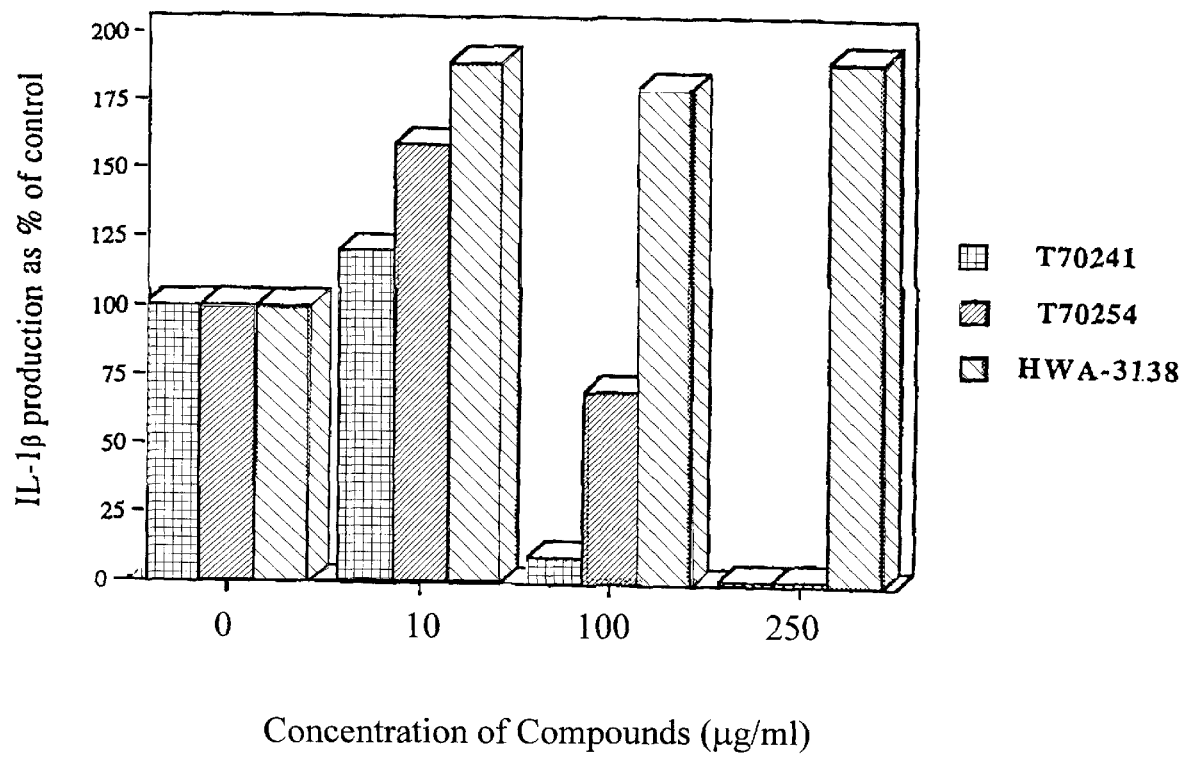
FIG. 6 is a bar graph showing the inhibition of IL-1β production in THP-1 cells stimulated with LPS by certain phosphazoles and compared to HWA-3138, a xanthine analog control compound.

FIG. 6 shows the dose response profile obtained for the phosphazole compound T70241 when tested for its ability to inhibit IL-1β production. The T70241 compound is graphed with comparable data for the T70254 phosphazole and the xanthine analog HWA-3138 control. The control compound HWA-3138 does not inhibit IL-1β production at the concentrations tested, i.e., 10–250 μg/mL. As seen in FIG. 6, the adenine analog phosphazole (T70241) is able to inhibit IL-1β production at concentrations in the range of 50 to 100 μg/mL. The $IC_{50}$ for T70241 in this experiment was calculated to be 38.76 μg/mL. These results suggest that compound T70241 and the xanthine analog HWA-3138 exhibit different mechanisms of action.

Figure 7:
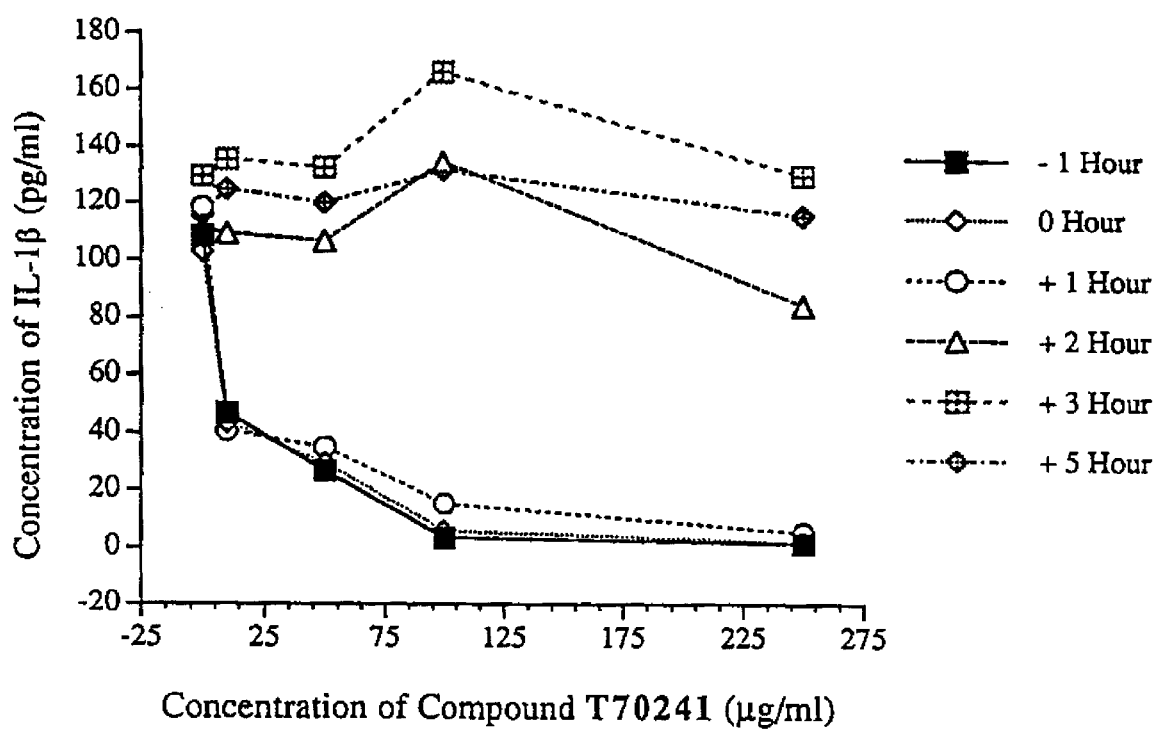
FIG. 7 shows the relationship of time of addition of compound 10 on IL-1β production in LPS-stimulated THP-1 cells.

In "time of addition" studies, shown in FIG. 7, it can be seen that T70241 must be added within 1 to 2 hours of LPS induction of IL-1β in order to produce a dramatic reduction in IL-1β production at 6 hours post stimulation, which is different from the results obtained for TNFα inhibition by T70241. In those studies, the phosphazole compound T70241 could be added as late as 5 hours post-induction of TNFα and still sharply inhibit the amount of cytokine in the culture at 6 hours post induction (as shown in FIG. 3).

Figure 8:
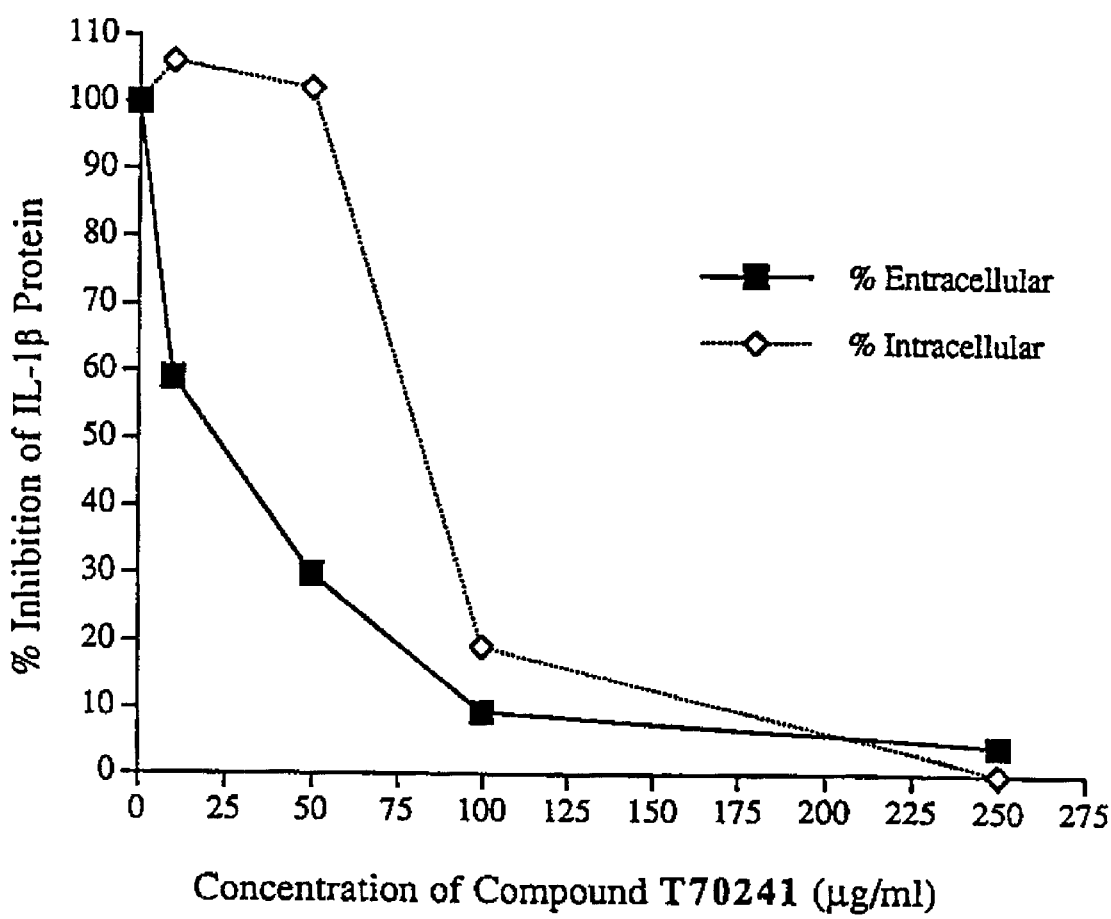
FIG. 8 is a graph showing the relative amounts of extracellular and intracellular IL-1β before and after addition of compound 10 to LPS-stimulated THP-1 cells.

With reference now to FIG. 8, for each concentration of T70241 tested, the membrane bound IL-1β was separated from the IL-1β found free in the culture medium at 6 hours post-LPS stimulation as described in Example 46 for TNFα, and the percent inhibition of each fraction was graphed. Compound T70241 was found to reduce both the cell-associated (intracelluar) and the free (extracellular) IL-1β, similar to the results shown for inhibition of TNFα (shown in FIG. 4).

The phosphazole T70241 was further evaluated for its activity against IL-1β in PBMCs stumulated with LPS and aliquotes collected after 4, 24 and 48 hour post-stimulation. The results of this study are compiled in Table 3. Compound T70241 inhibited IL-1β up to 48 hour in a dose dependent fashion (Table 3). In the same experiment we show that cell viability was not affected after 48 hours of exposure to compound T70241.

EXAMPLE 48

Anti-HCMV Activity of Adenine Analog Phosphazole T70241

The adenine analog phosphazole (compound T70241) was assayed for antiviral activity using a HCMV plaque reduction assay, in accordance with known methods such as that described in U.S. Pat. No. 5,446,045.

Cell Culture. Vero (African Green Monkey kidney cells) and MRC-5 (diploid Human Embryonic Lung fibroblasts) cells were obtained from the American Type Culture Collection (ATCC) and were grown in minimal essential medium (MEM) with Earl's salts and glutamine (GIBCO BRL, Life Technologies, Inc.) with 10% heat inactivated fetal bovine serum (GIBCO BRL) and penicillin (100 μg/mL)/streptomycin (100 μg/mL).

CMV Cytopathic Effect (CPE) Assay. Assays were performed essentially as described by Lewis et al. (111), which report is incorporated herein by reference. MRC-5 cells (100,000 cells/well) were seeded in 24-well plates overnight. Medium was then removed and wells were rinsed once with 250 μL of 2% FCS-MEM before adding 40–50 pfu of HCMV (Town strain) to each well. After 2 hours of virus adsorption, the medium was removed and the cells were rinsed once with 2% FCS-MEM. Varying concentrations of the phosphazole compound in the culture medium (1 mL) was then added to appropriate wells and plates were incubated for 5–6 days at 37° C. in a humidified 5% $CO_2$ atmosphere. Each concentration was tested in duplicate wells.

The extent of the plaque reduction was quantitated by removing the media and adding 200 μL of 0.1% crystal violet in 20% methanol to all wells. The crystal violet was then removed after 10 min staining at room temperature by rinsing in the sink with tap water and the plates dried overnight. The plaques were then counted using a Nikon inverted microscope.

The results of the HCMV assays are given in Table 4 and FIG. 9B, showing a nearly logrithmic increase in inhibition of virus production over a 0.01–10 μg/mL range of T70241 phosphazole.

Cytotoxicity Analysis. The cytotoxicity of the compound was assayed using few the CellTiter 96™ Aqueous Non-Radioactive Cell Proliferation (MTS) Assay (Promega). Briefly, viable cell number was determined by trypan blue staining and cells (MRC-5 and Vero) were resuspended in minimal essential medium (MEM) supplemented with 10% FBS (GIBCO). Eighty microliters of cell suspension (1.7× $10^4$ cells/well) was dispensed onto a 96-well microtiter plates. At this time 20 μL of drug (or control) was added to appropriate wells. Each concentration was assayed in quadruplicate. The plates were incubated at 37° C. in a humidified 5% $CO_2$ atmosphere for 4 days and MTS assay was performed according to the manufacturer's instructions. The average absorbence of the sample was graphed for each concentration and the data obtained was used to calculate $TC_{50}$ (the concentration necessary to give one-half maximum growth) for each compound.

Figure 9A:
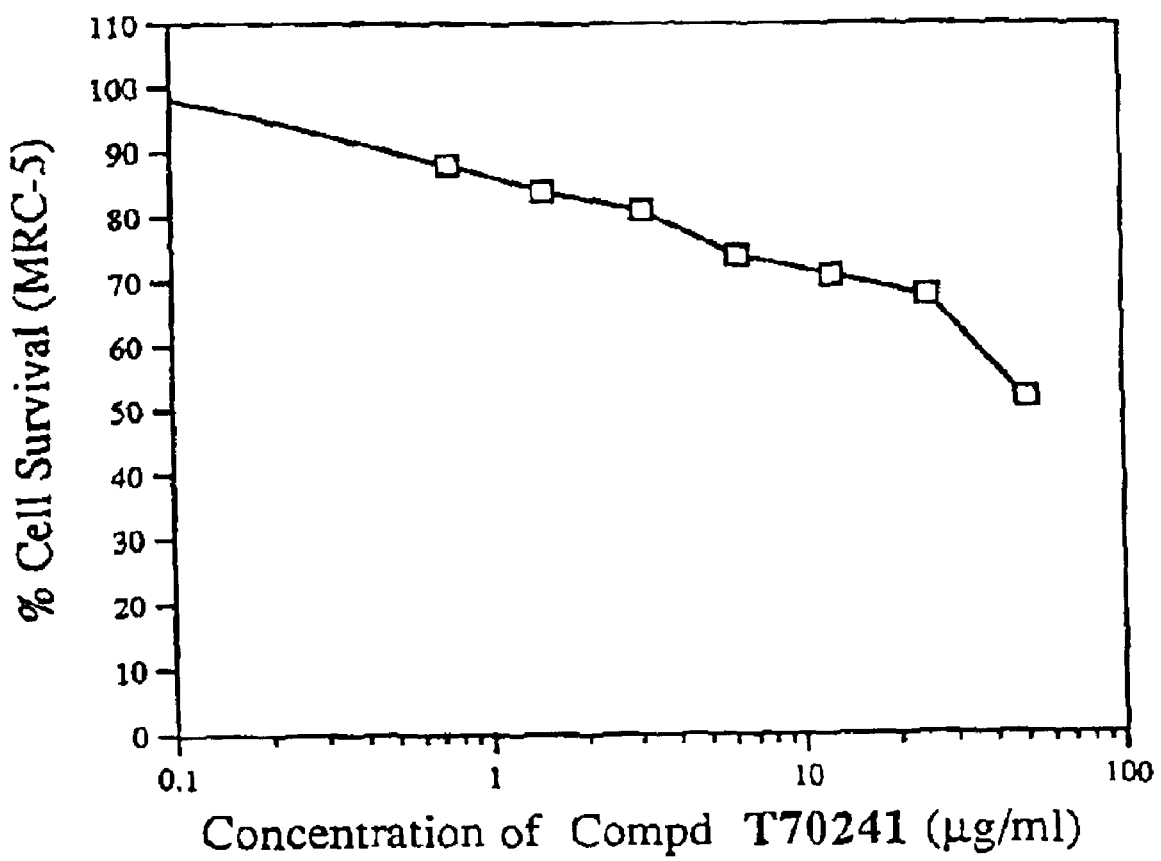
FIG. 9A shows the toxicity of compound 10 on MRC-5 cells in vitro.
Figure 9:
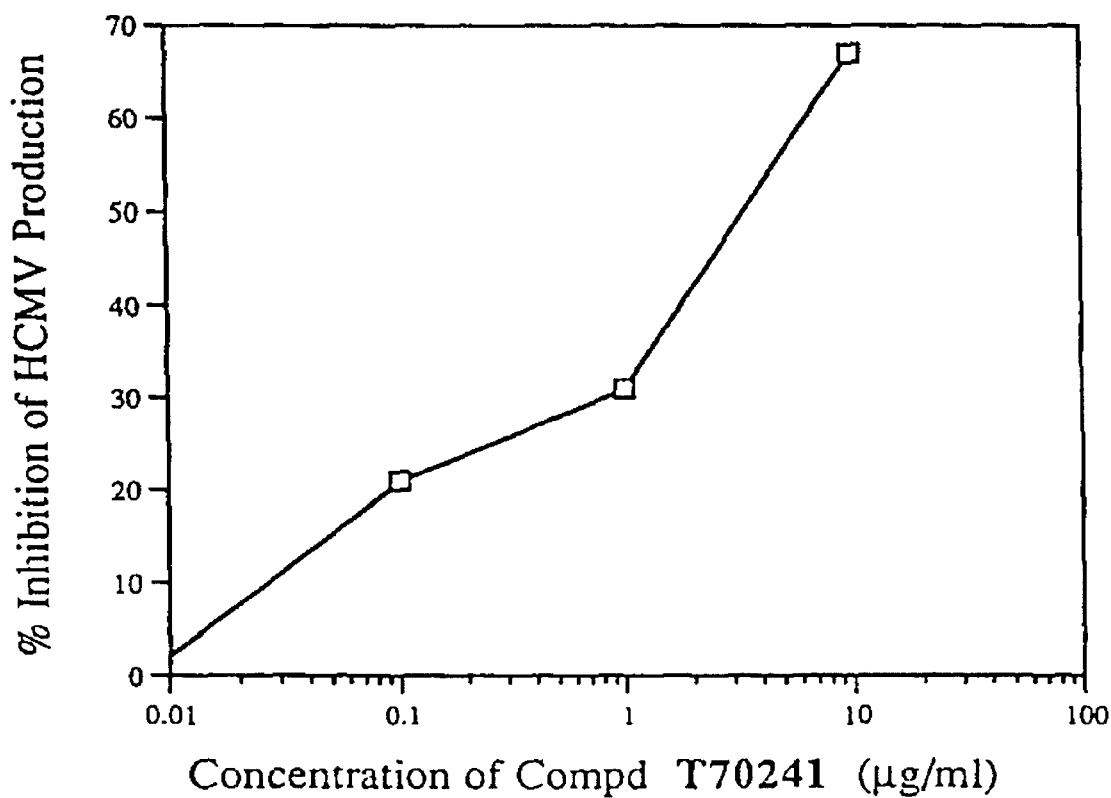
FIG. 9B shows the inhibitory effect of compound 10 on HCMV-induced plaques in static MRC-5 cell cultures.

FIG. 9A is a plot of phosphazole (T70241) concentration versus percent MRC-5 cells surviving. The data shows that compound T70241 has a slight toxic effect on growing MRC-5 cells over a four day period, with a $TC_{50} > 50$ μg/mL. As noted above, at the same time compound T70241 is able to inhibit the number of HCMV induced plaques in static MRC-5 cultures over a 5 to 6 day assay (FIG. 9B) with a 50% inhibitory concentration of ($IC_{50}$) of approximately 8.25 μg/mL. This selective activity is very encouraging for the application of phosphazole derivative candidate drugs for the treatment of HCMV.

RSV-1 and HSV-2 Assay

Cell lines. The routine growth and passage of Vero cells were performed in monolayer cultures using minimal essential medium (MEM) with either Hanks [MEM(H)] or Earle [MEM(E)] salts supplemented with 10% calf serum, 100 U/mL penicillin G, and 100 μg/mL streptocycin. Cells were passaged at 1:2 to 1:10 dilutions by using 0.05% trypsin plus 0.02% EDTA in a HEPES buffered salt (HBS) solution.

CPE assays. Vero cells were plated at 4×$10^4$ cells/well in a 96-well microtiter dish in 0.1 mL of culture medium 24 hours before infection with virus at an MOI of 0.001. The virus was allowed to adsorb to the cells for 10 min at 37° C. The virus-containing medium was then removed, and the cells were rinsed three times with fresh medium. Finally, 100-μL aliquots of fresh medium containing the various dilutions of test compounds were added to each well. Plaques were observed 24 hour post-infection, and the degree of CPE was scored 40 to 48 hour post-infection. ACV (acyclovir) was used as a standard in all HSV assays.

Several of the phosphazole compounds were assayed for their ability to inhibit HSV-1 and HSV-2 production in vitro only compound T70269 was active against HSV-1 and HSV-2 with $IC_{50}$ values of 2.75 and 27.75 μg/mL, respectively (Table 4). All the compounds tested were relatively nontoxic and ganciclovir (DHPG) and acyclovir (ACV) were used as controls in these assays.

EXAMPLE 49

Enzymatic hydrolysis by adenosine deaminase

Adenosine deaminase (ADA, adenosine aminohydrolase, EC 3.5.4.4, SIGMA) from calf intestinal mucosa was prepared to give a stock of 1 mg/mL (250–280 units/mL) in pH 7.4, 0.01 M phosphate buffer. The relative rates of hydrolysis of selected compounds by ADA and characterization of the products was carried as follows. Briefly, 0.05–0.1 units of ADA was added to 1.0 mL of a 50 μM solution of a given compound in pH 7.4, 0.01 M phosphate buffer and incubated at 37° C. Fifty-microliter aliquots were taken at time intervals and hydrolysis was quenched by mixing with 0.45 mL of distilled water and then the diluted sample was heated at 95° C. for 6 min to ensure enxyme deactivation. The decrease in substrate concentration and the formation of the products was followed over time by UV-spectroscopic analysis. Adenosine was used as a control in this experiment and one unit is defined as the amount of ADA that hydrolyzes 1.0 μmol of adenosine/min at 25° C.

Adenosine deaminase (ADA) is a ubiquitous catabolic enzyme present in many animal and human tissues (112). In addition to converting adenosine to inosine, this enzyme catalyzes the hydrolysis of numerous 6-substituted purine nucleosides to inosine and guanosine analogs (113) and most adenosine analogs active in vitro usually become inactive in vivo due to ADA hydrolysis. Based on these observation we subjected compound T70241 (the adenine analog) to ADA hydrolysis in vitro using commercially available, purified anzyme. UV spectra of T70241 remained unchanged up to 5 hours in the presence of ADA. At the same time adenosine, used as control in this experiment, was hydrolyzed at the rate of 1.0 pmole/unit per min at 25° C. These results suggest that compound T70241 is not a substrate for ADA.

Primary cell assays. Primary human peripheral blood mononuclear cells (PBMCS) were isolated as described by Ojwang et al. (114). Isolated monocytes were added to 24-well cluster plates (Costar, Cambridge, Mass.) at a concentration of 1×10$^5$ viable cells per well. Culture medium or test material dilutions in culture medium were added to the wells, the plates were then incubated at 37° C. for one hour. TNFα production was subsequently induced by stimulation with 100 μg/mL (final concentration) of LPS (Lot Number 20126F) obtained from Sigma, St. Louis, Mo. The plates were incubated an additional 4, 24 or 48 hours. The supernatant fluids were then harvested and centrifuged to pellet cells or cellular debris, and the supernatant fluids were stored at −70° C. until they were assayed for the presence of TNFα using a commercially available ELISA kit, such as that described in Example 46.

The effect of compound T70241 on LPS-induced TNFα production in primary human blood cells (PBMCs) is shown in Table 3. PBMCs are a mixed population of cells which are considered to be involved in the inflammatory responses due to high levels of TNFα or IL-1β at the inflammation sites. Experiments performed in PBMCs closely mimic the in vivo situation and based on this observation we evaluated compound T70241 in this system. These data show that compound T70241 is able to significantly reduce the levels of TNFα production in the PBMCs even 48 hours post-LPS induction. The level of measurable toxicity in these cells is minimal at the 48 hour time point. Also shown is the percent viable cells after 48 hours of exposure to T70241 in the medium. The fact that compound T70241 inhibited both TNFα and IL-1β in PBMCs is very encouraging to pursue the development of such novel class of compounds.

EXAMPLE 50

Inhibition of TNFα by Pentane Substituted Adenine Analog Phosphazole (T70254)

THP-1 cells were grown and the T70254 phosphazole compound (N-1 pentyl derivative of T70241) was assayed for its effect on TNFα production in the same manner as described in Example 46 for the T70241 compound. The results of the TNFα assay is presented in FIG. 2, along with the comparable results for the xanthine analog (HWA-3138) and the T70241 compound. The N-pentyl substituted phosphazole (T70254) significantly inhibits TNFα production in THP-1 cells when introduced 6 hours after induction with LPS, showing approximately 30% inhibition at 10 μg/mL and approximately 55% at 100 μg/mL.

Phamaceutical Compositions

Certain embodiments of the present invention provide pharmaceutical compositions in which the active ingredient comprises an effective amount of one or more of the phosphazoles disclosed herein, or a suitable salt thereof, along with a pharmaceutically acceptable carrier and any other compatible therapeutic ingredients. In practical use, the inventive pharmaceutical compositions are prepared according to conventional pharmaceutical compounding techniques and the carrier may take a wide variety of forms depending on the form desired for administration, e.g., oral or parenteral. In preparing the compositions for oral dosage form, any of the usual pharmaceutical media may be employed, such as water, glycols, oils, alcohols, lipids, flavoring agents, preservatives, coloring agents, and the like in the case of oral liquid preparations. In the case of aerosols, surfactants for delivery through mucosal membranes. In the case of oral solid preparations, carriers such as starches, sugars, microcrystalline cellulose, diluents, granulating agents, lubricants, binders, disintegrating agents, and the like may be employed. Rectal preparations may include carbowax. Additionally, the compounds of the present invention are suitable for encapsulation in liposomes or for crosslinking with protein carriers and the like. The pharmaceutical compositions of the present invention may be administered by conventional methods such as are usually employed with known nucleo-base, nucleoside or nucleotide analogs.

Certain embodiments of the present invention include methods of treating a broad spectrum of viral infections in humans and animals, including birds, comprising administering to the subject in need of treatment or prevention of a viral infection an effective amount of one of the phosphazole compounds or compositions of the present invention.

Other embodiments of the present invention encompass methods of treating a wide variety of cancerous tumors in animals and plants. The optimum dosages, manner of administration and other variables routinely determined when optimizing a treatment regime may be readily determined by the clinician as is usually done with other imidizole, azole, deazole or triazole based compounds.

A new class of compounds is disclosed herein, along with the manner of synthesizing representative examples. Exemplary compounds have been tested for activity as antiviral and antitumor agents by determining their ability to inhibit TNFα production or IL-1β production in cells in culture, and to reduce the number of HCMV plaques in in vitro culture. Agents that can inhibit the production or maturation of TNFα and IL-1β in these different indications are expected to have excellent therapeutic potential.

It is also expected that where existing heterocyclic compounds and/or nucleosides/nucleotides are known to have a certain function (for example, as a component of a therapeutic composition, a pesticide used in agriculture or an industrial reagent), nitrogen or oxygen atoms within that heterocycle will be exchanged with phosphorus, using the methods of the present invention, to generate a phosphazole analog. Routine testing will thereafter establish the relative activity of the phosphazole analog compared to the progenitor heterocycle or corresponding nucleoside/nucleotide. A phosphazole analog having the desired level of activity may be substituted for the conventional compound to provide an alternative reagent or component with equivalent or superior results.

References

1. M. Honjo, T. Maruyama, M. Horikawa, J. Balzarini and E. De Clercq, *Chem. Pharm. Bull. Tokyo*, 35, 3227 (1987).
2. T. Maruyama and M. Honjo, *Nucleosides Nucleotides*, 7, 203 (1988).
3. K. Issleib, H. Oehme, H. Schmidt and G.-R. Vollmer, In: Phosphorus Chemistry. Proceedings of the 1981 International Conference. ACS Symposium as Series 171, Am. Chem. Soc., Washington, D.C. 1981, pp 405–408.
4. G. Markl and S. Pflaum, *Tetrahedron Lett.*, 28, 1511 (1987).
5. S. Pohl, *Chem. Ber.*, 112, 3159 (1979).
6. B. B. Aggarwal, W. J. Kohr, P. E. Hass, B. Moffat, S. A. Spencer, W. J. Henzel, T. S. Bringman, G. E. Nedwin, D. V. Goeddel and R. N. Harkins, *J. Biol. Chem.*, 260, 2345 (1985).
7. D. Pennica, G. E. Nedwin, J. F. Hayflick, P. H. Seeburg, M. A. Palladino, W. J. Kohr, B. B. Aggarwal and D. V. Goeddel, *Nature*, 312, 724 (1984).
8. R. A. Aiyer and B. B. Aggarwal, In: CRC Handbook on Cytolytic Lymphocytes and Complement: Effectors of the Immune System, E. R. Podack, ed. CRC Press, Inc., Boca Raton, 1988, pp. 105–132.
9. D. V. Goeddel, B. B. Aggarwal, P. W. Gray, D. W. Leung, G. E. Nedwin, M. A. Palladino, J. S. Patton, D. Pennica, H. M. Shepard, B. J. Sugarman and G. H. W. Wong, *Cold Spring Harbor Synp. Quant. Biol.* L1: 597–609 (1986).
10. W. P. Arend, In: Advances in Internal Medicine, Vol. 40. R. W. Schrier, J. D. Baxter, F. Abbound and A. S. Fauci, eds., Mosby Year Book, Inc., 1995, pp. 365–394.
11. Tumor Necrosis Factor: Structure, Function and Mechanism of Action. B. B. Aggarwal and J. Vilcek, eds., Marcel Dekker, New York, 1992, pp. 1–624.
12. A. S. Duncombe, H. E. Heslop, M. Turner, A. Meager, R. Priest, T. Exley and M. A. Brenner, *J. Imnunol.*, 143, 3828 (1989).
13. K. Miura, M. Teramura, S. Hoshino, H. Mizoguchi and T. Sato, *Leuk. Res.*, 16, 281 (1992).
14. S. Wu, C. M. Boyer, R. S. Whitaker, A. Berchuck, J. R. Wiener, J. B. Weinberg and R. C. Bast, Jr., *Cancer Res.*, 53, 1939 (1993).
15. E. Goillot, V. Corbaret, R. Ladenstein, D. Baubet, J. Y. Blay, T. Philip and M. C. Favrot, *Cancer Res.*, 52, 3194 (1992).
16. L. B. Lachman, D. C. Brown and C. A. Dinarello, *J. Immunol.*, 138, 2913 (1987).
17. F. R. Balkwill and F. Burke, *Immunol. Today*, 10, 299 (1989).
18. K. Arai, F.Lee, A. Miyajima, S. Miyatake, N. Arai and T. Yokota, *Ann. Rev. Biochem.*, 59, 783 (1990).
19. B. Beutler and A. Cerami, *Ann. Rev. Immunol.*, 7, 625 (1989).
20. A. Oliff, D. Defeo-Jones, M. Boyer, D. Martinez, D. Klefer, G. Vuocolo, A. Wolfe and S. H. Socher, *Cell*, 50, 555 (1987).
21. B. Beutler, I. W. Milsark and A. C. Cerami, *Science*, 229, 869 (1985).
22. P.-F. Piguet, G. E. Grau, B. Allet and P. Vassalli, *J. Exp. Med.*,- 166, 1280 (1987).
23. W. Held, H. R. MacDonald, I. L. Weissman, M. W. Hess and C. Mueller, *Proc. Natl. Acad. Sci. USA*, 87, 2239 (1990).
24. T. Saxne, M. A. Palladino, Jr., D. Heinegard, N. Talal and F. A. Wollheim, Arthr. *Rheumatism*, 31, 1041 (1988).
25. D. E. Yocum, L. Esparza, S. Durby, J. B. Benjamin, R. Volz and P. Scuderi, *Cell Immunol.*, 122, 131 (1989).
26. J. T. Whicher and S. W. Evans, *Clin. Chem.*, 36, 1269 (1990).
27. G. R. Revankar and R. K. Robins, Cyclic Nucleotides, In: "Handbook of Experimental Pharmacology", Vol. 58/I, J. A. Nathanson and J. W. Kebabian, eds., Springer-Verlag, New York, 1982, pp. 17–151.
28. S. Endres, H.-J. Fulle, B. Sinha, D. Stoll, C. A. Dinarello, R. Gerzer and P. C. Weber, *Immunology*, 72, 56 (1991).
29. R. M. Strieter, D. G. Remick, P. A. Ward, R. N. Spengler, J. P. Lynch, III, J. Larrick and S. L. Kunkel, *Biochem. Biophys. Res. Commun.*, 156 1230 (1988).
30. J. Semmler, U. Gebert, T. Eisenhut, J. Moeller, M. M. Schonharting, A. Allera and S. Endres, *Immunology*, 78, 520 (1993).
31. C. A. Alford and W. J. Britt, "Cytomegalovirus", In: *The Human Hexpesviruses*, B. Roizman, R. J. Whitley and C. Lopez, eds., Raven Press, New York, 1993, pp 227–255.
32. E. S. Mocarski, Jr., "Cytomegalovirus Biology and Replication", In: *The Human Herpesviruses*, B. Roizman, R. J. Whitley and C. Lopez, eds., Raven Press, New York, 1993, pp 173–226.
33. C. A. Alford and W. J. Britt, "Cytomegalovirus", In: *Fields Virology*, IInd Ed., B. N. Fields and D. M. Knipe, eds., Raven Press, New York, 1990, pp 1981–2010.
34. S. Stagno, R. F. Pass, G. Cloud, W. J. Britt, R. E. Henderson, P. D. Walton, D. A. Veren, F. Page and C. A. Alford, *J. Am. Med. Assoc.*, 256, 1904 (1986).
35. C. A. Alford, S. Stagno, R. F. Pass and W. J. Britt, *Rev. Infect. Dis.*, 12, S745 (1990).
36. R. H. Rubin, *Rev. Infect. Dis.*, 12, 5754 (1990).
37. J. R. Wingard, S. Piantadosi, W. H. Burns, M. L. Zahurak, G. W. Santos and R. Saral, *Rev. Infect. Dis.*, 12, 5793 (1990)
38. R. McKenzie, W. D. Travis, S. A. Dolan, S. Pittaluga, I. M. Feuerstein, J. Shelhamer, R. Yarchoan and H. Masur, *Medicine*, 70, 326 (1991).
39. E. C. Reed, R. A. Bowden, P. S. Dandliker, R. E. Lilleby and J. D. Meyers, *Ann. Inter. Med.*, 109, 783 (1988).
40. P. Reusser, S. R. Riddell, J. D. Meyers and P. D. Greenberg, *Blood*, 78, 1373 (1991).
41. G. M. Schmidt, A. Kovacs, J. A. Zaia, D. A. Horak, K. G. Blume, A. P. Nademanee, M. R. O'Donnell, D. S. Snyder and S. J. Forman, *Transplantation*, 46, 905 (1988).
42. H. H. Balfour, Jr., *Rev. Infect. Dis.*, 12, S849 (1990).
43. Collaborative DHPG Treatment Study Group, *New Engl. J. Med.*, 314, 801 (1986).
44. D. E. Henderly, W. R. Freeman, D. M. Causey and N. A. Rao, *Ophthalmology*, 94, 425 (1987).
45. J. D. Meyers, *Ann. Rev. Med.*, 42, 179 (1991).
46. W. L. Drew, R. C. Miner, D. F. Busch, S. E. Follansbee, J. Gullett, S. G. Mehalko, S. M. Gordon, W. F. Owen, Jr., T. R. Matthews, W. C. Buhles and B. DeArmond, *J. Infect. Dis.*, 163, 716 (1991)
47. M. A. Jacobson, W. L. Drew, J. Feinberg, J. J. O'Donnell, P. V. Whitmore, R. D. Miner and D. Parenti, *J. Infect. Dis.*, 163, 1348 (1991).
48. P. Chrisp and S. P. Clissold, *Drugs*, 41, 104 (1991).

49. M. A. Jacobson, *J. AIDS,*1 (suppl), S11 (1992).
50. J. P. Ferris and L. E. Orgel, *J. Am. Chem. Soc.,* 88, 3829 (1966).
51. H. Schumann and L. Rbsch, *J. Organomet. Chem.,* 55, 257 (1973).
52. K.-W. Henneke, U. Schollkopf and T. Neudecker, Liebigs *Ann. Chem.,* 1370 (1979).
53. R. Gompper and H. Ruhle, Liebigs *Ann. Chem.,* 626, 83 (1959).
54. R. Gompper and H. Ruhle, Liebigs *Ann. Chem.,* 626, 92 (1959).
55. R. Lakhan and B. Ternai, *Adv. Heterocycl. Chem.,* 17, 99 (1974).
56. R. G. R. Bacon and H. A. O. Hill, *J. Chem. Soc.,* 1097 (1964).
57. R. G. R. Bacon and H. A. O. Hill, *Quar. Rev., Chem. Soc.,* 19, 95 (1965).
58. H. B. Cottam, C. R. Petrie, P. A. McKernan, R. J. Goebel, N. K. Dalley, R. B. Davidson, R. K. Robins and G. R. Revankar, *J. Bed. Chem.,* 27, 1119 (1984).
59. M. Yoshikawa, T. Kato and T. Takenishi, *Tetrahedron Lett.,* 5065 (1967).
60. M. Smith, G. I. Drummond and H. G. Khorana, *J. Am. Chem. Soc.,* 83, 698 (1961).
61. J. D. Stevens, R. K. Ness and H. G. Fletcher, Jr., *J. Org. Chem.,* 33, 1806 (1968).
62. J. Heinicke, *Tetrahedron Lett.,* 27, 5699 (1986).
63. C. S. Wilcox and R. M. Otoski, *Tetrahedron Lett.,* 27, 1011 (1986).
64. M. Hoffer, *Chem. Ber.,* 93, 2777 (1960).
65. C. P. J. Glaudemans and H. G. Fletcher, Jr., *J. Org. Chem.,* 28, 3004 (1963).
66. M. J. Robins, F. Hansske, N. H. Low and J. I. Park, *Tetrahedron Lett.,* 25, 367 (1984).
67. F. Hansske and M. J. Robins, *Tetrahedron Lett.,* 26, 4295 (1985).
68. G. R. Revankar and R. K. Robins, In: "Chemistry of Nucleosides and Nucleotides", Vol. 2, L. B. Townsend, ed., Plenum Publishing Corp., New York, 1991, pp. 161–398.
69. H. M. Goodman, J. Abelson, A. Landy, S. Brenner and J. D. Smith, *Nature,* 217, 1019 (1968).
70. B. P. Doctor, J. E. Loebel, M. A. Sodd and D. B. Winter, *Science,* 163, 693 (1969).
71. U. L. RajBhandary, S. H. Chang, H. J. Gross, F. Harada, F. Kimura and S. Nishimura, Fed. Proc., *Fed. Am. Soc. Exp. Biol.,* 28, 409 (1969).
72. H. Kasai, Z. Ohashi, F. Harada, S. Nishimura, N. J. Oppenheimer, P. F. Crain, J. G. Liehr, D. L. von Minden and J. A. McCloskey, *Biochemisty,* 14, 4198 (1975).
73. N. Tanaka, R. T. Wu, T. Okabe, H. Yamashita, A. Shimazu and T. Nishimura, *J. Antiobiot.,* 35, 272 (1982).
74. R. T. Wu, T. Okabe, M. Namikoshi, S. Okuda, T. Nishimura and N. Tanaka, *J. Antiobiot.,* 35, 279 (1982).
75. T. Kondo, T. Goto, T. Okabe and N. Tanaka, *Tetrahedron Lett.,* 24, 3647 (1983).
76. V. G. Beylin, A. M. Kawasaki, C. S. Cheng and L. B. Townsend, *Tetrahedron Lett.,* 24, 4793 (1983).
77. K. Ramasamy, R. K. Robins and G. R. Revankar, *J. Chem. Soc., Chem. commun.,* 560 (1989).
78. Dainippon Pharmaceutical Co., Ltd., Antiobiotic AB-116, Japan Kokai Tokkyo KohoJP 58 32,893 (Feb. 1983): *Chem Abstr.,* 99, 37106j (1983).
79. S. Naruto, H. Uno, A. Tanaka, H. Kotani and Y. Takase, *Heterocycles,* 20, 27 (1983).
80. T. Shomura, N. Nishizawa, M. Iwata, J. Yoshida, M. Ito, S. Amano, M. Koyama, M. Kojima and S. Inouye, *J. Antiobiot.,* 36, 1300 (1983).
81. N. Nishizawa, Y. Kondo, M. Koyama, S. Omoto, M. Iwata, T. Tsuruoka and S. Inouye, *J. Antibiot.,* 37, 1 (1984).
82. H. Seto, N. Otake, M. Koyama, H. Ogino, Y. Kodama, N. Nishizawa, T. Tsuruoka and S. Inouye, *Tetrahedron Lett.,* 24, 495 (1983).
83. R. Kazlauskas, P. T. Murphy, R. J. Wells, J. A. Baird-Lambert and D. D. Jamieson, *Aust. J. Chem.,* 36, 165 (1983).
84. Y. Kato, N. Fusetani, S. Matsunaga and K. Hashimoto, *Tetrahedron Lett.,* 26, 3483 (1985).
85. E. A. Meade, S. H. Krawczyk and L. B. Townsend, *Tetrahedron Lett.,* 29, 4073 (1988).
86. P. S. Ritch and R. I. Glazer, In: "Developments in Cancer Chemotherapy", R. I. Glazer, ed., CRC Press, Inc., Ohio, (1984), pp. 1–33.
87. R. K. Robins and G. R. Revankar, *Med. Res. Reviews,* 5, 273 (1985).
88. T. Kato, H. Kimura and K. Tanji, *Chem. Pharm. Bull.,* 26, 3880 (1978).
89. T. Reichstein and H. Zschokke, *Helv. Chim. Acta.,* 15, 268 (1932).
90. G. R. Revankar and R. K. Robins, *Nucleosides Nucleotides,* 8, 709 (1989).
91. F. Seela, U. Bindig, H. Driller, W. Herdering, K. Kaiser, A. Kehne, H. Rosemeyer and H. Steker, *Nucleosides Nucleotides,* 6, 1 (1987).
92. T. Reichstein and H. Zschokke, *Helv. Chim. Acta,* 15, 268 (1932).
93. H. E. Faith, U.S. Pat. No. 2,405,820 (1946).
94. K. Ramasamy, R. V. Joshi, R. K. Robins and G. R. Revankar, *J. Chem. Soc. Perkin Trans.* 1, 2375 (1989).
95. C. R. Petrie, H. B. Cottam, P. A. McKernan, R. K. Robins and G. R. Revankar, *J. Med. Chem.,* 28, 1010 (1985).
96. B. K. Bhattacharya, R. K. Robins and G. R. Revankar, *J. Heterocycl. Chem.,* 27, 795 (1990).
97. B. K. Bhattacharya, T. S. Rao and G. R. Revankar, *J. Chem. Soc. Perkin Trans.* 1, 1543 (1995).
98. K. Ramasamy, B. G. Ugarkar, P. A. McKernan, R. K. Robins and G. R. Revankar, *J. Med. Chem.,* 29, 2231 (1986).
99. R. A. Earl and L. B. Townsend, *J. Heterocycl. Chem.,* 11, 1033 (1974).
100. Y. S. Sanghvi, N. B. Hanna, S. B. Larson, J. M. Fujitaki, R. C. Willis, R. A. Smith, R. K. Robins and G. R. Revankar, *J. Ned. Chem.,* 31, 330 (1988).
101. M. Kawana, G. A. Ivanovics, R. J. Rousseau and R. K. Robins, *J. Med. Chem.,* 15, 841 (1972).
102. K. Anzai and S. Suzuki, *J. Antiobiot.,* 14A, 253 (1961).
103. K. Anzai, J. Nagatsu and S. Suzuki, *J. Antibiot.,* 14A, 340 (1961).
104. J. A. Montgomery, In: *Nucleosides, Nucleotides and their Biological Applications,* J. L. Rideout, D. W. Henry and L. M. Beacham III, eds., Academic Press, New York, 1983, pp 19–46.

105. K. Karaghiosoff, W. S. Sheldrick and A. Schmidpeter, *Chem. Ber.,* 119, 3213 (1986).
106. J. P. Ferris, B. Devadas, C. -H. Huang and W.-Y. Ren, *J. Org. Chem.,* 50, 747 (1985).
107. P. A. S. Smith, In: Open Chain Nitrogen Compounds, Vol. 2, W. A. Benjamin, ed., New York, 1965, p 75.
108. M. J. Robins and P. W. Hatfield, *Can. J. Chem.,* 60, 547 (1982).
109. L. M. Beauchamp, B. L. Serling, J. E. Kelsey, K. K. Biron, P. Collins, J. Selway, J.-C. Lin and H. J. Schaeffer, *J. Med. Chem.,* 31, 144 (1988).
110. C. C. Bhat, In: Synthetic Procedures in Nucleic Acid Chemistry, W. W. Zorbach and R. S. Tipson, eds., Interscience, New York, 1968, pp 521–522.

Brief Description of the Tables

Table 1 shows certain phosphazoles arranged by type of heterocycle and by type of substituent, correlated with their compound numbers used in the examples.

Table 2 shows the inhibition of TNFα and IL-β production in THP-1 cells stimulated with lipopolysaccaride (LPS) by certain phosphazoles, as well as the cytotoxicity of the corresponding compounds on THP-1 cells.

Table 3 shows the inhibition of TNFα and IL-1β production in PBYCs stimulated with LPS by the adenine analog, compound 10 (T70241), as well as the viability of the cells in the presence of T70241.

Table 4 shows anti-HCMV, HSV-1 and HSV-2 activity as well as the cytotoxicity in vitro of certain phosphazoles.

TABLE 1

Representative Phosphazoles for Use as Pharmaceutical Agents

| | Nucleosides/Nucleotides (Ribo, Deoxyribo, 3',5'-cyclic, etc.) | | | Miscellaneous Phosphazoles |
|---|---|---|---|---|
| Heterocycles | N-nucleosides | | P-nucleosides | N and/or P substituted |
| Adenine (10), T70241 | soAdo (21), R = Ribo, T70264 | | denosine (44) | cyclovir of Ade (21), 70268 |
| Hypoxanthine (12), T70256 | sodAdo (21), R = dRibo, T70265 | | nosine (51), X = 0 | anciclovir of Ade (21), 70269 |
| Xanthine (13), T70270 | denosine (30), R = Ribo | | hioinosine (51), X = 0 | lkyl of Ade (21), R = pentyl, T70254 |
| 6-Chlompurine (14) | nosine (31), R = Ribo | | uanosine (54) | |
| 6-Mercaptopurine (15), T70245 | uanosine (39), R = Ribo | | dG (61) | klenyl of Ade (21), = pentenyl, |
| Guanine (18), T70242 | -AzaAdo (92), R = Ribo | | MP (48) | T70262, T70263 |
| 2-NH$_2$-6-CI-purine (19a) | -AzaIno (94), R = Ribo | | AMP (49) | PMPA (30), R = HPMP linkage |
| L-Thioguanine (19b) | -PhosphaAdo (100) | | GMP (58) | cyclovir (39), R = CH$_2$OCH$_2$CH$_2$ |
| Caffeine (20), T70271 | -Phosphalno (102) | | ubercidin (67) | anciclovir (39), |
| | -PhosphaGuo (105) | | -Deazalno (69) | R = CH$_2$OCH(CH$_2$OH)$_2$ |
| | | | -DeazaGuo (77), R = Ribo | |
| | | | angivamycin (84) | |
| | | | oyocamycin (86) | |
| | | | hiosangivamycin (87), X = S | |

Numbers in parentheses refer to certain target compound nos. in the reaction schemes described in the examples. "T" numbers such as T7024 I, -70242, -70245, -70254, -70256, -70262, -70263, -70268, -70269, -70270, etc. indicate proprietary reference nos. of the compounds.

111. A. F. Lewis, J. C. Drach, S. M. Fennewald, J. H. Huffman, R. G. Ptak, J. P. Sommadossi, G. R. Revankar and R. F. Rando, *Antimicrob. Agents Chemother.,* 38, 2889 (1994).
112. D. H. W. Ho, C. Pincus, C. J. Carter, R. S. Benjamin, E. J. Freireich and G. P. Bodey, *Cancer Treat. Rep.,* 64, 629 (1980).
113. H. Ford, Jr., M. A. Siddiqui, J. S. Driscoll, V. E. Marquez, J. A. Kelley, H. Mitsuya and T. Shirasaka, *J. Med. Chem.,* 38, 1189 (1995).
114. J. O. Ojwang, R. W. Buckheit, Y. Pommier, A. Mazumder, K. DeVreese, J. A. Este, D. Reyman, L. A. Pallansch, C. Lackman-Smith, T. L. Wallace, E. De Clercq, M. S. McGrath and R. F. Rando, *Antimicrob. Agents Chemother.,* 39, 2426 (1995).
115. Riley, T. A., S. B. Larson, T. L. Avery, R. A. Finch and R. K. Robins, *J. Med. Chem.,* 33, 572–6 (1990)

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference, to the extent that they provide materials and methods not specifically shown.

TABLE 2

Inhibition of TNFα and IL-1β in THP-1 Cells by Representative Phosphazoles

| | IC$_{50}$ (μg/ml)[a] | | TC$_{50}$ (μg/ml)[b] |
|---|---|---|---|
| Compd No. | TNFα | IL-1β | Growing THP-1 |
| T70241 | 23.9 | 16.10 | >1000 |
| T70270 | 238.85 | >250 | ND |
| T70256 | 168.5 | 170.4 | ND |
| T70271 | 37.33 | >250 | ND |
| T70264 | 126.27 | >100 | 117.51 |
| T70254 | 19.4 | 152.5 | 14.72 |
| T70260 | >250 | ND | 18.9 |
| T70262 | <10 | >10 | 3.9 |
| T70261 | >250 | ND | >250 |
| T70268 | >100 | >100 | ND |
| T70269 | >100 | >100 | ND |
| T70265 | 26.17 | >100 | 104.52 |
| Adenine | >250 | >250 | ND |

TABLE 2-continued

Inhibition of TNFα and IL-1β in
THP-1 Cells by Representative Phosphazoles

| Compd No. | TNFα | $IC_{50}$ (μg/ml)[a] IL-1β | $TC_{50}$ (μg/ml)[b] Growing THP-1 |
|---|---|---|---|
| Adenosine | 100 | >250 | ND |
| HWA-3138 | 254.6 | >500 | 316.02 |

[a]$IC_{50}$ = inhibitory concentration at 50% level;
[b]Drug dose required to inhibit log-phase growing cells by 50%;
ND, not determined.
*HWA-3138 is a xanthine analog reported by Semmler et al., 1993, Immunology 78:520.

TABLE 3

Inhibition of TNFα and IL-1β in PBMCs by Compound T70241

| Treatment of PBMCs | % Inhibition of TNFα* | | | % Inhibition of IL-1β* | | | % Viable Cells |
|---|---|---|---|---|---|---|---|
| | 4 h | 24 | 48 h | 4 h | 24 h | 48 h | 48 h |
| +LPS + 0 μg/ml of T70241 | 0 | 0 | 0 | 0 | 0 | 0 | 105 |
| +LPS + 10 μg/ml of T70241 | 0 | −3 | −9 | 18 | 6 | 4 | 104 |
| +LPS + 50 μg/ml of T70241 | 50 | 58 | 51 | 86 | 24 | 36 | 83 |
| +LPS + 100 μg/ml of T70241 | 76 | 81 | 79 | 98 | 78 | 70 | 94 |
| +LPS + 250 μg/ml of T70241 | 76 | 84 | 82 | 99.7 | 86 | 75 | 88 |

*Percent inhibition of TNFα and IL-1β are presented relative to the control (+LPS + 0 μg/ml of T70241)
LPS = Lipopolysaccharide

TABLE 4

Anti-HCMV Activity of Representative Phosphazoles

| Compd | $IC_{50}$ (μg/ml)[a] | | | $TC_{50}$ (μg/ml)[b] | | | |
|---|---|---|---|---|---|---|---|
| | HCMV | HSV-I | HSV-2 | Growing MRC-5 | Static NIRC-5 | Growing Vero | Static Vero |
| T70241 | 8.08 | >50 | >50 | >50 | >50 | >50 | >50 |
| T20254 | >50 | >50 | >50 | 17.95 | 9.25 | 8.18 | 18.17 |
| T70268 | >50 | >50 | >50 | >50 | >50 | >50 | >50 |
| T70269 | 26.1 | 2.75 | 27.75 | >50 | >50 | 41.41 | >50 |
| ACV | ND | 0.1 | 0.74 | >250 | >250 | >250 | >250 |
| DHPG | 3.5 | ND | ND | >250 | >250 | >250 | >250 |

[a]$IC_{50}$ = inhibitory concentration at 50% level
[b]Drug dose required to inhibit log-phase growing cells by 50% or concentrations resulting in 50% cell death (static cells);
ND = not determined.

What is claimed is:

1. A pyrimidophosphazole having a five membered heterocyclic ring, the five membered heterocyclic ring having a nitrogen atom and a trivalent phosphorus atom and the pyrimidophosohazole ring system being of the general structure:

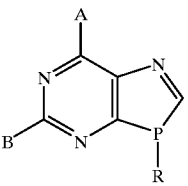

wherein

A is selected from the group consisting of H, $NH_2$, O or Cl;

B is selected from the group consisting of H, $NH_2$, or Q; and

R is selected from the group, consisting of H,

—$(CH_2)_4CH_3$,

—$(CH_2)_5CH_3$,

—$CH_2CH\!\!=\!\!CH_2$,

—$CH_2CH\!\!=\!\!CHCH_2CH_3$ (cis and trans),

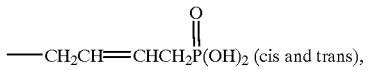

—$CH_2CH\!\!=\!\!C(CH_3)_2$,

—$(CH_2)_3CH_2OH$,

—$CH_2CH\!\!=\!\!CHCH_2OH$,

—$CH_2CH\!\!=\!\!C(CH_3)_2$,

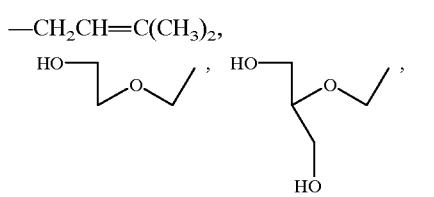

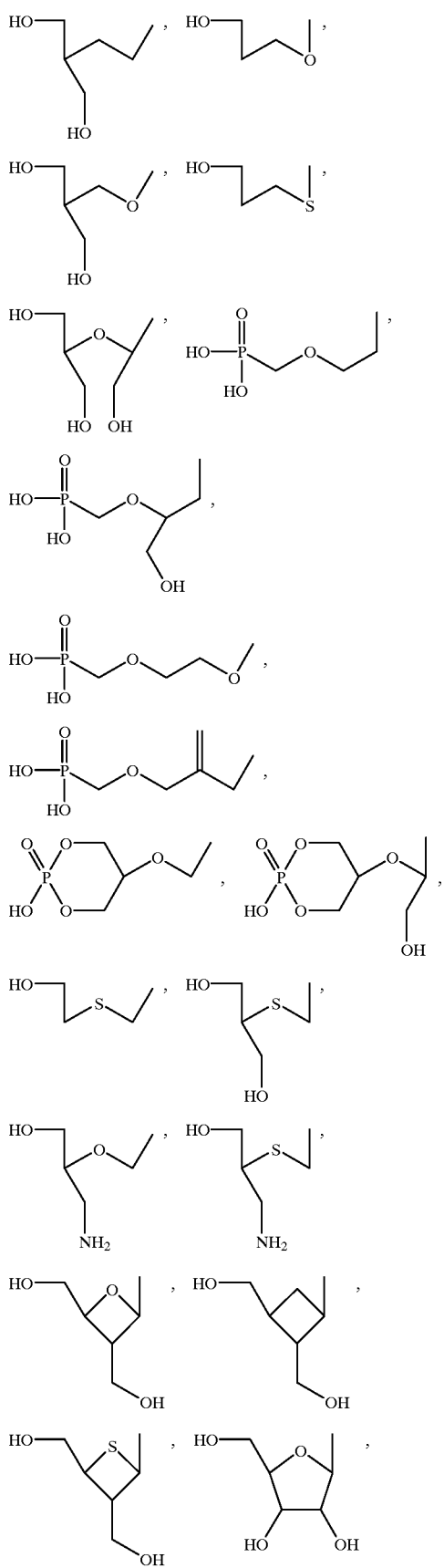
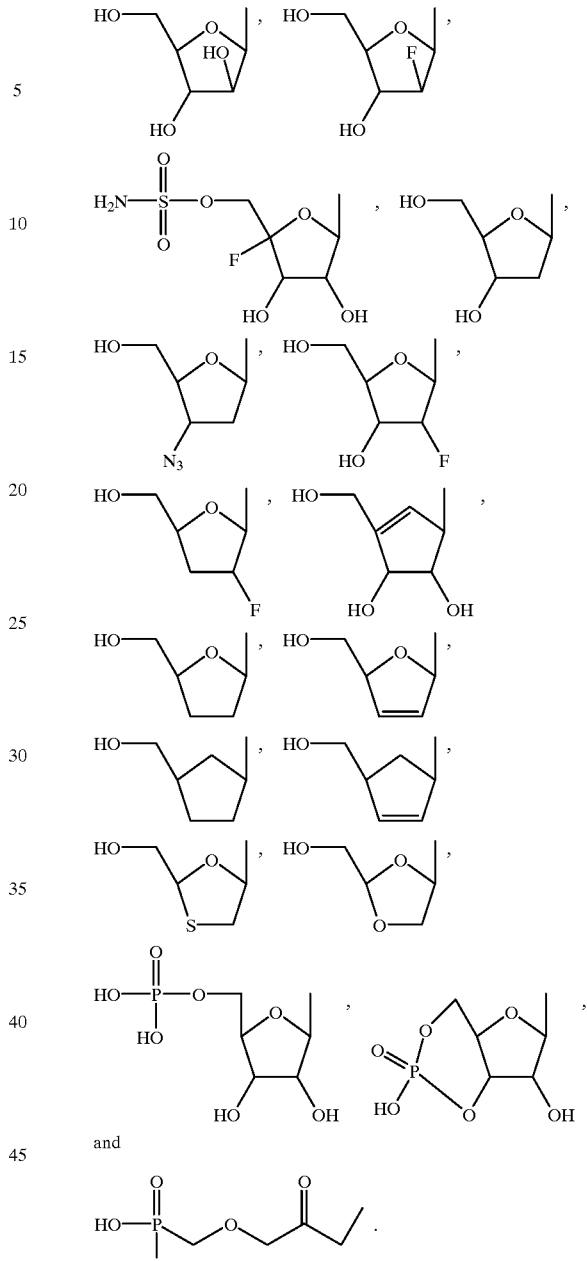
and
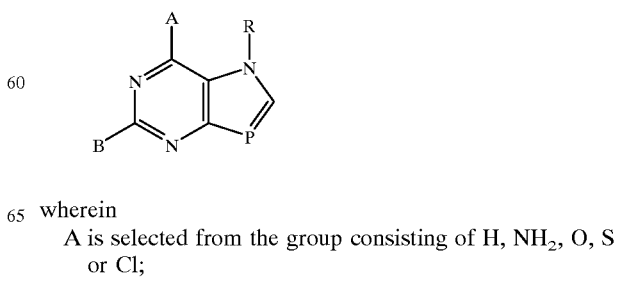
2. A compound of claim 1 wherein A is $NH_2$ and B is H.
3. A compound of claim 1 wherein A is O and B is $NH_2$.
4. A compound of claim 1 wherein A is O and B is H.
5. A compound of claim 1 wherein A is O and B is O.
6. A compound having the structure
wherein
A is selected from the group consisting of H, $NH_2$, O, S or Cl;

B is selected from the group consisting of H NH$_2$, or O; and
R is selected from the group consisting of H,
—(CH$_2$)$_4$CH$_3$,
—(CH$_2$)$_5$CH$_3$,
—CH$_2$CH=CH$_2$,
—CH$_2$CH=CHCH$_2$CH$_3$ (cis and trans),
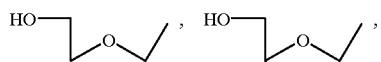
—CH$_2$CH=CHCH$_2$P(OH)$_2$ (cis and trans),
—CH$_2$CH=C(CH$_3$)$_2$,
—(CH$_2$)$_3$CH$_2$OH,
—CH$_2$CH=CHCH$_2$OH,
—CH$_2$CH=C(CH)$_2$,
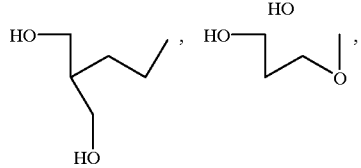
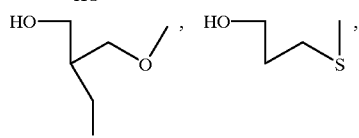
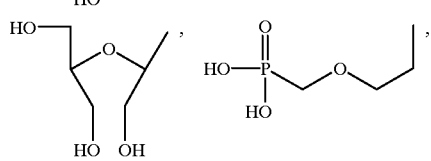
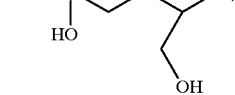
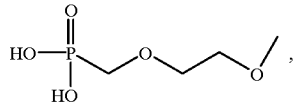
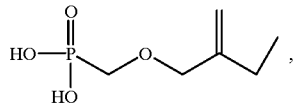
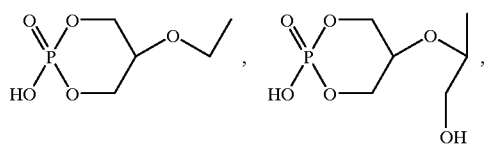
-continued
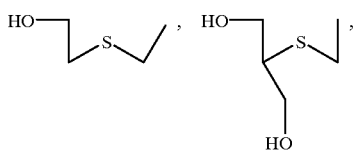
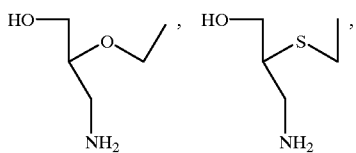
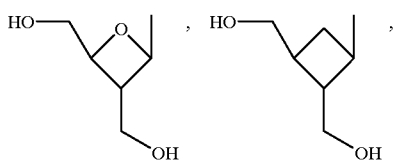
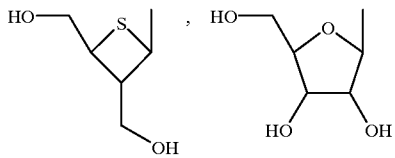
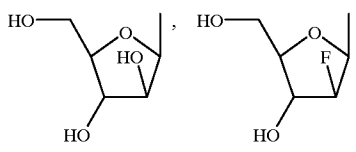
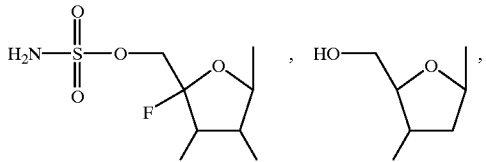
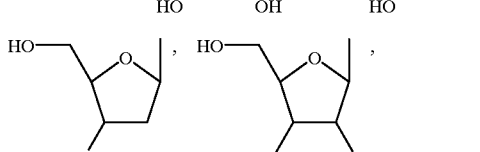
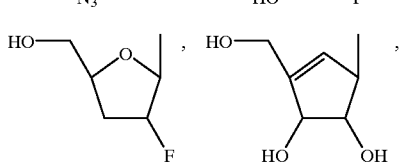
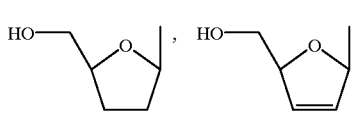
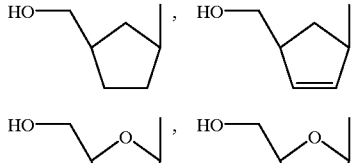
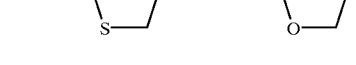

-continued

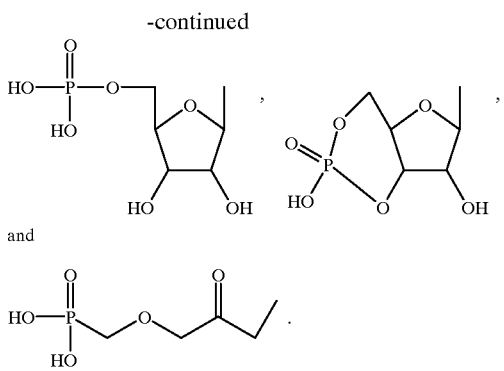

7. A compound of claim 6 wherein A is NH$_2$, and B is H.
8. A compound of claim 6 wherein A is O and B is NH$_2$.
9. A compound of claim 6 wherein A is O and B is H.
10. A compound of claim 6 wherein A is O and B is O.

11. A pharmaceutical composition comprising a compound of claim 1 and a pharmaceutically acceptable carrier.
12. A pharmaceutical composition comprising a compound of claim 6 and a pharmaceutically acceptable carrier.
13. A pharmaceutical composition comprising a compound of claim 2 and a pharmaceutically acceptable carrier.
14. A pharmaceutical composition comprising a compound of claim 3 and a pharmaceutically acceptable carrier.
15. A pharmaceutical composition comprising a compound of claim 4 and a pharmaceutically acceptable carrier.
16. A pharmaceutical composition comprising a compound of claim 5 and a pharmaceutically acceptable carrier.
17. A pharmaceutical composition comprising a compound of claim 7 and a pharmaceutically acceptable carrier.
18. A pharmaceutical composition comprising a compound of claim 8 and a pharmaceutically acceptable carrier.
19. A pharmaceutical composition comprising a compound of claim 9 and a pharmaceutically acceptable carrier.
20. A pharmaceutical composition comprising a compound of claim 10 and a pharmaceutically acceptable carrier.

* * * * *